(12) United States Patent
Veige et al.

(10) Patent No.: US 9,464,104 B2
(45) Date of Patent: Oct. 11, 2016

(54) ONO PINCER LIGANDS AND ONO PINCER LIGAND COMPRISING METAL COMPLEXES

(71) Applicant: UNIVERSITY OF FLORIDA RESEARCH FOUNDATION, INC., Gainesville, FL (US)

(72) Inventors: Adam Steven Veige, Gainesville, FL (US); Matthew O'Reilly, Gainesville, FL (US); Muhammad Tariq Jan, Peshawar (PK)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/077,822

(22) Filed: Nov. 12, 2013

(65) Prior Publication Data

US 2014/0073800 A1    Mar. 13, 2014

Related U.S. Application Data

(63) Continuation-in-part of application No. PCT/US2012/037302, filed on May 10, 2012.

(60) Provisional application No. 61/484,793, filed on May 11, 2011.

(51) Int. Cl.
| | |
|---|---|
| *C07F 11/00* | (2006.01) |
| *C07C 215/50* | (2006.01) |
| *C07D 207/323* | (2006.01) |
| *C07C 215/82* | (2006.01) |
| *C07C 213/02* | (2006.01) |

(52) U.S. Cl.
CPC ........... *C07F 11/005* (2013.01); *C07C 213/02* (2013.01); *C07C 215/50* (2013.01); *C07C 215/82* (2013.01); *C07F 11/00* (2013.01)

(58) Field of Classification Search
CPC  C07F 11/005; C07C 215/50; C07D 207/323
See application file for complete search history.

(56) References Cited

U.S. PATENT DOCUMENTS

2008/0177020 A1   7/2008  Agapie et al.

FOREIGN PATENT DOCUMENTS

| EP | 2093229 | 8/2009 |
| WO | WO 2010-018570 | 2/2010 |
| WO | WO 2010-101993 | 9/2010 |

OTHER PUBLICATIONS

Kostyuchenko et al. (CAPLUS Abstract of: Vysokomolekulyarnye Soedineniya, Seriya A (1984), 26(5), 900-8).*
Yahagi (CAPLUS Abstract of: Kogyo Kagaku Zasshi (1971), 74(6), 1251-8).*
Duff et al. (CAPLUS Abstract of: Journal of the Chemical Society (1951) 1512-15).*
Zigeuner et al. (CAPLUS Abstract of: Monatshefte fuer Chemie (1952), 83, 100-13).*
Zarkesh, R.A. et al., "Reactivity of Diazoalkanes with Tantalum(V) Complexes of a Tridentate Amido-Bis(phenolate) Ligand," *Organometallics*, 2009, pp. 6629-6631, vol. 28.

* cited by examiner

*Primary Examiner* — Robert Havlin
(74) *Attorney, Agent, or Firm* — Saliwanchik, Lloyd & Eisenschenk

(57) ABSTRACT

Embodiments of the invention are directed to ONO pincer ligands that can be in a trianionic, protonated or protonated equivalent form. The ONO pincer ligand can be combined with a transition metal comprising compound to form an ONO pincer ligand comprising transition metal complex. By choice of the ONO pincer ligand structure, the steric and electronic properties of the transition metal complexes therefrom can be controlled. The ONO pincer ligands comprise a central nitrogen atom that is disubstituted with a pair of three atom comprising bridges where the three atoms are three $sp^2$ hybridized carbons or the three atoms are a pair of $sp^2$ hybridized carbons and an $sp^3$ hybridized carbon or silicon.

13 Claims, 49 Drawing Sheets

*Figure 11* -- *Crystal data and structure refinement for* 6

| | |
|---|---|
| Identification code | orei24 |
| Empirical formula | $C_{27}H_{26.94}Br_{0.03}F_{12}NO_3W$ |
| Formula weight | 827.68 |
| Temperature | 100(2) K |
| Wavelength | 0.71073 Å |
| Crystal system | Triclinic |
| Space group | P-1 |
| Unit cell dimensions | a = 8.5483(3) Å   $\alpha$= 86.891(2)°. |
| | b = 9.4574(3) Å   $\beta$= 82.183(2)°. |
| | c = 19.5076(6) Å   $\gamma$ = 70.699(2)°. |
| Volume | 1474.54(8) Å$^3$ |
| Z | 2 |
| Density (calculated) | 1.864 Mg/m$^3$ |
| Absorption coefficient | 4.064 mm$^{-1}$ |
| F(000) | 806 |
| Crystal size | 0.14 x 0.12 x 0.08 mm$^3$ |
| Theta range for data collection | 1.05 to 25.48°. |
| Index ranges | -10≤h≤10, -11≤k≤11, -23≤l≤23 |
| Reflections collected | 28207 |
| Independent reflections | 5441 [R(int) = 0.0620] |
| Completeness to theta = 25.48° | 99.1 % |
| Absorption correction | Numerical |
| Max. and min. transmission | 0.6607 and 0.5304 |
| Refinement method | Full-matrix least-squares on F$^2$ |
| Data / restraints / parameters | 5441 / 0 / 403 |
| Goodness-of-fit on F$^2$ | 1.050 |
| Final R indices [I>2sigma(I)] | R1 = 0.0251, wR2 = 0.0476 [4758] |
| R indices (all data) | R1 = 0.0337, wR2 = 0.0503 |
| Largest diff. peak and hole | 1.198 and -0.981 e.Å$^{-3}$ |

$R1 = \Sigma(||F_o| - |F_c||) / \Sigma|F_o|$ $wR2 = [\Sigma[w(F_o^2 - F_c^2)^2] / \Sigma[w(F_o^2)^2]]^{1/2}$ $S = [\Sigma[w(F_o^2 - F_c^2)^2] / (n-p)]^{1/2}$ $w = 1/[\sigma^2(F_o^2)+(m*p)^2+n*p]$, $p = [max(F_o^2,0)+ 2* F_c^2]/3$, m & n are constants.

*Figure 12*-- *Atomic coordinates (x $10^4$) and equivalent isotropic displacement parameters ($Å^2$ x $10^3$) for 6*

U(eq) is defined as one third of the trace of the orthogonalized $U^{ij}$ tensor.

| Atom | X | Y | Z | U(eq) |
|---|---|---|---|---|
| W1 | 3609(1) | 1736(1) | 2549(1) | 16(1) |
| F1 | 5880(2) | 4612(2) | 2861(1) | 30(1) |
| F2 | 7688(2) | 2958(2) | 3406(1) | 27(1) |
| F3 | 6058(2) | 4965(2) | 3925(1) | 30(1) |
| F4 | 6595(2) | 982(2) | 4222(1) | 29(1) |
| F5 | 5490(2) | 2925(2) | 4863(1) | 31(1) |
| F6 | 3976(2) | 1660(2) | 4595(1) | 31(1) |
| F7 | 1602(3) | 3244(2) | 8(1) | 28(1) |
| F8 | 2913(3) | 1095(2) | 423(1) | 31(1) |
| F9 | 4092(2) | 2785(2) | 270(1) | 29(1) |
| F10 | -894(2) | 4073(2) | 1021(1) | 27(1) |
| F11 | 17(3) | 1759(2) | 1329(1) | 35(1) |
| F12 | -415(2) | 3500(2) | 2066(1) | 28(1) |
| O1 | 5040(3) | 2101(3) | 3171(1) | 19(1) |
| O2 | 3011(3) | 2015(3) | 1620(1) | 20(1) |
| O3 | 5245(3) | -24(3) | 2314(1) | 18(1) |
| N1 | 2585(3) | 3959(3) | 2559(2) | 17(1) |
| Br | -970(20) | 5834(19) | 2883(9) | 50(4) |
| C1 | 4814(4) | 3133(4) | 3689(2) | 18(1) |
| C2 | 3058(4) | 4308(4) | 3776(2) | 17(1) |
| C3 | 2080(4) | 4656(4) | 3227(2) | 17(1) |
| C4 | 460(4) | 5697(4) | 3337(2) | 20(1) |
| C5 | -103(4) | 6470(4) | 3956(2) | 22(1) |
| C6 | 889(4) | 6213(4) | 4487(2) | 19(1) |
| C7 | 2446(4) | 5116(4) | 4387(2) | 18(1) |
| C8 | 6117(4) | 3925(4) | 3474(2) | 20(1) |
| C9 | 5219(4) | 2179(4) | 4348(2) | 22(1) |
| C10 | 309(4) | 7124(4) | 5144(2) | 24(1) |
| C11 | 1969(4) | 3106(4) | 1228(2) | 17(1) |
| C12 | 2072(4) | 4648(4) | 1346(2) | 17(1) |
| C13 | 2442(4) | 4975(4) | 1990(2) | 16(1) |
| C14 | 2661(4) | 6366(4) | 2059(2) | 21(1) |
| C15 | 2447(4) | 7408(4) | 1526(2) | 21(1) |
| C16 | 2010(4) | 7124(4) | 898(2) | 20(1) |
| C17 | 1849(4) | 5732(4) | 826(2) | 19(1) |
| C18 | 2638(4) | 2562(4) | 475(2) | 23(1) |
| C19 | 150(4) | 3108(4) | 1412(2) | 21(1) |
| C20 | 1761(5) | 8246(4) | 318(2) | 27(1) |
| C21 | 6921(4) | -850(4) | 1986(2) | 23(1) |
| C22 | 7123(5) | -172(5) | 1275(2) | 42(1) |
| C23 | 7040(5) | -2471(5) | 1966(3) | 48(1) |
| C24 | 8137(4) | -623(5) | 2438(2) | 35(1) |
| C25 | 1954(4) | 1209(4) | 3141(2) | 20(1) |
| C26 | 1779(5) | -170(4) | 3514(2) | 30(1) |
| C27 | 3404(5) | -1428(4) | 3571(2) | 34(1) |

Figure 13 -- Bond lengths [Å] and angles [°] for 6

| | |
|---|---|
| W1-O3 | 1.819(2) |
| W1-C25 | 1.882(4) |
| W1-O2 | 1.931(2) |
| W1-O1 | 1.953(2) |
| W1-N1 | 1.993(3) |
| F1-C8 | 1.337(4) |
| F2-C8 | 1.345(4) |
| F3-C8 | 1.339(4) |
| F4-C9 | 1.340(4) |
| F5-C9 | 1.345(4) |
| F6-C9 | 1.335(4) |
| F7-C18 | 1.344(4) |
| F8-C18 | 1.336(4) |
| F9-C18 | 1.333(4) |
| F10-C19 | 1.335(4) |
| F11-C19 | 1.338(4) |
| F12-C19 | 1.328(4) |
| O1-C1 | 1.392(4) |
| O2-C11 | 1.391(4) |
| O3-C21 | 1.462(4) |
| N1-C13 | 1.418(5) |
| N1-C3 | 1.440(4) |
| Br-C4 | 1.571(16) |
| C1-C8 | 1.539(5) |
| C1-C2 | 1.539(4) |
| C1-C9 | 1.541(5) |
| C2-C7 | 1.395(5) |
| C2-C3 | 1.404(5) |
| C3-C4 | 1.405(4) |
| C4-C5 | 1.388(5) |
| C5-C6 | 1.389(5) |
| C6-C7 | 1.387(5) |
| C6-C10 | 1.514(5) |
| C11-C12 | 1.522(5) |
| C11-C19 | 1.547(5) |
| C11-C18 | 1.552(5) |
| C12-C17 | 1.387(5) |
| C12-C13 | 1.411(5) |
| C13-C14 | 1.404(5) |
| C14-C15 | 1.381(5) |
| C15-C16 | 1.392(5) |
| C16-C17 | 1.384(5) |
| C16-C20 | 1.496(5) |
| C21-C23 | 1.505(6) |
| C21-C22 | 1.509(6) |
| C21-C24 | 1.523(5) |
| C25-C26 | 1.499(5) |
| C26-C27 | 1.515(5) |

| | |
|---|---|
| O2-C11-C12 | 111.2(3) |
| O2-C11-C19 | 109.6(3) |
| C12-C11-C19 | 110.3(3) |
| O2-C11-C18 | 103.1(3) |
| C12-C11-C18 | 112.4(3) |
| C19-C11-C18 | 110.1(3) |
| C17-C12-C13 | 119.1(3) |
| C17-C12-C11 | 121.4(3) |
| C13-C12-C11 | 119.5(3) |
| C14-C13-C12 | 117.7(3) |
| C14-C13-N1 | 120.0(3) |
| C12-C13-N1 | 122.3(3) |
| C15-C14-C13 | 121.3(3) |
| C14-C15-C16 | 121.5(3) |
| C17-C16-C15 | 116.8(3) |
| C17-C16-C20 | 121.1(3) |
| C15-C16-C20 | 122.1(3) |
| C16-C17-C12 | 123.5(3) |
| F9-C18-F8 | 106.8(3) |
| F9-C18-F7 | 107.1(3) |
| F8-C18-F7 | 106.3(3) |
| F9-C18-C11 | 110.8(3) |
| F8-C18-C11 | 111.3(3) |
| F7-C18-C11 | 114.1(3) |
| F12-C19-F10 | 106.9(3) |
| F12-C19-F11 | 107.5(3) |
| F10-C19-F11 | 107.0(3) |
| F12-C19-C11 | 110.9(3) |
| F10-C19-C11 | 112.2(3) |
| F11-C19-C11 | 112.0(3) |
| O3-C21-C23 | 107.3(3) |
| O3-C21-C22 | 107.0(3) |
| C23-C21-C22 | 112.9(3) |
| O3-C21-C24 | 106.4(3) |
| C23-C21-C24 | 111.6(3) |
| C22-C21-C24 | 111.3(4) |
| C26-C25-W1 | 137.2(3) |
| C25-C26-C27 | 115.1(3) |

*Figure 14* -- *Anisotropic displacement parameters($Å^2 \times 10^3$) for 6.* anisotropic displacement factor exponent takes the form: $-2\pi^2[\, h^2 a^{*2} U^{11} + ... + 2 h k a^* b^* U^{12}\,]$

| | $U^{11}$ | $U^{22}$ | $U^{33}$ | $U^{23}$ | $U^{13}$ | $U^{12}$ |
|---|---|---|---|---|---|---|
| W1 | 15(1) | 16(1) | 15(1) | -1(1) | 0(1) | -2(1) |
| F1 | 25(1) | 39(1) | 27(1) | 10(1) | -1(1) | -13(1) |
| F2 | 13(1) | 34(1) | 32(1) | -5(1) | 1(1) | -4(1) |
| F3 | 25(1) | 32(1) | 36(2) | -12(1) | 0(1) | -13(1) |
| F4 | 24(1) | 28(1) | 26(1) | 3(1) | -6(1) | 4(1) |
| F5 | 32(1) | 38(1) | 20(1) | -2(1) | -11(1) | -4(1) |
| F6 | 25(1) | 37(1) | 31(1) | 14(1) | 0(1) | -12(1) |
| F7 | 34(1) | 34(1) | 16(1) | 0(1) | -8(1) | -9(1) |
| F8 | 48(1) | 22(1) | 22(1) | -6(1) | -4(1) | -10(1) |
| F9 | 27(1) | 36(1) | 21(1) | -6(1) | 6(1) | -9(1) |
| F10 | 20(1) | 34(1) | 26(1) | 5(1) | -9(1) | -8(1) |
| F11 | 33(1) | 28(1) | 52(2) | 0(1) | -6(1) | -19(1) |
| F12 | 20(1) | 41(1) | 19(1) | -1(1) | 4(1) | -10(1) |
| O1 | 17(1) | 20(1) | 16(1) | -4(1) | -1(1) | 0(1) |
| O2 | 20(1) | 18(1) | 18(1) | -3(1) | -3(1) | -2(1) |
| O3 | 18(1) | 18(1) | 14(1) | 0(1) | 2(1) | -3(1) |
| N1 | 18(1) | 19(2) | 11(2) | -3(1) | -4(1) | -2(1) |
| C1 | 15(2) | 20(2) | 18(2) | -2(2) | 0(2) | -4(2) |
| C2 | 13(2) | 19(2) | 16(2) | -1(2) | 0(2) | -4(1) |
| C3 | 18(2) | 16(2) | 16(2) | -2(2) | 0(2) | -5(1) |
| C4 | 21(2) | 17(2) | 20(2) | -3(2) | 3(2) | -4(2) |
| C5 | 16(2) | 23(2) | 23(2) | -2(2) | 0(2) | -2(2) |
| C6 | 17(2) | 20(2) | 20(2) | -4(2) | 5(2) | -8(2) |
| C7 | 19(2) | 23(2) | 14(2) | 1(2) | -4(2) | -10(2) |
| C8 | 16(2) | 24(2) | 19(2) | 0(2) | 2(2) | -5(2) |
| C9 | 18(2) | 26(2) | 20(2) | 0(2) | -2(2) | -4(2) |
| C10 | 22(2) | 27(2) | 22(2) | -6(2) | 0(2) | -6(2) |
| C11 | 18(2) | 17(2) | 13(2) | 3(2) | -2(2) | -4(2) |
| C12 | 14(2) | 20(2) | 15(2) | 0(2) | 0(2) | -6(1) |
| C13 | 9(2) | 18(2) | 16(2) | -2(2) | 1(1) | 0(1) |
| C14 | 17(2) | 21(2) | 23(2) | -7(2) | -3(2) | -4(2) |
| C15 | 20(2) | 16(2) | 26(2) | 1(2) | -3(2) | -5(2) |
| C16 | 15(2) | 22(2) | 21(2) | 4(2) | -2(2) | -5(2) |
| C17 | 14(2) | 25(2) | 16(2) | 0(2) | -1(2) | -6(2) |
| C18 | 26(2) | 24(2) | 19(2) | -1(2) | -2(2) | -9(2) |
| C19 | 24(2) | 20(2) | 20(2) | 0(2) | -4(2) | -10(2) |
| C20 | 30(2) | 25(2) | 26(2) | 5(2) | -4(2) | -10(2) |
| C21 | 16(2) | 26(2) | 20(2) | -6(2) | 4(2) | 2(2) |
| C22 | 30(2) | 60(3) | 26(3) | -2(2) | 9(2) | -5(2) |
| C23 | 31(2) | 28(3) | 77(4) | -17(2) | 4(2) | -2(2) |
| C24 | 20(2) | 39(3) | 38(3) | -11(2) | -3(2) | 3(2) |
| C25 | 21(2) | 25(2) | 10(2) | 0(2) | 3(2) | -6(2) |
| C26 | 31(2) | 30(2) | 27(3) | -1(2) | 7(2) | -12(2) |
| C27 | 46(2) | 30(2) | 31(3) | 12(2) | -5(2) | -23(2) |

7

***Figure 18*--** *Crystal data and structure refinement for 7*

| | |
|---|---|
| Identification code | tj11 |
| Empirical formula | C44 H56 Mo N2 O4, 2(C4 H10 O) |
| Formula weight | 921.09 |
| Temperature | 100(2) K |
| Wavelength | 0.71073 Å |
| Crystal system | Triclinic |
| Space group | P-1 |
| Unit cell dimensions | a = 11.627(7) Å      $\alpha$ = 84.928(14)°. |
| | b = 14.898(9) Å      $\beta$ = 70.391(13)°. |
| | c = 17.182(10) Å    $\gamma$ = 67.904(13)°. |
| Volume | 2595(3) Å$^3$ |
| Z | 2 |
| Density (calculated) | 1.179 Mg/m$^3$ |
| Absorption coefficient | 0.299 mm$^{-1}$ |
| F(000) | 984 |
| Crystal size | 0.24 x 0.21 x 0.08 mm$^3$ |
| Theta range for data collection | 1.26 to 27.50°. |
| Index ranges | -15≤h≤15, -19≤k≤19, -22≤l≤20 |
| Reflections collected | 43445 |
| Independent reflections | 11917 [R(int) = 0.2995] |
| Completeness to theta = 27.50° | 100.0 % |
| Absorption correction | Numerical |
| Max. and min. transmission | 0.9780 and 0.9348 |
| Refinement method | Full-matrix least-squares on F$^2$ |
| Data / restraints / parameters | 11917 / 0 / 472 |
| Goodness-of-fit on F$^2$ | 0.729 |
| Final R indices [I>2sigma(I)] | R1 = 0.0590, wR2 = 0.1322 [5649] |
| R indices (all data) | R1 = 0.1191, wR2 = 0.1531 |
| Largest diff. peak and hole | 0.635 and -1.029 e.Å$^{-3}$ |

$R1 = \Sigma(||F_o| - |F_c||) / \Sigma|F_o|$ $wR2 = [\Sigma[w(F_o^2 - F_c^2)^2] / \Sigma[w(F_o^2)^2]]^{1/2}$ $S = [\Sigma[w(F_o^2 - F_c^2)^2] / (n-p)]^{1/2}$ $w = 1/[\sigma^2(F_o^2) + (m*p)^2 + n*p]$, $p = [max(F_o^2, 0) + 2* F_c^2]/3$, m & n are constants.

Figure 19 -- *Atomic coordinates (x $10^4$) and equivalent isotropic displacement parameters ($Å^2$ x $10^3$) for 7*

U(eq) is defined as one third of the trace of the orthogonalized $U^{ij}$ tensor.

|     | x | y | z | U(eq) |
|-----|---|---|---|-------|
| Mo1 | 1171(1) | 7203(1) | 2271(1) | 44(1) |
| O1  | -172(3) | 6615(2) | 2501(1) | 51(1) |
| O2  | 2492(3) | 7812(2) | 2100(1) | 50(1) |
| O3  | 2555(3) | 5879(2) | 1956(1) | 50(1) |
| O4  | -232(3) | 8514(2) | 2538(1) | 52(1) |
| N1  | 1028(3) | 7102(2) | 3575(2) | 52(1) |
| N2  | 1215(3) | 7342(2) | 982(2) | 48(1) |
| C1  | -1069(4) | 6513(3) | 3221(2) | 54(1) |
| C2  | -2270(5) | 6481(3) | 3214(2) | 61(1) |
| C3  | -3190(5) | 6456(4) | 3981(3) | 89(2) |
| C4  | -2939(7) | 6433(5) | 4718(3) | 112(2) |
| C5  | -1752(6) | 6409(4) | 4706(3) | 89(2) |
| C6  | -779(5) | 6422(3) | 3967(2) | 64(1) |
| C7  | 555(5) | 6336(3) | 3989(2) | 69(1) |
| C8  | 2815(4) | 8205(3) | 2646(2) | 50(1) |
| C9  | 3272(4) | 8973(3) | 2423(2) | 56(1) |
| C10 | 3635(5) | 9313(3) | 3005(3) | 69(1) |
| C11 | 3537(5) | 8936(4) | 3780(3) | 80(2) |
| C12 | 3042(5) | 8205(4) | 3994(3) | 74(2) |
| C13 | 2710(4) | 7814(3) | 3439(2) | 53(1) |
| C14 | 2329(4) | 6952(3) | 3665(2) | 62(1) |
| C15 | -2531(5) | 6450(3) | 2408(3) | 64(1) |
| C16 | -1429(5) | 5613(3) | 1841(3) | 80(2) |
| C17 | -2673(5) | 7421(3) | 1977(3) | 79(1) |
| C18 | -3834(5) | 6299(5) | 2552(3) | 101(2) |
| C19 | 3331(5) | 9467(3) | 1587(2) | 62(1) |
| C20 | 4186(5) | 8715(4) | 858(2) | 79(2) |
| C21 | 1887(5) | 9983(4) | 1584(3) | 83(2) |
| C22 | 3936(7) | 10243(4) | 1483(3) | 114(2) |
| C23 | 2976(4) | 5287(3) | 1279(2) | 52(1) |
| C24 | 3430(4) | 4268(3) | 1339(2) | 58(1) |
| C25 | 3888(5) | 3708(3) | 612(3) | 74(1) |
| C26 | 3930(5) | 4100(3) | -145(3) | 79(2) |
| C27 | 3460(5) | 5113(3) | -199(2) | 68(1) |
| C28 | 2990(4) | 5709(3) | 508(2) | 53(1) |
| C29 | 2619(4) | 6776(3) | 421(2) | 57(1) |
| C30 | -1009(4) | 9090(3) | 2110(2) | 47(1) |
| C31 | -2266(4) | 9796(3) | 2536(2) | 53(1) |
| C32 | -3040(4) | 10324(3) | 2071(3) | 67(1) |
| C33 | -2629(5) | 10225(3) | 1217(3) | 74(1) |
| C34 | -1389(4) | 9558(3) | 803(2) | 59(1) |
| C35 | -565(4) | 9008(3) | 1233(2) | 47(1) |
| C36 | 800(4) | 8371(3) | 757(2) | 59(1) |
| C37 | 3336(6) | 3778(3) | 2183(3) | 77(2) |
| C38 | 3969(7) | 2663(3) | 2081(3) | 118(2) |
| C39 | 4061(6) | 4099(4) | 2645(3) | 99(2) |
| C40 | 1873(6) | 4067(4) | 2696(3) | 92(2) |
| C41 | -2724(5) | 9971(3) | 3496(2) | 62(1) |
| C42 | -4078(5) | 10812(4) | 3802(3) | 94(2) |
| C43 | -1721(5) | 10252(4) | 3715(3) | 82(2) |
| C44 | -2882(5) | 9055(3) | 3942(3) | 81(2) |

*Figure 20*-- *Bond lengths [Å] and angles [°] for 7*

| | | | | | |
|---|---|---|---|---|---|
| Mo1-O1 | 1.979(3) | C30-C35 | 1.420(5) | C1-C2-C15 | 121.5(4) |
| Mo1-O4 | 1.986(3) | C30-C31 | 1.428(5) | C4-C3-C2 | 122.2(5) |
| Mo1-O2 | 1.992(3) | C31-C32 | 1.381(6) | C5-C4-C3 | 119.8(5) |
| Mo1-O3 | 1.997(3) | C31-C41 | 1.567(5) | C4-C5-C6 | 121.4(5) |
| Mo1-N1 | 2.186(3) | C32-C33 | 1.384(6) | C5-C6-C1 | 118.6(5) |
| Mo1-N2 | 2.191(3) | C33-C34 | 1.389(6) | C5-C6-C7 | 119.1(4) |
| O1-C1 | 1.364(4) | C34-C35 | 1.384(5) | C1-C6-C7 | 122.3(4) |
| O2-C8 | 1.366(5) | C35-C36 | 1.490(5) | N1-C7-C6 | 115.5(4) |
| O3-C23 | 1.357(4) | C37-C40 | 1.539(7) | O2-C8-C9 | 120.8(3) |
| O4-C30 | 1.359(4) | C37-C38 | 1.543(6) | O2-C8-C13 | 118.9(4) |
| N1-C7 | 1.476(5) | C37-C39 | 1.544(7) | C9-C8-C13 | 120.3(4) |
| N1-C14 | 1.503(5) | C41-C43 | 1.538(6) | C10-C9-C8 | 117.4(4) |
| N2-C36 | 1.482(5) | C41-C44 | 1.548(6) | C10-C9-C19 | 120.0(4) |
| N2-C29 | 1.535(5) | C41-C42 | 1.549(6) | C8-C9-C19 | 122.5(4) |
| C1-C6 | 1.415(6) | O1-Mo1-O4 | 90.24(12) | C11-C10-C9 | 122.7(4) |
| C1-C2 | 1.418(6) | O1-Mo1-O2 | 177.12(10) | C12-C11-C10 | 118.6(5) |
| C2-C3 | 1.400(5) | O4-Mo1-O2 | 88.73(12) | C11-C12-C13 | 121.5(4) |
| C2-C15 | 1.521(6) | O1-Mo1-O3 | 88.60(12) | C12-C13-C8 | 119.3(4) |
| C3-C4 | 1.386(7) | O4-Mo1-O3 | 177.26(10) | C12-C13-C14 | 119.4(4) |
| C4-C5 | 1.360(7) | O2-Mo1-O3 | 92.55(12) | C8-C13-C14 | 121.2(4) |
| C5-C6 | 1.393(6) | O1-Mo1-N1 | 89.42(11) | C13-C14-N1 | 112.8(4) |
| C6-C7 | 1.521(6) | O4-Mo1-N1 | 88.58(11) | C2-C15-C16 | 110.1(4) |
| C8-C9 | 1.407(5) | O2-Mo1-N1 | 87.86(11) | C2-C15-C17 | 110.6(4) |
| C8-C13 | 1.418(5) | O3-Mo1-N1 | 93.89(12) | C16-C15-C17 | 110.6(4) |
| C9-C10 | 1.404(6) | O1-Mo1-N2 | 89.06(11) | C2-C15-C18 | 112.1(4) |
| C9-C19 | 1.546(5) | O4-Mo1-N2 | 89.21(10) | C16-C15-C18 | 107.4(4) |
| C10-C11 | 1.384(6) | O2-Mo1-N2 | 93.61(11) | C17-C15-C18 | 106.0(4) |
| C11-C12 | 1.383(6) | O3-Mo1-N2 | 88.29(10) | C22-C19-C20 | 107.1(4) |
| C12-C13 | 1.383(6) | N1-Mo1-N2 | 177.32(12) | C22-C19-C9 | 111.8(4) |
| C13-C14 | 1.490(6) | C1-O1-Mo1 | 131.7(3) | C20-C19-C9 | 110.7(4) |
| C15-C16 | 1.524(6) | C8-O2-Mo1 | 131.7(2) | C22-C19-C21 | 107.7(4) |
| C15-C17 | 1.543(6) | C23-O3-Mo1 | 131.2(2) | C20-C19-C21 | 112.1(4) |
| C15-C18 | 1.550(6) | C30-O4-Mo1 | 131.6(2) | C9-C19-C21 | 107.5(3) |
| C19-C22 | 1.534(6) | C7-N1-C14 | 110.2(3) | O3-C23-C28 | 118.7(4) |
| C19-C20 | 1.545(6) | C7-N1-Mo1 | 113.2(3) | O3-C23-C24 | 120.8(3) |
| C19-C21 | 1.564(7) | C14-N1-Mo1 | 110.3(2) | C28-C23-C24 | 120.5(4) |
| C23-C28 | 1.414(5) | C36-N2-C29 | 109.8(3) | C25-C24-C23 | 117.4(4) |
| C23-C24 | 1.415(5) | C36-N2-Mo1 | 111.4(2) | C25-C24-C37 | 120.4(4) |
| C24-C25 | 1.393(6) | C29-N2-Mo1 | 108.6(2) | C23-C24-C37 | 122.1(4) |
| C24-C37 | 1.554(6) | O1-C1-C6 | 119.5(4) | C26-C25-C24 | 123.1(4) |
| C25-C26 | 1.372(6) | O1-C1-C2 | 119.9(4) | C25-C26-C27 | 119.2(4) |
| C26-C27 | 1.405(6) | C6-C1-C2 | 120.6(4) | C28-C27-C26 | 120.2(4) |
| C27-C28 | 1.392(5) | C3-C2-C1 | 116.9(4) | C27-C28-C23 | 119.5(4) |
| C28-C29 | 1.491(5) | C3-C2-C15 | 121.5(5) | C27-C28-C29 | 119.0(4) |

*Figure 20 (cont.)*-- Bond lengths [Å] and angles [°] for 7

| | |
|---|---|
| C23-C28-C29 | 121.2(3) |
| C28-C29-N2 | 111.9(3) |
| O4-C30-C35 | 120.1(3) |
| O4-C30-C31 | 120.4(3) |
| C35-C30-C31 | 119.5(3) |
| C32-C31-C30 | 117.7(4) |
| C32-C31-C41 | 121.8(4) |
| C30-C31-C41 | 120.5(4) |
| C31-C32-C33 | 123.0(4) |
| C32-C33-C34 | 119.1(4) |
| C35-C34-C33 | 120.7(4) |
| C34-C35-C30 | 119.8(4) |
| C34-C35-C36 | 118.7(3) |
| C30-C35-C36 | 121.4(3) |
| N2-C36-C35 | 116.0(3) |
| C40-C37-C38 | 108.6(5) |
| C40-C37-C39 | 110.5(4) |
| C38-C37-C39 | 106.7(4) |
| C40-C37-C24 | 108.0(4) |
| C38-C37-C24 | 112.2(4) |
| C39-C37-C24 | 110.8(4) |
| C43-C41-C44 | 111.4(4) |
| C43-C41-C42 | 108.2(4) |
| C44-C41-C42 | 107.2(4) |
| C43-C41-C31 | 109.1(4) |
| C44-C41-C31 | 110.2(3) |
| C42-C41-C31 | 110.7(4) |

8

*Figure 24--* Crystal data and structure refinement for 8

| | |
|---|---|
| Identification code | tj11 |
| Empirical formula | C44 H56 Mo N2 O4, 2(C4 H10 O) |
| Formula weight | 921.09 |
| Temperature | 100(2) K |
| Wavelength | 0.71073 Å |
| Crystal system | Triclinic |
| Space group | P-1 |
| Unit cell dimensions | a = 11.627(7) Å    $\alpha$ = 84.928(14)°. |
| | b = 14.898(9) Å    $\beta$ = 70.391(13)°. |
| | c = 17.182(10) Å    $\gamma$ = 67.904(13)°. |
| Volume | 2595(3) Å$^3$ |
| Z | 2 |
| Density (calculated) | 1.179 Mg/m$^3$ |
| Absorption coefficient | 0.299 mm$^{-1}$ |
| F(000) | 984 |
| Crystal size | 0.24 x 0.21 x 0.08 mm$^3$ |
| Theta range for data collection | 1.26 to 27.50°. |
| Index ranges | -15≤h≤15, -19≤k≤19, -22≤l≤20 |
| Reflections collected | 43445 |
| Independent reflections | 11917 [R(int) = 0.2995] |
| Completeness to theta = 27.50° | 100.0 % |
| Absorption correction | Numerical |
| Max. and min. transmission | 0.9780 and 0.9348 |
| Refinement method | Full-matrix least-squares on F$^2$ |
| Data / restraints / parameters | 11917 / 0 / 472 |
| Goodness-of-fit on F$^2$ | 0.729 |
| Final R indices [I>2sigma(I)] | R1 = 0.0590, wR2 = 0.1322 [5649] |
| R indices (all data) | R1 = 0.1191, wR2 = 0.1531 |
| Largest diff. peak and hole | 0.635 and -1.029 e.Å$^{-3}$ |

$R1 = \Sigma(||F_o| - |F_c||) / \Sigma|F_o|$ $wR2 = [\Sigma[w(F_o^2 - F_c^2)^2] / \Sigma[w(F_o^2)^2]]^{1/2}$ $S = [\Sigma[w(F_o^2 - F_c^2)^2] / (n-p)]^{1/2}$ $w = 1/[\sigma^2(F_o^2)+(m*p)^2+n*p]$, $p = [max(F_o^2,0)+ 2*F_c^2]/3$, m & n are constants.

*Figure 25*--*Atomic coordinates ( x $10^4$) and equivalent isotropic displacement parameters ($Å^2$ x $10^3$) for* 8

U(eq) is defined as one third of the trace of the orthogonalized $U^{ij}$ tensor.

| | x | y | z | U(eq) |
|---|---|---|---|---|
| Mo1 | 1171(1) | 7203(1) | 2271(1) | 44(1) |
| O1 | -172(3) | 6615(2) | 2501(1) | 51(1) |
| O2 | 2492(3) | 7812(2) | 2100(1) | 50(1) |
| O3 | 2555(3) | 5879(2) | 1956(1) | 50(1) |
| O4 | -232(3) | 8514(2) | 2538(1) | 52(1) |
| N1 | 1028(3) | 7102(2) | 3575(2) | 52(1) |
| N2 | 1215(3) | 7342(2) | 982(2) | 48(1) |
| C1 | -1069(4) | 6513(3) | 3221(2) | 54(1) |
| C2 | -2270(5) | 6481(3) | 3214(2) | 61(1) |
| C3 | -3190(5) | 6456(4) | 3981(3) | 89(2) |
| C4 | -2939(7) | 6433(5) | 4718(3) | 112(2) |
| C5 | -1752(6) | 6409(4) | 4706(3) | 89(2) |
| C6 | -779(5) | 6422(3) | 3967(2) | 64(1) |
| C7 | 555(5) | 6336(3) | 3989(2) | 69(1) |
| C8 | 2815(4) | 8205(3) | 2646(2) | 50(1) |
| C9 | 3272(4) | 8973(3) | 2423(2) | 56(1) |
| C10 | 3635(5) | 9313(3) | 3005(3) | 69(1) |
| C11 | 3537(5) | 8936(4) | 3780(3) | 80(2) |
| C12 | 3042(5) | 8205(4) | 3994(3) | 74(2) |
| C13 | 2710(4) | 7814(3) | 3439(2) | 53(1) |
| C14 | 2329(4) | 6952(3) | 3665(2) | 62(1) |
| C15 | -2531(5) | 6450(3) | 2408(3) | 64(1) |
| C16 | -1429(5) | 5613(3) | 1841(3) | 80(2) |
| C17 | -2673(5) | 7421(3) | 1977(3) | 79(1) |
| C18 | -3834(5) | 6299(5) | 2552(3) | 101(2) |
| C19 | 3331(5) | 9467(3) | 1587(2) | 62(1) |
| C20 | 4186(5) | 8715(4) | 858(2) | 79(2) |
| C21 | 1887(5) | 9983(4) | 1584(3) | 83(2) |
| C22 | 3936(7) | 10243(4) | 1483(3) | 114(2) |
| C23 | 2976(4) | 5287(3) | 1279(2) | 52(1) |
| C24 | 3430(4) | 4268(3) | 1339(2) | 58(1) |
| C25 | 3888(5) | 3708(3) | 612(3) | 74(1) |
| C26 | 3930(5) | 4100(3) | -145(3) | 79(2) |
| C27 | 3460(5) | 5113(3) | -199(2) | 68(1) |
| C28 | 2990(4) | 5709(3) | 508(2) | 53(1) |
| C29 | 2619(4) | 6776(3) | 421(2) | 57(1) |
| C30 | -1009(4) | 9090(3) | 2110(2) | 47(1) |
| C31 | -2266(4) | 9796(3) | 2536(2) | 53(1) |
| C32 | -3040(4) | 10324(3) | 2071(3) | 67(1) |
| C33 | -2629(5) | 10225(3) | 1217(3) | 74(1) |
| C34 | -1389(4) | 9558(3) | 803(2) | 59(1) |
| C35 | -565(4) | 9008(3) | 1233(2) | 47(1) |
| C36 | 800(4) | 8371(3) | 757(2) | 59(1) |
| C37 | 3336(6) | 3778(3) | 2183(3) | 77(2) |
| C38 | 3969(7) | 2663(3) | 2081(3) | 118(2) |
| C39 | 4061(6) | 4099(4) | 2645(3) | 99(2) |
| C40 | 1873(6) | 4067(4) | 2696(3) | 92(2) |
| C41 | -2724(5) | 9971(3) | 3496(2) | 62(1) |
| C42 | -4078(5) | 10812(4) | 3802(3) | 94(2) |
| C43 | -1721(5) | 10252(4) | 3715(3) | 82(2) |
| C44 | -2882(5) | 9055(3) | 3942(3) | 81(2) |

*Figure 26*--Bond lengths [Å] and angles [°] for 8

| | | | | | |
|---|---|---|---|---|---|
| Mo1-O1 | 1.979(3) | C41-C42 | 1.549(6) | C16-C15-C18 | 107.4(4) |
| Mo1-O4 | 1.986(3) | | | C17-C15-C18 | 106.0(4) |
| Mo1-O2 | 1.992(3) | O1-Mo1-O4 | 90.24(12) | C22-C19-C20 | 107.1(4) |
| Mo1-O3 | 1.997(3) | O1-Mo1-O2 | 177.12(10) | C22-C19-C9 | 111.8(4) |
| Mo1-N1 | 2.186(3) | O4-Mo1-O2 | 88.73(12) | C20-C19-C9 | 110.7(4) |
| Mo1-N2 | 2.191(3) | O1-Mo1-O3 | 88.60(12) | C22-C19-C21 | 107.7(4) |
| O1-C1 | 1.364(4) | O4-Mo1-O3 | 177.26(10) | C20-C19-C21 | 112.1(4) |
| O2-C8 | 1.366(5) | O2-Mo1-O3 | 92.55(12) | C9-C19-C21 | 107.5(3) |
| O3-C23 | 1.357(4) | O1-Mo1-N1 | 89.42(11) | O3-C23-C28 | 118.7(4) |
| O4-C30 | 1.359(4) | O4-Mo1-N1 | 88.58(11) | O3-C23-C24 | 120.8(3) |
| N1-C7 | 1.476(5) | O2-Mo1-N1 | 87.86(11) | C28-C23-C24 | 120.5(4) |
| N1-C14 | 1.503(5) | O3-Mo1-N1 | 93.89(12) | C25-C24-C23 | 117.4(4) |
| N2-C36 | 1.482(5) | O1-Mo1-N2 | 89.06(11) | C25-C24-C37 | 120.4(4) |
| N2-C29 | 1.535(5) | O4-Mo1-N2 | 89.21(10) | C23-C24-C37 | 122.1(4) |
| C1-C6 | 1.415(6) | O2-Mo1-N2 | 93.61(11) | C26-C25-C24 | 123.1(4) |
| C1-C2 | 1.418(6) | O3-Mo1-N2 | 88.29(10) | C25-C26-C27 | 119.2(4) |
| C2-C3 | 1.400(5) | N1-Mo1-N2 | 177.32(12) | C28-C27-C26 | 120.2(4) |
| C2-C15 | 1.521(6) | C1-O1-Mo1 | 131.7(3) | C27-C28-C23 | 119.5(4) |
| C3-C4 | 1.386(7) | C8-O2-Mo1 | 131.7(2) | C27-C28-C29 | 119.0(4) |
| C4-C5 | 1.360(7) | C23-O3-Mo1 | 131.2(2) | C23-C28-C29 | 121.2(3) |
| C5-C6 | 1.393(6) | C30-O4-Mo1 | 131.6(2) | C28-C29-N2 | 111.9(3) |
| C6-C7 | 1.521(6) | C7-N1-C14 | 110.2(3) | O4-C30-C35 | 120.1(3) |
| C8-C9 | 1.407(5) | C7-N1-Mo1 | 113.2(3) | O4-C30-C31 | 120.4(3) |
| C8-C13 | 1.418(5) | C14-N1-Mo1 | 110.3(2) | C35-C30-C31 | 119.5(3) |
| C9-C10 | 1.404(6) | C36-N2-C29 | 109.8(3) | C32-C31-C30 | 117.7(4) |
| C9-C19 | 1.546(5) | C36-N2-Mo1 | 111.4(2) | C32-C31-C41 | 121.8(4) |
| C10-C11 | 1.384(6) | C29-N2-Mo1 | 108.6(2) | C30-C31-C41 | 120.5(4) |
| C11-C12 | 1.383(6) | O1-C1-C6 | 119.5(4) | C31-C32-C33 | 123.0(4) |
| C12-C13 | 1.383(6) | O1-C1-C2 | 119.9(4) | C32-C33-C34 | 119.1(4) |
| C13-C14 | 1.490(6) | C6-C1-C2 | 120.6(4) | C35-C34-C33 | 120.7(4) |
| C15-C16 | 1.524(6) | C3-C2-C1 | 116.9(4) | C34-C35-C30 | 119.8(4) |
| C15-C17 | 1.543(6) | C3-C2-C15 | 121.5(5) | C34-C35-C36 | 118.7(3) |
| C15-C18 | 1.550(6) | C1-C2-C15 | 121.5(4) | C30-C35-C36 | 121.4(3) |
| C19-C22 | 1.534(6) | C4-C3-C2 | 122.2(5) | N2-C36-C35 | 116.0(3) |
| C19-C20 | 1.545(6) | C5-C4-C3 | 119.8(5) | C40-C37-C38 | 108.6(5) |
| C19-C21 | 1.564(7) | C4-C5-C6 | 121.4(5) | C40-C37-C39 | 110.5(4) |
| C23-C28 | 1.414(5) | C5-C6-C1 | 118.6(5) | C38-C37-C39 | 106.7(4) |
| C23-C24 | 1.415(5) | C5-C6-C7 | 119.1(4) | C40-C37-C24 | 108.0(4) |
| C24-C25 | 1.393(6) | C1-C6-C7 | 122.3(4) | C38-C37-C24 | 112.2(4) |
| C24-C37 | 1.554(6) | N1-C7-C6 | 115.5(4) | C39-C37-C24 | 110.8(4) |
| C25-C26 | 1.372(6) | O2-C8-C9 | 120.8(3) | C43-C41-C44 | 111.4(4) |
| C26-C27 | 1.405(6) | O2-C8-C13 | 118.9(4) | C43-C41-C42 | 108.2(4) |
| C27-C28 | 1.392(5) | C9-C8-C13 | 120.3(4) | C44-C41-C42 | 107.2(4) |
| C28-C29 | 1.491(5) | C10-C9-C8 | 117.4(4) | C43-C41-C31 | 109.1(4) |
| C30-C35 | 1.420(5) | C10-C9-C19 | 120.0(4) | C44-C41-C31 | 110.2(3) |
| C30-C31 | 1.428(5) | C8-C9-C19 | 122.5(4) | C42-C41-C31 | 110.7(4) |
| C31-C32 | 1.381(6) | C11-C10-C9 | 122.7(4) | | |
| C31-C41 | 1.567(5) | C12-C11-C10 | 118.6(5) | | |
| C32-C33 | 1.384(6) | C11-C12-C13 | 121.5(4) | | |
| C33-C34 | 1.389(6) | C12-C13-C8 | 119.3(4) | | |
| C34-C35 | 1.384(5) | C12-C13-C14 | 119.4(4) | | |
| C35-C36 | 1.490(5) | C8-C13-C14 | 121.2(4) | | |
| C37-C40 | 1.539(7) | C13-C14-N1 | 112.8(4) | | |
| C37-C38 | 1.543(6) | C2-C15-C16 | 110.1(4) | | |
| C37-C39 | 1.544(7) | C2-C15-C17 | 110.6(4) | | |
| C41-C43 | 1.538(6) | C16-C15-C17 | 110.6(4) | | |
| C41-C44 | 1.548(6) | C2-C15-C18 | 112.1(4) | | |

*Figure 27*--Anisotropic *displacement parameters ($Å^2 \times 10^3$) for 8*

The anisotropic displacement factor exponent takes the form: $-2\pi^2[\ h^2\ a^{*2}U^{11} + ... + 2\ h\ k\ a^*\ b^*\ U^{12}\ ]$

| | $U^{11}$ | $U^{22}$ | $U^{33}$ | $U^{23}$ | $U^{13}$ | $U^{12}$ |
|---|---|---|---|---|---|---|
| Mo1 | 53(1) | 44(1) | 29(1) | 8(1) | -15(1) | -14(1) |
| O1 | 58(2) | 56(2) | 36(1) | 7(1) | -13(1) | -22(2) |
| O2 | 60(2) | 51(2) | 39(1) | 6(1) | -17(1) | -20(1) |
| O3 | 57(2) | 49(2) | 43(1) | 5(1) | -21(1) | -14(1) |
| O4 | 59(2) | 54(2) | 37(1) | 4(1) | -18(1) | -14(1) |
| N1 | 53(2) | 73(2) | 37(2) | 20(2) | -18(2) | -33(2) |
| N2 | 50(2) | 42(2) | 31(2) | 5(1) | -6(1) | -1(2) |
| C1 | 60(3) | 59(3) | 44(2) | 9(2) | -14(2) | -28(2) |
| C2 | 68(3) | 71(3) | 49(2) | 8(2) | -17(2) | -32(3) |
| C3 | 79(4) | 144(5) | 56(3) | 11(3) | -13(3) | -63(4) |
| C4 | 111(5) | 185(7) | 52(3) | 21(3) | -7(3) | -87(5) |
| C5 | 100(4) | 142(5) | 42(3) | 20(3) | -20(3) | -69(4) |
| C6 | 78(3) | 82(3) | 41(2) | 18(2) | -21(2) | -41(3) |
| C7 | 93(4) | 84(3) | 36(2) | 21(2) | -24(2) | -41(3) |
| C8 | 52(3) | 54(2) | 39(2) | 3(2) | -10(2) | -18(2) |
| C9 | 61(3) | 55(3) | 51(2) | 3(2) | -19(2) | -22(2) |
| C10 | 89(4) | 72(3) | 56(3) | 2(2) | -22(3) | -41(3) |
| C11 | 100(4) | 101(4) | 57(3) | -3(3) | -27(3) | -55(4) |
| C12 | 87(4) | 104(4) | 41(2) | 8(2) | -23(2) | -43(3) |
| C13 | 62(3) | 65(3) | 33(2) | -1(2) | -17(2) | -23(2) |
| C14 | 76(3) | 69(3) | 41(2) | 18(2) | -27(2) | -25(3) |
| C15 | 68(3) | 73(3) | 54(3) | 9(2) | -23(2) | -30(3) |
| C16 | 100(4) | 79(4) | 67(3) | 0(3) | -36(3) | -33(3) |
| C17 | 89(4) | 80(4) | 83(3) | 21(3) | -49(3) | -33(3) |
| C18 | 93(4) | 151(6) | 87(4) | 29(4) | -44(3) | -69(4) |
| C19 | 78(3) | 64(3) | 60(3) | 15(2) | -25(2) | -44(3) |
| C20 | 89(4) | 97(4) | 47(2) | 11(2) | -14(2) | -40(3) |
| C21 | 97(4) | 65(3) | 87(3) | 18(3) | -39(3) | -25(3) |
| C22 | 185(7) | 116(5) | 97(4) | 48(3) | -64(4) | -109(5) |
| C23 | 54(3) | 54(3) | 38(2) | 3(2) | -15(2) | -10(2) |
| C24 | 60(3) | 54(3) | 54(2) | 4(2) | -19(2) | -16(2) |
| C25 | 83(4) | 52(3) | 73(3) | -3(2) | -23(3) | -10(3) |
| C26 | 100(4) | 63(3) | 63(3) | -12(2) | -32(3) | -10(3) |
| C27 | 75(3) | 73(3) | 42(2) | -8(2) | -20(2) | -10(3) |
| C28 | 51(3) | 49(2) | 46(2) | 2(2) | -13(2) | -5(2) |
| C29 | 59(3) | 56(3) | 39(2) | 8(2) | -9(2) | -10(2) |
| C30 | 55(3) | 43(2) | 40(2) | 8(2) | -19(2) | -15(2) |
| C31 | 57(3) | 43(2) | 51(2) | 1(2) | -16(2) | -10(2) |
| C32 | 57(3) | 66(3) | 58(3) | 4(2) | -19(2) | -1(2) |
| C33 | 77(3) | 67(3) | 70(3) | 20(2) | -39(3) | -6(3) |
| C34 | 69(3) | 59(3) | 44(2) | 12(2) | -26(2) | -14(2) |
| C35 | 55(3) | 44(2) | 37(2) | 7(2) | -14(2) | -16(2) |
| C36 | 70(3) | 53(3) | 34(2) | 10(2) | -11(2) | -9(2) |
| C37 | 107(4) | 45(3) | 68(3) | 15(2) | -38(3) | -10(3) |
| C38 | 173(7) | 48(3) | 113(4) | 23(3) | -59(4) | -12(4) |
| C39 | 133(5) | 76(4) | 84(3) | 19(3) | -66(4) | -11(4) |
| C40 | 116(5) | 83(4) | 66(3) | 26(3) | -13(3) | -42(4) |
| C41 | 66(3) | 58(3) | 43(2) | -1(2) | -8(2) | -9(2) |
| C42 | 85(4) | 86(4) | 69(3) | -18(3) | -6(3) | 1(3) |
| C43 | 107(4) | 94(4) | 51(3) | -9(2) | -25(3) | -40(4) |
| C44 | 91(4) | 79(4) | 55(3) | 10(2) | -6(3) | -29(3) |

12

*Figure 41*-- *Crystal data and structure refinement for 12*

| | |
|---|---|
| Identification code | orei33 |
| Empirical formula | C34 H29 F12 N O2 W |
| Formula weight | 895.43 |
| Temperature | 100(2) K |
| Wavelength | 0.71073 Å |
| Crystal system | Monoclinic |
| Space group | P21/c |
| Unit cell dimensions | a = 10.6462(5) Å    α= 90°. |
| | b = 15.7072(7) Å    β= 95.374(1)°. |
| | c = 19.9882(9) Å    γ =90°. |
| Volume | 3327.8(3) Å$^3$ |
| Z | 4 |
| Density (calculated) | 1.787 Mg/m$^3$ |
| Absorption coefficient | 3.571 mm$^{-1}$ |
| F(000) | 1752 |
| Crystal size | 0.29 x 0.17 x 0.05 mm$^3$ |
| Theta range for data collection | 1.65 to 27.50°. |
| Index ranges | -13≤h≤13, -20≤k≤20, -25≤l≤25 |
| Reflections collected | 104900 |
| Independent reflections | 7644 [R(int) = 0.0372] |
| Completeness to theta = 27.50° | 100.0 % |
| Absorption correction | Integration |
| Max. and min. transmission | 0.8388 and 0.4230 |
| Refinement method | Full-matrix least-squares on F$^2$ |
| Data / restraints / parameters | 7644 / 0 / 457 |
| Goodness-of-fit on F$^2$ | 1.051 |
| Final R indices [I>2sigma(I)] | R1 = 0.0145, wR2 = 0.0369 [6905] |
| R indices (all data) | R1 = 0.0178, wR2 = 0.0376 |
| Largest diff. peak and hole | 0.827 and -0.431 e.Å$^{-3}$ |

$R1 = \Sigma(||F_o| - |F_c||) / \Sigma|F_o|$
$wR2 = [\Sigma[w(F_o^2 - F_c^2)^2] / \Sigma[w(F_o^2)^2]]^{1/2}$
$S = [\Sigma[w(F_o^2 - F_c^2)^2] / (n-p)]^{1/2}$
$w = 1/[\sigma^2(F_o^2) + (m*p)^2 + n*p], p = [max(F_o^2, 0) + 2*F_c^2]/3$, m & n are constants.

*Figure 42* -- *Atomic coordinates (x $10^4$) and equivalent isotropic displacement parameters ($Å^2$ x $10^3$) for 12*

U(eq) is defined as one third of the trace of the orthogonalized $U^{ij}$ tensor.

|  | x | y | z | U(eq) |
|---|---|---|---|---|
| W1 | 8673(1) | 598(1) | 7892(1) | 11(1) |
| F1 | 7832(1) | -1208(1) | 6441(1) | 32(1) |
| F2 | 8375(1) | -2040(1) | 7270(1) | 28(1) |
| F3 | 6512(1) | -2135(1) | 6766(1) | 36(1) |
| F4 | 6882(1) | -2032(1) | 8278(1) | 28(1) |
| F5 | 5113(1) | -1625(1) | 7770(1) | 32(1) |
| F6 | 6092(1) | -823(1) | 8517(1) | 27(1) |
| F7 | 8904(1) | 2190(1) | 9782(1) | 24(1) |
| F8 | 10130(1) | 2773(1) | 9122(1) | 26(1) |
| F9 | 8534(1) | 3467(1) | 9412(1) | 25(1) |
| F10 | 9046(1) | 3305(1) | 7921(1) | 27(1) |
| F11 | 7195(1) | 3603(1) | 8206(1) | 23(1) |
| F12 | 7438(1) | 2605(1) | 7491(1) | 21(1) |
| O1 | 8067(1) | -570(1) | 7793(1) | 15(1) |
| O2 | 8856(1) | 1626(1) | 8453(1) | 15(1) |
| N1 | 6835(1) | 861(1) | 7957(1) | 13(1) |
| C1 | 6965(2) | -903(1) | 7468(1) | 15(1) |
| C2 | 6095(2) | -235(1) | 7109(1) | 13(1) |
| C3 | 6036(2) | 584(1) | 7386(1) | 13(1) |
| C4 | 5202(2) | 1178(1) | 7062(1) | 14(1) |
| C5 | 4463(2) | 974(1) | 6482(1) | 15(1) |
| C6 | 4521(2) | 166(1) | 6194(1) | 15(1) |
| C7 | 5329(2) | -424(1) | 6517(1) | 15(1) |
| C8 | 7423(2) | -1581(1) | 6980(1) | 23(1) |
| C9 | 6256(2) | -1353(1) | 8010(1) | 21(1) |
| C10 | 3713(2) | -54(1) | 5556(1) | 20(1) |
| C11 | 8117(2) | 2293(1) | 8633(1) | 15(1) |
| C12 | 6823(2) | 1997(1) | 8808(1) | 13(1) |
| C13 | 6242(2) | 1309(1) | 8456(1) | 13(1) |
| C14 | 5050(2) | 1043(1) | 8618(1) | 15(1) |
| C15 | 4448(2) | 1443(1) | 9114(1) | 17(1) |
| C16 | 5014(2) | 2125(1) | 9471(1) | 18(1) |
| C17 | 6188(2) | 2393(1) | 9309(1) | 17(1) |
| C18 | 8924(2) | 2690(1) | 9241(1) | 20(1) |
| C19 | 7953(2) | 2959(1) | 8059(1) | 18(1) |
| C20 | 4356(2) | 2569(1) | 10010(1) | 28(1) |
| C21 | 9510(2) | 830(1) | 7111(1) | 15(1) |
| C22 | 9449(2) | 1152(1) | 6394(1) | 19(1) |
| C23 | 8051(2) | 1245(1) | 6143(1) | 24(1) |
| C24 | 10067(2) | 516(1) | 5947(1) | 35(1) |
| C25 | 10080(2) | 2033(1) | 6374(1) | 31(1) |
| C26 | 10556(2) | 552(1) | 7576(1) | 16(1) |
| C27 | 11910(2) | 610(1) | 7410(1) | 22(1) |
| C28 | 10325(2) | 268(1) | 8256(1) | 15(1) |
| C29 | 11243(2) | 60(1) | 8818(1) | 18(1) |
| C30 | 12231(2) | -520(1) | 8764(1) | 26(1) |
| C31 | 13060(2) | -703(1) | 9321(1) | 32(1) |
| C32 | 12921(2) | -314(1) | 9931(1) | 32(1) |
| C33 | 11938(2) | 250(1) | 9992(1) | 29(1) |
| C34 | 11096(2) | 435(1) | 9438(1) | 22(1) |

*Figure 43*-- *Bond lengths [Å] and angles [°] for* 12

| | | | | | |
|---|---|---|---|---|---|
| W1-C21 | 1.9046(16) | C21-W1-C28 | 83.09(7) | C13-C12-C17 | 118.71(15) |
| W1-C28 | 1.9106(18) | C21-W1-O1 | 105.78(6) | C13-C12-C11 | 119.03(14) |
| W1-O1 | 1.9489(11) | C28-W1-O1 | 93.85(6) | C17-C12-C11 | 122.26(15) |
| W1-O2 | 1.9631(11) | C21-W1-O2 | 106.38(6) | C14-C13-C12 | 118.67(15) |
| W1-N1 | 2.0158(14) | C28-W1-O2 | 88.15(6) | C14-C13-N1 | 119.17(15) |
| W1-C26 | 2.1589(18) | O1-W1-O2 | 147.78(5) | C12-C13-N1 | 122.14(15) |
| F1-C8 | 1.335(2) | C21-W1-N1 | 122.99(7) | C15-C14-C13 | 121.41(16) |
| F2-C8 | 1.331(2) | C28-W1-N1 | 153.60(6) | C14-C15-C16 | 120.66(16) |
| F3-C8 | 1.343(2) | O1-W1-N1 | 83.38(5) | C17-C16-C15 | 118.04(15) |
| F4-C9 | 1.342(2) | O2-W1-N1 | 80.83(5) | C17-C16-C20 | 121.02(17) |
| F5-C9 | 1.336(2) | C21-W1-C26 | 41.22(7) | C15-C16-C20 | 120.93(17) |
| F6-C9 | 1.336(2) | C28-W1-C26 | 41.90(7) | C16-C17-C12 | 122.50(16) |
| F7-C18 | 1.339(2) | O1-W1-C26 | 104.24(6) | F8-C18-F7 | 106.83(15) |
| F8-C18 | 1.334(2) | O2-W1-C26 | 98.61(6) | F8-C18-F9 | 106.42(14) |
| F9-C18 | 1.3435(19) | N1-W1-C26 | 163.57(6) | F7-C18-F9 | 107.32(13) |
| F10-C19 | 1.337(2) | C1-O1-W1 | 131.31(10) | F8-C18-C11 | 111.85(14) |
| F11-C19 | 1.3436(19) | C11-O2-W1 | 138.19(11) | F7-C18-C11 | 110.29(14) |
| F12-C19 | 1.335(2) | C13-N1-C3 | 116.32(14) | F9-C18-C11 | 113.77(15) |
| O1-C1 | 1.389(2) | C13-N1-W1 | 130.22(11) | F12-C19-F10 | 106.87(13) |
| O2-C11 | 1.3797(19) | C3-N1-W1 | 113.36(10) | F12-C19-F11 | 106.97(15) |
| N1-C13 | 1.417(2) | O1-C1-C2 | 114.02(13) | F10-C19-F11 | 106.87(13) |
| N1-C3 | 1.426(2) | O1-C1-C9 | 106.85(14) | F12-C19-C11 | 110.96(13) |
| C1-C2 | 1.533(2) | C2-C1-C9 | 109.08(14) | F10-C19-C11 | 112.80(15) |
| C1-C9 | 1.548(2) | O1-C1-C8 | 104.57(14) | F11-C19-C11 | 112.03(13) |
| C1-C8 | 1.552(2) | C2-C1-C8 | 112.85(14) | C26-C21-C22 | 132.01(15) |
| C2-C3 | 1.404(2) | C9-C1-C8 | 109.19(14) | C26-C21-W1 | 78.84(10) |
| C2-C7 | 1.404(2) | C3-C2-C7 | 118.82(15) | C22-C21-W1 | 149.07(14) |
| C3-C4 | 1.404(2) | C3-C2-C1 | 119.39(15) | C21-C22-C24 | 110.58(15) |
| C4-C5 | 1.377(2) | C7-C2-C1 | 121.78(15) | C21-C22-C23 | 107.23(14) |
| C5-C6 | 1.397(2) | C4-C3-C2 | 118.50(15) | C24-C22-C23 | 109.11(16) |
| C6-C7 | 1.383(2) | C4-C3-N1 | 118.07(14) | C21-C22-C25 | 110.19(15) |
| C6-C10 | 1.511(2) | C2-C3-N1 | 123.32(15) | C24-C22-C25 | 111.07(16) |
| C11-C12 | 1.525(2) | C5-C4-C3 | 121.35(15) | C23-C22-C25 | 108.54(16) |
| C11-C19 | 1.550(2) | C4-C5-C6 | 120.94(16) | C21-C26-C28 | 119.89(15) |
| C11-C18 | 1.551(2) | C7-C6-C5 | 117.82(16) | C21-C26-C27 | 122.13(16) |
| C12-C13 | 1.402(2) | C7-C6-C10 | 121.38(15) | C28-C26-C27 | 117.78(16) |
| C12-C17 | 1.404(2) | C5-C6-C10 | 120.79(15) | C21-C26-W1 | 59.94(9) |
| C13-C14 | 1.402(2) | C6-C7-C2 | 122.54(15) | C28-C26-W1 | 60.00(9) |
| C14-C15 | 1.382(2) | F2-C8-F1 | 107.27(16) | C27-C26-W1 | 173.09(13) |
| C15-C16 | 1.393(3) | F2-C8-F3 | 106.62(14) | C29-C28-C26 | 128.45(16) |
| C16-C17 | 1.386(2) | F1-C8-F3 | 107.86(15) | C29-C28-W1 | 151.93(13) |
| C16-C20 | 1.510(2) | F2-C8-C1 | 111.70(15) | C26-C28-W1 | 78.11(10) |
| C21-C26 | 1.450(3) | F1-C8-C1 | 110.52(14) | C34-C29-C30 | 119.29(17) |
| C21-C22 | 1.514(2) | F3-C8-C1 | 112.62(16) | C34-C29-C28 | 117.92(16) |
| C22-C24 | 1.531(3) | F6-C9-F5 | 106.99(15) | C30-C29-C28 | 122.75(17) |
| C22-C23 | 1.533(3) | F6-C9-F4 | 106.68(15) | C31-C30-C29 | 119.94(19) |
| C22-C25 | 1.540(3) | F5-C9-F4 | 106.91(14) | C32-C31-C30 | 120.3(2) |
| C26-C28 | 1.473(2) | F6-C9-C1 | 110.76(13) | C31-C32-C33 | 120.31(19) |
| C26-C27 | 1.512(2) | F5-C9-C1 | 112.46(15) | C32-C33-C34 | 119.92(19) |
| C28-C29 | 1.455(2) | F4-C9-C1 | 112.69(15) | C33-C34-C29 | 120.24(18) |
| C29-C34 | 1.394(3) | O2-C11-C12 | 112.18(13) | | |
| C29-C30 | 1.403(3) | O2-C11-C19 | 110.28(13) | | |
| C30-C31 | 1.385(3) | C12-C11-C19 | 109.54(14) | | |
| C31-C32 | 1.383(3) | O2-C11-C18 | 102.83(14) | | |
| C32-C33 | 1.386(3) | C12-C11-C18 | 112.89(13) | | |
| C33-C34 | 1.389(3) | C19-C11-C18 | 108.93(13) | | |

*Figure 44*-- Anisotropic displacement parameters ($Å^2 \times 10^3$) for I2

The anisotropic displacement factor exponent takes the form: $-2\pi^2[h^2 a^{*2}U^{11} + ... + 2 h k a^* b^* U^{12}]$

| Atm | U11 | U22 | U33 | U23 | U13 | U12 | Atm | U11 | U22 | U33 | U23 | U13 | U12 |
|---|---|---|---|---|---|---|---|---|---|---|---|---|---|
| W1 | 9(1) | 13(1) | 11(1) | -1(1) | 0(1) | 0(1) | C14 | 14(1) | 16(1) | 15(1) | 4(1) | 0(1) | 1(1) |
| F1 | 34(1) | 38(1) | 24(1) | -6(1) | 5(1) | 14(1) | C15 | 14(1) | 20(1) | 18(1) | 7(1) | 5(1) | 3(1) |
| F2 | 24(1) | 23(1) | 36(1) | -7(1) | -7(1) | 12(1) | C16 | 21(1) | 19(1) | 15(1) | 4(1) | 6(1) | 6(1) |
| F3 | 33(1) | 20(1) | 49(1) | -16(1) | -18(1) | 4(1) | C17 | 21(1) | 15(1) | 14(1) | 0(1) | 2(1) | 2(1) |
| F4 | 25(1) | 20(1) | 39(1) | 13(1) | 0(1) | 4(1) | C18 | 21(1) | 19(1) | 20(1) | -5(1) | 2(1) | -2(1) |
| F5 | 18(1) | 29(1) | 49(1) | 14(1) | -5(1) | -10(1) | C19 | 17(1) | 17(1) | 20(1) | 0(1) | 5(1) | -3(1) |
| F6 | 31(1) | 25(1) | 26(1) | 6(1) | 10(1) | 2(1) | C20 | 32(1) | 30(1) | 25(1) | -3(1) | 13(1) | 4(1) |
| F7 | 28(1) | 29(1) | 15(1) | -1(1) | -3(1) | -2(1) | C21 | 12(1) | 19(1) | 15(1) | -3(1) | 3(1) | -2(1) |
| F8 | 18(1) | 31(1) | 28(1) | -10(1) | 0(1) | -8(1) | C22 | 16(1) | 29(1) | 12(1) | 1(1) | 2(1) | -2(1) |
| F9 | 30(1) | 20(1) | 26(1) | -11(1) | 2(1) | -2(1) | C23 | 19(1) | 37(1) | 15(1) | 4(1) | 0(1) | -2(1) |
| F10 | 21(1) | 29(1) | 31(1) | 8(1) | 7(1) | -7(1) | C24 | 32(1) | 55(1) | 18(1) | -4(1) | 7(1) | 10(1) |
| F11 | 27(1) | 16(1) | 27(1) | 2(1) | 6(1) | 4(1) | C25 | 29(1) | 40(1) | 22(1) | 11(1) | -3(1) | -13(1) |
| F12 | 27(1) | 22(1) | 14(1) | 2(1) | 1(1) | -1(1) | C26 | 13(1) | 18(1) | 19(1) | -4(1) | 3(1) | -1(1) |
| O1 | 11(1) | 13(1) | 21(1) | -2(1) | -3(1) | 0(1) | C27 | 11(1) | 30(1) | 25(1) | 1(1) | 4(1) | 1(1) |
| O2 | 12(1) | 16(1) | 16(1) | -3(1) | 1(1) | -1(1) | C28 | 13(1) | 14(1) | 17(1) | -1(1) | 0(1) | 0(1) |
| N1 | 11(1) | 14(1) | 13(1) | -2(1) | 1(1) | 0(1) | C29 | 12(1) | 20(1) | 21(1) | 5(1) | -1(1) | -3(1) |
| C1 | 13(1) | 12(1) | 20(1) | -1(1) | -2(1) | 0(1) | C30 | 22(1) | 25(1) | 30(1) | 4(1) | -1(1) | 4(1) |
| C2 | 9(1) | 14(1) | 17(1) | 0(1) | 0(1) | -1(1) | C31 | 22(1) | 31(1) | 42(1) | 14(1) | -2(1) | 7(1) |
| C3 | 11(1) | 15(1) | 13(1) | 0(1) | 3(1) | -2(1) | C32 | 22(1) | 43(1) | 30(1) | 22(1) | -7(1) | -6(1) |
| C4 | 13(1) | 14(1) | 16(1) | 0(1) | 4(1) | -1(1) | C33 | 24(1) | 42(1) | 20(1) | 9(1) | -1(1) | -6(1) |
| C5 | 12(1) | 18(1) | 15(1) | 5(1) | 2(1) | 1(1) | C34 | 18(1) | 29(1) | 21(1) | 7(1) | 2(1) | -1(1) |
| C6 | 12(1) | 20(1) | 14(1) | 1(1) | 2(1) | -3(1) | | | | | | | |
| C7 | 14(1) | 15(1) | 17(1) | -2(1) | 1(1) | -2(1) | | | | | | | |
| C8 | 22(1) | 19(1) | 27(1) | -5(1) | -6(1) | 4(1) | | | | | | | |
| C9 | 16(1) | 16(1) | 30(1) | 6(1) | -3(1) | -1(1) | | | | | | | |
| C10 | 19(1) | 24(1) | 18(1) | 0(1) | -3(1) | -2(1) | | | | | | | |
| C11 | 16(1) | 14(1) | 13(1) | -2(1) | 1(1) | -2(1) | | | | | | | |
| C12 | 15(1) | 13(1) | 12(1) | 2(1) | 2(1) | 1(1) | | | | | | | |
| C13 | 13(1) | 13(1) | 11(1) | 2(1) | 2(1) | 3(1) | | | | | | | |

*Figure 48 - Crystal data and structure refinement for 16.*

| | |
|---|---|
| Identification code | souf3 |
| Empirical formula | $C_{56}H_{72}NO_4PW$ |
| Formula weight | 1037.97 |
| Temperature | 100(2) K |
| Wavelength | 0.71073 Å |
| Crystal system | Monoclinic |
| Space group | $P2_1/c$ |
| Unit cell dimensions | a = 17.0367(14) Å  α= 90°. |
| | b = 14.5660(12) Å  β= 105.866(2)°. |
| | c = 22.0816(18) Å  γ = 90°. |
| Volume | 5270.9(7) Å$^3$ |
| Z | 4 |
| Density (calculated) | 1.308 Mg/m$^3$ |
| Absorption coefficient | 2.265 mm$^{-1}$ |
| F(000) | 2144 |
| Crystal size | 0.15 x 0.04 x 0.01 mm$^3$ |
| Theta range for data collection | 1.70 to 27.50°. |
| Index ranges | $-22 \leq h \leq 21, -18 \leq k \leq 18, -27 \leq l \leq 28$ |
| Reflections collected | 56023 |
| Independent reflections | 12092 [R(int) = 0.0765] |
| Completeness to theta = 27.50° | 100.0 % |
| Absorption correction | None |
| Max. and min. transmission | 0.9799 and 0.7318 |
| Refinement method | Full-matrix least-squares on $F^2$ |
| Data / restraints / parameters | 12092 / 0 / 583 |
| Goodness-of-fit on $F^2$ | 1.008 |
| Final R indices [I>2sigma(I)] | R1 = 0.0347, wR2 = 0.0563 [8643] |
| R indices (all data) | R1 = 0.0686, wR2 = 0.0640 |
| Largest diff. peak and hole | 1.351 and -1.101 e.Å$^{-3}$ |

$R1 = \Sigma(||F_o| - |F_c||) / \Sigma |F_o|$ $wR2 = [\Sigma[w(F_o^2 - F_c^2)^2] / \Sigma[w(F_o^2)^2]]^{1/2}$ $S = [\Sigma[w(F_o^2 - F_c^2)^2] / (n-p)]^{1/2}$ $w = 1/[\sigma^2(F_o^2)+(m*p)^2+n*p]$, $p = [max(F_o^2, 0) + 2* F_c^2]/3$, m & n are constants.

Figure 49 - *Atomic coordinates (x $10^4$) and equivalent isotropic displacement parameters ($Å^2$ x $10^3$) for 16*

| Atom | X | Y | Z | U(eq) | Atom | X | Y | Z | U(eq) |
|---|---|---|---|---|---|---|---|---|---|
| W1 | 7847(1) | 7712(1) | 2352(1) | 15(1) | C25 | 8220(2) | 6356(2) | 3561(2) | 24(1) |
| O1 | 7831(1) | 8926(1) | 2718(1) | 17(1) | C26 | 8856(3) | 5620(3) | 3553(2) | 49(1) |
| O2 | 7419(1) | 6902(2) | 1626(1) | 16(1) | C27 | 7398(3) | 5895(3) | 3520(2) | 46(1) |
| O3 | 8771(1) | 8003(2) | 2071(1) | 22(1) | C28 | 8465(4) | 6909(3) | 4172(2) | 57(2) |
| N1 | 6562(2) | 7804(2) | 2290(1) | 14(1) | C29 | 8100(2) | 6981(2) | 3000(2) | 19(1) |
| C1 | 7485(2) | 9279(2) | 3149(2) | 15(1) | C30 | 9622(2) | 7892(2) | 2135(2) | 26(1) |
| C2 | 7933(2) | 9865(2) | 3632(2) | 16(1) | C31 | 9706(2) | 7534(2) | 1512(2) | 28(1) |
| C3 | 7514(2) | 10238(2) | 4033(1) | 17(1) | C32 | 10012(3) | 8846(3) | 2260(2) | 47(1) |
| C4 | 6698(2) | 10060(2) | 3967(2) | 18(1) | C33 | 9999(2) | 7238(3) | 2672(2) | 38(1) |
| C5 | 6277(2) | 9479(2) | 3496(1) | 17(1) | P1 | 4221(1) | 6323(1) | 3281(1) | 19(1) |
| C6 | 6659(2) | 9068(2) | 3080(1) | 14(1) | C40 | 4856(2) | 5753(2) | 2882(2) | 25(1) |
| C7 | 6197(2) | 8449(2) | 2591(1) | 15(1) | C41 | 4849(2) | 6911(2) | 3953(2) | 21(1) |
| C8 | 5354(2) | 8361(2) | 2375(2) | 17(1) | C42 | 5582(2) | 7281(3) | 3932(2) | 24(1) |
| C9 | 5191(2) | 7637(2) | 1944(1) | 18(1) | C43 | 6046(2) | 7779(3) | 4437(2) | 28(1) |
| C10 | 5936(2) | 7293(2) | 1904(1) | 15(1) | C44 | 5759(3) | 7924(3) | 4956(2) | 37(1) |
| C11 | 6067(2) | 6468(2) | 1562(1) | 15(1) | C45 | 5028(3) | 7557(3) | 4976(2) | 51(1) |
| C12 | 5414(2) | 5864(2) | 1323(1) | 18(1) | C46 | 4571(3) | 7043(3) | 4476(2) | 44(1) |
| C13 | 5514(2) | 5096(2) | 985(2) | 19(1) | C51 | 3574(2) | 5516(3) | 3523(2) | 25(1) |
| C14 | 6272(2) | 4899(2) | 904(1) | 17(1) | C52 | 3877(3) | 4667(3) | 3760(2) | 35(1) |
| C15 | 6947(2) | 5460(2) | 1138(1) | 15(1) | C53 | 3374(3) | 4063(3) | 3967(2) | 45(1) |
| C16 | 6821(2) | 6270(2) | 1458(1) | 15(1) | C54 | 2595(3) | 4295(3) | 3943(2) | 49(1) |
| C17 | 8835(2) | 10067(2) | 3710(2) | 19(1) | C55 | 2287(3) | 5139(4) | 3701(2) | 55(1) |
| C18 | 9335(2) | 9176(2) | 3862(2) | 24(1) | C56 | 2777(3) | 5750(3) | 3488(2) | 40(1) |
| C19 | 8945(2) | 10503(2) | 3103(2) | 24(1) | C61 | 3597(2) | 7145(2) | 2769(2) | 19(1) |
| C20 | 9190(2) | 10738(2) | 4250(2) | 26(1) | C62 | 3147(2) | 6868(2) | 2171(2) | 24(1) |
| C21 | 7784(2) | 5233(2) | 1041(2) | 18(1) | C63 | 2666(2) | 7496(2) | 1768(2) | 28(1) |
| C22 | 7999(2) | 5945(2) | 599(2) | 22(1) | C64 | 2624(2) | 8400(3) | 1958(2) | 30(1) |
| C23 | 7797(2) | 4276(2) | 754(2) | 24(1) | C65 | 3067(2) | 8676(3) | 2555(2) | 30(1) |
| C24 | 8440(2) | 5222(2) | 1678(2) | 24(1) | C66 | 3551(2) | 8053(2) | 2960(2) | 24(1) |

U(eq) is defined as one third of the trace of the orthogonalized $U^{ij}$ tensor.

*Figure 50- Bond lengths [Å] for 16*

| Bond | Length | Bond | Length |
|---|---|---|---|
| W1-C29 | 1.741(3) | C21-C23 | 1.534(4) |
| W1-O3 | 1.891(2) | C21-C22 | 1.536(5) |
| W1-O1 | 1.948(2) | C21-C24 | 1.539(4) |
| W1-O2 | 1.963(2) | C25-C29 | 1.506(5) |
| W1-N1 | 2.161(3) | C25-C26 | 1.527(5) |
| O1-C1 | 1.350(4) | C25-C28 | 1.528(5) |
| O2-C16 | 1.348(4) | C25-C27 | 1.533(6) |
| O3-C30 | 1.427(4) | C30-C31 | 1.514(5) |
| N1-C10 | 1.387(4) | C30-C33 | 1.521(5) |
| N1-C7 | 1.391(4) | C30-C32 | 1.532(5) |
| C1-C6 | 1.407(5) | P1-C40 | 1.778(4) |
| C1-C2 | 1.416(4) | P1-C61 | 1.784(3) |
| C2-C3 | 1.391(5) | P1-C51 | 1.790(4) |
| C2-C17 | 1.528(5) | P1-C41 | 1.792(3) |
| C3-C4 | 1.381(5) | C41-C42 | 1.374(5) |
| C4-C5 | 1.381(4) | C41-C46 | 1.376(5) |
| C5-C6 | 1.396(4) | C42-C43 | 1.382(5) |
| C6-C7 | 1.462(4) | C43-C44 | 1.379(5) |
| C7-C8 | 1.389(4) | C44-C45 | 1.368(6) |
| C8-C9 | 1.398(4) | C45-C46 | 1.382(5) |
| C9-C10 | 1.390(4) | C51-C56 | 1.382(6) |
| C10-C11 | 1.468(5) | C51-C52 | 1.386(5) |
| C11-C16 | 1.397(5) | C52-C53 | 1.391(6) |
| C11-C12 | 1.402(4) | C53-C54 | 1.357(7) |
| C12-C13 | 1.381(5) | C54-C55 | 1.385(6) |
| C13-C14 | 1.381(5) | C55-C56 | 1.387(6) |
| C14-C15 | 1.391(4) | C61-C62 | 1.393(4) |
| C15-C16 | 1.420(5) | C61-C66 | 1.396(4) |
| C15-C21 | 1.535(5) | C62-C63 | 1.379(5) |
| C17-C20 | 1.533(4) | C63-C64 | 1.389(5) |
| C17-C18 | 1.539(5) | C64-C65 | 1.387(5) |
| C17-C19 | 1.540(5) | C65-C66 | 1.379(5) |

Symmetry transformations used to generate equivalent atoms

*Figure 51 Bond angles [°] for 16*

| Bond | Angle | Bond | Angle | Bond | Angle |
|---|---|---|---|---|---|
| C29-W1-O3 | 111.42(13) | C16-C11-C12 | 118.6(3) | C31-C30-C32 | 109.4(3) |
| C29-W1-O1 | 104.02(12) | C16-C11-C10 | 122.0(3) | C33-C30-C32 | 111.0(3) |
| O3-W1-O1 | 92.33(9) | C12-C11-C10 | 119.4(3) | C40-P1-C61 | 109.70(16) |
| C29-W1-O2 | 104.91(12) | C13-C12-C11 | 120.6(3) | C40-P1-C51 | 110.39(18) |
| O3-W1-O2 | 91.35(9) | C14-C13-C12 | 119.8(3) | C61-P1-C51 | 108.73(17) |
| O1-W1-O2 | 147.15(9) | C13-C14-C15 | 122.4(3) | C40-P1-C41 | 109.13(18) |
| C29-W1-N1 | 96.26(13) | C14-C15-C16 | 116.8(3) | C61-P1-C41 | 108.77(16) |
| O3-W1-N1 | 152.32(10) | C14-C15-C21 | 121.8(3) | C51-P1-C41 | 110.10(16) |
| O1-W1-N1 | 80.8(1) | C16-C15-C21 | 121.3(3) | C42-C41-C46 | 119.8(3) |
| O2-W1-N1 | 80.91(9) | O2-C16-C11 | 118.2(3) | C42-C41-P1 | 120.2(3) |
| C1-O1-W1 | 134.2(2) | O2-C16-C15 | 120.0(3) | C46-C41-P1 | 119.9(3) |
| C16-O2-W1 | 136.0(2) | C11-C16-C15 | 121.6(3) | C41-C42-C43 | 120.2(3) |
| C30-O3-W1 | 148.9(2) | C2-C17-C20 | 112.4(3) | C44-C43-C42 | 119.8(4) |
| C10-N1-C7 | 106.7(3) | C2-C17-C18 | 109.9(3) | C45-C44-C43 | 120.0(3) |
| C10-N1-W1 | 126.9(2) | C20-C17-C18 | 106.9(3) | C44-C45-C46 | 120.3(4) |
| C7-N1-W1 | 126.1(2) | C2-C17-C19 | 109.9(3) | C41-C46-C45 | 119.9(4) |
| O1-C1-C6 | 117.2(3) | C20-C17-C19 | 107.4(3) | C56-C51-C52 | 120.1(4) |
| O1-C1-C2 | 120.7(3) | C18-C17-C19 | 110.3(3) | C56-C51-P1 | 119.8(3) |
| C6-C1-C2 | 122.0(3) | C23-C21-C15 | 111.9(3) | C52-C51-P1 | 120.1(3) |
| C3-C2-C1 | 116.7(3) | C23-C21-C22 | 108.5(3) | C51-C52-C53 | 119.3(4) |
| C3-C2-C17 | 121.9(3) | C15-C21-C22 | 109.6(3) | C54-C53-C52 | 120.9(4) |
| C1-C2-C17 | 121.3(3) | C23-C21-C24 | 106.3(3) | C53-C54-C55 | 120.0(4) |
| C4-C3-C2 | 122.4(3) | C15-C21-C24 | 110.1(3) | C54-C55-C56 | 120.1(5) |
| C3-C4-C5 | 119.7(3) | C22-C21-C24 | 110.4(3) | C51-C56-C55 | 119.7(4) |
| C4-C5-C6 | 121.2(3) | C29-C25-C26 | 110.6(3) | C62-C61-C66 | 119.9(3) |
| C5-C6-C1 | 117.9(3) | C29-C25-C28 | 110.5(3) | C62-C61-P1 | 119.0(3) |
| C5-C6-C7 | 119.8(3) | C26-C25-C28 | 110.9(3) | C66-C61-P1 | 121.1(2) |
| C1-C6-C7 | 122.3(3) | C29-C25-C27 | 107.5(3) | C63-C62-C61 | 119.7(3) |
| C8-C7-N1 | 109.2(3) | C26-C25-C27 | 109.4(3) | C62-C63-C64 | 120.3(3) |
| C8-C7-C6 | 127.4(3) | C28-C25-C27 | 107.8(4) | C65-C64-C63 | 120.1(3) |
| N1-C7-C6 | 123.3(3) | C25-C29-W1 | 173.5(3) | C66-C65-C64 | 119.9(3) |
| C7-C8-C9 | 107.3(3) | O3-C30-C31 | 107.2(3) | C65-C66-C61 | 120.1(3) |
| C10-C9-C8 | 107.5(3) | O3-C30-C33 | 110.4(3) | C72-O4-C73 | 111.4(4) |
| N1-C10-C9 | 109.2(3) | C31-C30-C33 | 111.6(3) | O4-C72-C71 | 109.1(4) |
| N1-C10-C11 | 123.9(3) | O3-C30-C32 | 107.0(3) | O4-C73-C74 | 107.9(4) |
| C9-C10-C11 | 126.6(3) | | | | |

Symmetry transformations used to generate equivalent atoms

*Figure 52 – Anisotropic displacement parameters ($Å^2 \times 10^3$) for 16*

The anisotropic displacement factor exponent takes the form: $-2\pi^2[h^2 a^{*2}U^{11} + \ldots + 2 h k a^* b^* U^{12}]$

| Atm | $U^{11}$ | $U^{22}$ | $U^{33}$ | $U^{23}$ | $U^{13}$ | $U^{12}$ | Atm | $U^{11}$ | $U^{22}$ | $U^{33}$ | $U^{23}$ | $U^{13}$ | $U^{12}$ |
|---|---|---|---|---|---|---|---|---|---|---|---|---|---|
| W1 | 10(1) | 15(1) | 18(1) | -3(1) | 4(1) | 0(1) | C25 | 30(2) | 20(2) | 22(2) | 0(2) | 3(2) | 5(2) |
| O1 | 15(1) | 14(1) | 25(1) | -2(1) | 10(1) | -3(1) | C26 | 53(3) | 46(3) | 50(3) | 24(2) | 18(2) | 22(2) |
| O2 | 12(1) | 18(1) | 20(1) | -4(1) | 4(1) | -2(1) | C27 | 44(3) | 35(3) | 62(3) | 15(2) | 23(2) | -3(2) |
| O3 | 14(1) | 23(1) | 31(1) | -6(1) | 9(1) | 0(1) | C28 | 106(5) | 40(3) | 21(2) | 4(2) | 9(2) | -9(3) |
| N1 | 11(1) | 14(1) | 16(1) | 0(1) | 4(1) | -2(1) | C29 | 11(2) | 17(2) | 30(2) | -6(1) | 6(2) | 0(1) |
| C1 | 16(2) | 12(2) | 17(2) | 1(1) | 8(1) | 2(1) | C30 | 14(2) | 27(2) | 40(2) | -9(2) | 13(2) | -1(2) |
| C2 | 17(2) | 14(2) | 18(2) | 4(1) | 4(1) | 0(1) | C31 | 25(2) | 28(2) | 36(2) | -4(2) | 15(2) | 1(2) |
| C3 | 20(2) | 18(2) | 12(2) | 2(1) | 2(1) | 1(2) | C32 | 26(2) | 45(3) | 79(3) | -31(2) | 28(2) | -16(2) |
| C4 | 19(2) | 21(2) | 15(2) | 0(1) | 8(2) | 3(2) | C33 | 17(2) | 62(3) | 35(2) | -8(2) | 8(2) | 9(2) |
| C5 | 13(2) | 20(2) | 18(2) | 5(1) | 5(1) | 0(1) | P1 | 24(1) | 19(1) | 15(1) | -3(1) | 5(1) | -4(1) |
| C6 | 16(2) | 14(2) | 13(2) | 3(1) | 6(1) | 3(1) | C40 | 29(2) | 24(2) | 21(2) | -2(2) | 6(2) | 0(2) |
| C7 | 14(2) | 14(2) | 16(2) | 0(1) | 4(1) | 2(1) | C41 | 27(2) | 19(2) | 14(2) | 0(1) | 1(2) | -3(2) |
| C8 | 12(2) | 19(2) | 21(2) | 4(1) | 6(1) | 2(1) | C42 | 27(2) | 23(2) | 21(2) | -1(2) | 2(1) | 0(2) |
| C9 | 10(2) | 24(2) | 20(2) | 1(2) | 1(1) | -4(2) | C43 | 29(2) | 23(2) | 25(2) | 1(2) | -2(2) | -7(2) |
| C10 | 13(2) | 15(2) | 16(2) | 7(2) | 4(1) | -2(2) | C44 | 57(3) | 30(2) | 18(2) | -2(2) | 0(2) | -19(2) |
| C11 | 18(2) | 15(2) | 13(2) | 2(1) | 4(1) | 0(1) | C45 | 69(3) | 65(4) | 23(2) | -21(2) | 21(2) | -36(3) |
| C12 | 14(2) | 26(2) | 16(2) | 0(1) | 6(1) | -3(2) | C46 | 48(3) | 62(3) | 24(2) | -18(2) | 16(2) | -33(2) |
| C13 | 19(2) | 20(2) | 19(2) | -2(1) | 6(2) | -9(2) | C51 | 30(2) | 26(2) | 18(2) | -7(2) | 4(2) | -7(2) |
| C14 | 23(2) | 13(2) | 13(2) | 0(1) | 4(1) | -2(2) | C52 | 49(3) | 26(2) | 33(2) | 1(2) | 18(2) | -6(2) |
| C15 | 17(2) | 16(2) | 13(2) | 1(1) | 4(1) | 0(2) | C53 | 80(4) | 30(2) | 30(2) | -2(2) | 22(3) | -15(3) |
| C16 | 15(2) | 16(2) | 12(2) | 5(1) | -1(1) | -4(1) | C54 | 71(4) | 47(3) | 35(3) | -4(2) | 24(3) | -36(3) |
| C17 | 17(2) | 20(2) | 20(2) | -4(1) | 6(2) | -4(2) | C55 | 43(3) | 70(4) | 55(3) | 13(3) | 18(3) | -15(3) |
| C18 | 14(2) | 24(2) | 31(2) | -4(2) | 2(2) | 0(2) | C56 | 38(3) | 42(3) | 44(3) | 8(2) | 17(2) | -10(2) |
| C19 | 23(2) | 25(2) | 26(2) | -4(2) | 13(2) | -8(2) | C61 | 18(2) | 20(2) | 19(2) | -3(1) | 7(1) | -3(2) |
| C20 | 21(2) | 31(2) | 26(2) | -7(2) | 5(2) | -4(2) | C62 | 29(2) | 19(2) | 22(2) | -5(2) | 5(2) | -4(2) |
| C21 | 17(2) | 19(2) | 16(2) | -1(1) | 0(1) | 1(2) | C63 | 31(2) | 26(3) | 22(2) | -1(1) | -1(2) | -4(2) |
| C22 | 19(2) | 25(2) | 25(2) | -3(2) | 8(2) | 0(2) | C64 | 31(2) | 26(2) | 29(2) | 3(2) | 2(2) | 4(2) |
| C23 | 25(2) | 22(2) | 24(2) | -3(2) | 7(2) | 3(2) | C65 | 36(2) | 21(2) | 34(2) | -6(2) | 11(2) | 6(2) |
| C24 | 19(2) | 27(2) | 25(2) | 0(2) | 2(2) | 8(2) | C66 | 27(2) | 24(2) | 20(2) | -7(2) | 7(2) | -2(2) |

ONO PINCER LIGANDS AND ONO PINCER LIGAND COMPRISING METAL COMPLEXES

CROSS-REFERENCE TO RELATED APPLICATIONS

This application is a continuation-in-part of International Patent Application No. PCT/US2012/037302, filed May 10, 2012, which claims the benefit of U.S. Provisional Application Ser. No. 61/484,793, filed May 11, 2011, the disclosures of which are hereby incorporated by reference herein in their entirety, including any figures, tables, or drawings.

The subject invention was made with government support under the National Science Foundation, Contract No. CHE-0748408. The government has certain rights to this invention.

BACKGROUND OF INVENTION

Pincer ligands are chelating agents that bind metals tightly to three adjacent coplanar sites. The pincer-metal interaction is rigid and typically confers a high thermal stability to the ligand metal complexes. Organic portions and substituents define a hydrophobic pocket around the coordination site. These ligands traditionally share the common feature of a central aromatic unit. To this central unit are attached, in the ortho positions, two arms whose electronic and steric properties can be varied in many different ways. The ability to vary the properties of pincer ligands has been exploited for numerous complexes to be used as catalysts. Early work mainly focused on ligands where the central binding site is carbon and the peripheral binding sites are phosphorous, generally referred to by the atomic symbols of the donor atoms at the binding sites as the PCP systems. More recently CCC, CNC, CNS, NNN, NCN, PNP, OCO, SCS, SNS have been reported. Most frequently the pincer ligand transition metal complexes have been those of group VII-X metals where low coordinate and low oxidation state prevail and the metals are tolerant of a wide variety of substituents.

Early transition metal (group III-VI) pincer complexes are significantly less common and typically display high oxidation states and high coordination numbers, are typically electrophilic, and are intolerant of many functional groups. As most presently known pincer ligands have multiple soft donor atoms for metal binding, the ligands are not well suited to forming complexes with the early transition metals. Those that have been prepared include: pincer dicarbene complexes of CNC ligands with V, Ti, Cr, Mn, and Nb; nontraditional NNN ligands with Zr; NCN ligands with W, Mo, Ti, La, Ta and Mn; and OCO ligands with Ti, Ta, and Mo. The early transition metals form complexes with pincer type ligands where the donors are all considered hard donors. Although OCO pincer ligands form transition metal complexes, the metal-carbon bond is susceptible to degradation via insertion reactions. Hence, pincer ligands that are not readily susceptible to degradation but can bind to group III through group X transition metals could be useful for catalysts for a broad scope of reactions including N-atom transfer reactions, aerobic oxidation, olefin polymerization, alkene isomerization, and C—H bond activation.

BRIEF SUMMARY

Embodiments of the invention are directed to ONO pincer ligands in their protonated, partly protonated, or trianionic forms and the transition metal complexes comprising the ONO pincer ligands. The ligands share a structural feature of a central nitrogen atom connected via a pair of bridges comprising three carbon atoms or two carbon atoms and a silicon atom to a pair of oxygen atoms where at least two of the carbon atoms are $sp^2$ hybridized. The two bridges can be of like structure or different structure, and can include substituents to provide desired steric and electronic properties of transition metal complexes comprising the ONO pincer ligands.

Embodiments of the invention are directed to the preparation of the ONO pincer ligands. Other embodiments of the invention are directed to the preparation of transition metal complexes comprising an ONO pincer ligand.

BRIEF DESCRIPTION OF DRAWINGS

FIG. 11 is tabulated crystal data and structure refinement for 6.

FIG. 12 is tabulated atomic coordinates and equivalent isotropic displacement parameters for 6.

FIG. 13 is tabulated bond lengths and angles for 6.

FIG. 14 is tabulated anisotropic displacement parameters for 6.

FIG. 18 is tabulated crystal data and structure refinement for 7.

FIG. 19 is tabulated atomic coordinates and equivalent isotropic displacement parameters for 7.

FIG. 20 is tabulated bond lengths and angles for 7.

FIG. 24 is tabulated crystal data and structure refinement for 8.

FIG. 25 is tabulated atomic coordinates and equivalent isotropic displacement parameters for 8.

FIG. 26 is tabulated bond lengths and angles for 8.

FIG. 27 is tabulated anisotropic displacement parameters for 8.

FIG. 41 is tabulated crystal data and structure refinement for 12.

FIG. 42 is tabulated atomic coordinates and equivalent isotropic displacement parameters for 12.

FIG. 43 is tabulated bond lengths and angles for 12.

FIG. 44 is tabulated anisotropic displacement parameters for 12.

FIG. 48 is tabulated crystal data and structure refinement for 16.

FIG. 49 is tabulated atomic coordinates and equivalent isotropic displacement parameters for 16.

FIG. 50 is tabulated bond lengths for 16.

FIG. 51 is tabulated bond angles for 16.

FIG. 52 is tabulated anisotropic displacement parameters for 16.

DETAILED DISCLOSURE

Figure 1:
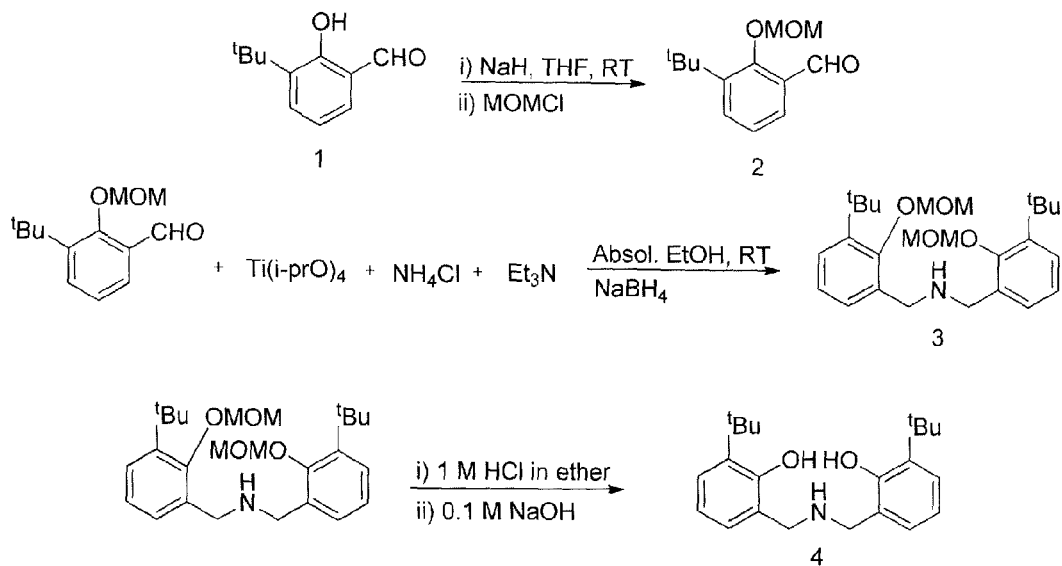
FIG. 1 is a scheme for the synthesis of 6,6'-(azanediylbis(methylene))bis(2-(tert-butyl)phenol) (4) according to an embodiment of the invention.

Embodiments of the invention are directed to ONO pincer ligands: the trianionic ONO pincer ligands; the protonated ONO ligand precursors; the trianionic ONO pincer ligand comprising transition metal complexes; methods for the preparation of the precursors; and methods for the preparation of the complexes. Modification of the ONO pincer ligand structure allows the modification of the steric and electronic properties of the transition metal complexes thereof. The trianionic ONO pincer ligands comprise a central nitrogen anion that is disubstituted with a pair of three carbon comprising bridges to terminal oxygen anions, or optionally a bridge comprising two carbons and one sp³ silicon where the silicon is adjacent to the oxygen. Two adjacent carbons of the bridge are sp² hybridized where a heteroatom, either the nitrogen or oxygen, is zusammen (cis) to the third carbon or the sp³ silicon of the bridge, such that the anionic ONO pincer ligand can achieve, but are not necessarily restricted to, a conformation where the heteroatoms and bridging carbons are coplanar:

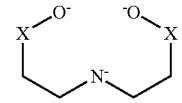

where X is C or Si.

Embodiments of the invention are described below where the two bridges are identical in bridging structure, although the identity of the substituents can result in asymmetric ONO pincer ligands. The ONO pincer ligands can be chiral or achiral. Other embodiments of the invention can have non-identical bridges, and, as can be appreciated by one skilled in the art, the bridge to the first oxygen can be of a different structure than the bridge to the second oxygen. For example: one bridge can comprise three sp² carbons and the other bridge can comprise two sp² carbons and one sp³ carbon; one bridge can be two sp² carbons and one sp³ carbon adjacent to the nitrogen and the other bridge can comprise two sp² carbons and an sp³ carbon adjacent to the oxygen; or the different two bridges can include one bridge with the structure of any of the embodiments below and the other bridge can include a bridge of any second embodiment below.

The trianionic ONO pincer ligand comprising transition metal complexes, according to embodiments of the invention, can include group III through group X transition metals. Embodiments of the invention are directed to ONO pincer ligand comprising transition metal complexes where the metals are early transition metals of group III through group VI. The trianionic ONO pincer ligand comprising transition metal complexes can be used as catalysts. Depending on the structure of the trianionic ONO pincer ligand comprising transition metal complex, the catalysis therefrom can be used for N-atom transfer reactions, aerobic oxidation, olefin polymerization, alkene isomerization, olefin metathesis, alkyne metathesis, alkyne-nitrile cross metathesis, C—H bond activation, CO₂ fixation, and dinitrogen fixation.

In an embodiment of the invention the trianionic ONO pincer ligand comprises bridges with an sp² carbon adjacent to the oxygen and an sp³ carbon adjacent to the nitrogen of the structure:

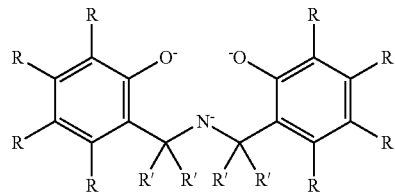

where R groups and R' groups are independently H, C₁-C₃₀ alkyl, C₂-C₃₀ alkenyl, C₂-C₃₀ alkynyl, C₆-C₁₄ aryl, C₇-C₃₀ arylalkyl, C₈-C₃₀ arylalkenyl, C₈-C₃₀ arylalkynyl, C₁-C₃₀ alkoxy, C₆-C₁₄ aryloxy, C₇-C₃₀ arylalkyloxy, C₂-C₃₀ alkenyloxy, C₂-C₃₀ alkynyloxy, C₈-C₃₀ arylalkenyloxy, C₈-C₃₀ arylalkynyloxy, C₂-C₃₀ alkylester, C₇-C₁₅ arylester, C₈-C₃₀ alkylarylester, C₃-C₃₀ alkenylester, C₃-C₃₀ alkynylester, C₃-C₃₀ polyether, C₃-C₃₀ polyetherester, C₃-C₃₀ polyester, or where any of the R and R' groups are perfluorinated, partially fluorinated, and/or otherwise substituted. Any alkyl group within the substituent can be linear, branched, cyclic, or any combination thereof. Alkenyl, alkynyl, ester, or ether functionality can be situated adjacent or remotely to the substituted carbon. Any of the R or R' groups that are not H can be further substituted with other functionality, for example, a terminal alkene, alkyne, amino, hydroxy, trialkoxysilyl, or other group. The ONO pincer ligand can be covalently fixed to a polymer, polymeric network, a resin or other surface such as a glass or ceramic. In embodiments of the invention, any pair of R groups, any pair of R' groups, or any R and R' groups of the same bridge can be combined into any five to eight membered cyclic structure. For example, the substituted phenyl groups shown above can be part of a polycyclic aromatic where two R groups are an additional aromatic ring or rings.

In an embodiment of the invention, the R group ortho to the sp$^3$ carbon of the bridge is connected to an R' group of that sp$^3$ carbon to form an anionic ONO pincer ligand of the structure:

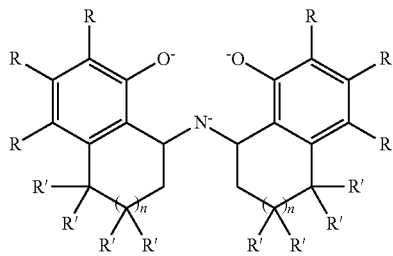

where n is 0 to 2 and R and R' are defined as above.

In an embodiment of the invention the trianionic ONO pincer ligand comprises bridges with an sp$^2$ carbon adjacent to the nitrogen and an sp$^3$ carbon adjacent to the oxygen of the structure:

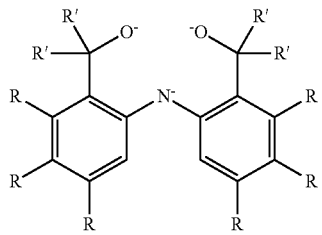

where R groups and R' groups are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $C_3$-$C_{30}$ polyether, $C_3$-$C_{30}$ polyetherester, $C_3$-$C_{30}$ polyester, or where any of the R and R' groups are perfluorinated, partially fluorinated, and/or otherwise substituted. Any alkyl group within the substituent can be linear, branched, cyclic, or any combination thereof. Alkenyl, alkynyl, ester, or ether functionality can be situated adjacent or remotely to the substituted carbon. Any of the R or R' groups that are not H can be further substituted with other functionality, for example, a terminal alkene, alkyne, amino, hydroxy, trialkoxysilyl, or other group. The ONO pincer ligand can be covalently fixed to a polymer, polymeric network, a resin or other surface such as a glass or ceramic. In embodiments of the invention, any pair of R groups, any pair of R' groups, or any R and R' groups of the same bridge can be combined into any five to eight membered cyclic structure. For example, the substituted phenyl groups shown above can be part of a polycyclic aromatic where two R groups are an additional aromatic ring or rings.

An exemplary embodiment of a trianionic ONO pincer ligand that has asymmetric bridges is a trianionic ONO pincer ligand of the structure:

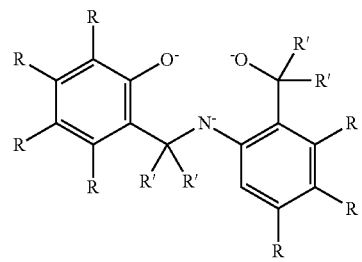

where R and R' are defined as above.

In an embodiment of the invention, the R group ortho to the sp$^3$ carbon of the bridge is connected to an R' group of that sp$^3$ carbon to form an anionic ONO pincer ligand of the structure:

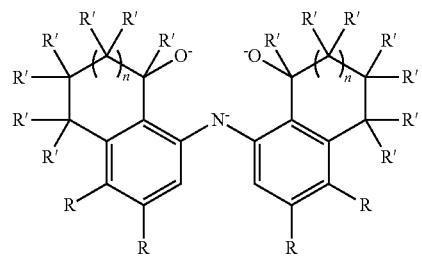

where n is 0 to 2 and R and R' are defined as above. Where two R' are combined into a cyclic structure a bicycle structure can be formed, such as:

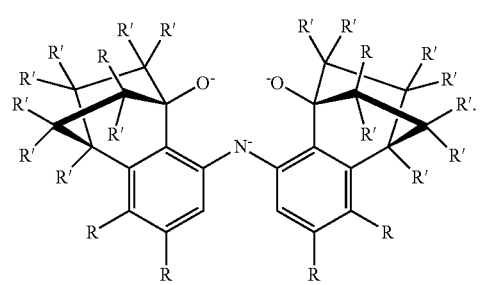

In an embodiment of the invention the trianionic ONO pincer ligand comprises bridges with an sp$^2$ carbon adjacent to the nitrogen and an sp$^3$ silicon adjacent to the oxygen of the structure:

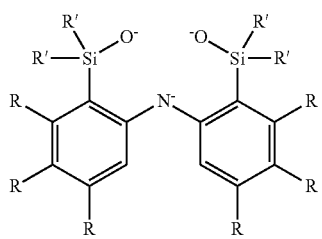

where: R groups are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy. $C_2$-$C_{30}$ alkynyloxy. $C_8$-$C_{30}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $C_3$-$C_{30}$ polyether, $C_3$-$C_{30}$ polyetherester, or $C_3$-$C_{30}$ polyester, or where any of the R groups are perfluorinated, partially fluorinated, and/or otherwise substituted; and R' groups are independently $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, or where any of the R' groups are partially fluorinated, and/or otherwise substituted. Any alkyl group within the substituent can be linear, branched, cyclic, or any combination thereof. Alkenyl, alkynyl, ester, or ether functionality can be situated adjacent or remotely to the substituted carbon. Any of the R or R' groups that are not H can be further substituted with functionality, for example, a terminal alkene, alkyne, amino, hydroxy, trialkoxysilyl, or other group. The ONO pincer ligand can be covalently fixed to a polymer, polymeric network, a resin or other surface such as a glass or ceramic.

In an embodiment of the invention the trianionic ONO pincer ligand comprises bridges with an sp² carbon adjacent to the nitrogen and on one bridge an sp³ silicon adjacent to the oxygen and on the other bridge an sp³ carbon adjacent to the oxygen of the structure:

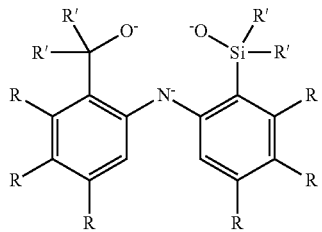

where R groups and R' groups attached to a carbon atom are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $C_3$-$C_{30}$ polyether, $C_3$-$C_{30}$ polyetherester, $C_3$-$C_{30}$ polyester, or where any of the R and R' groups are perfluorinated, partially fluorinated, and/or otherwise substituted; and R' groups attached to a silicon atom are independently $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, or where any of the R' groups are partially fluorinated, and/or otherwise substituted or any combination thereof. Any alkyl group within the substituent can be linear, branched, cyclic, or any combination thereof. Alkenyl, alkynyl, ester, or ether functionality can be situated adjacent or remotely to the substituted carbon. Any of the R or R' groups that are not H can be further substituted with a functional group, for example, a terminal alkene, alkyne, amino, hydroxy, trialkoxysilyl, or other group. The ONO pincer ligand can be covalently fixed to a polymer, polymeric network, a resin or other surface such as a glass or ceramic.

In one embodiment of the invention, sp² hybridized carbons of the two bridges that are ortho to the nitrogen can be connected to form an anionic ONO pincer ligand of the structure:

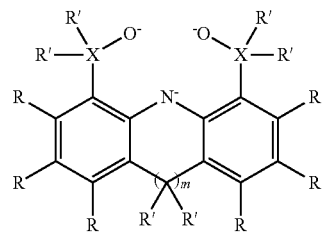

where X groups are independently C or Si, m is 0 or 1, and R and R' are defined as above where X is C and where X is Si.

In an embodiment of the invention the trianionic ONO pincer ligand comprises bridges with an sp² carbon adjacent to the nitrogen and an sp² carbon adjacent to the oxygen of the structure:

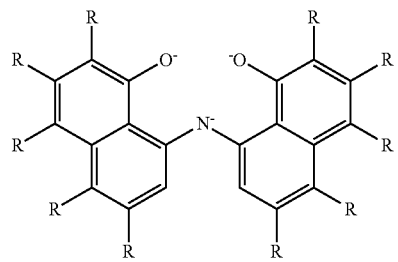

where R groups are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $C_3$-$C_{30}$ polyether, $C_3$-$C_{30}$ polyetherester, $C_3$-$C_{30}$ polyester, or where any of the R groups are perfluorinated, partially fluorinated, and/or otherwise substituted. Any alkyl group within the substituent can be linear, branched, cyclic, or any combination thereof Alkenyl, alkynyl, ester, or ether functionality can be situated adjacent or remotely to the substituted carbon. Any of the R groups that are not H can be further substituted with functionality, for example, a terminal alkene, alkyne, amino, hydroxy, trialkoxysilyl, or other group. The ONO pincer ligand can be covalently fixed to a polymer, polymeric network, a resin or other surface such as a glass or ceramic. In embodiments of the invention, any pair of R groups can be combined into any five to eight membered cyclic structures.

In one embodiment of the invention, two sp² hybridized carbons of the two bridges that are ortho to the nitrogen can be connected to form an anionic ONO pincer ligand of the structure:

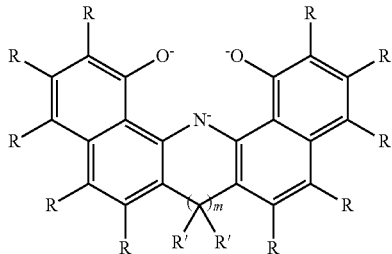

where m is 0 or 1, and R is defined as above and R' is defined as above when attached to a carbon atom.

In an embodiment of the invention the trianionic ONO pincer ligand comprises bridges with an sp² carbon adjacent to the nitrogen and an sp² carbon adjacent to the oxygen of the structure:

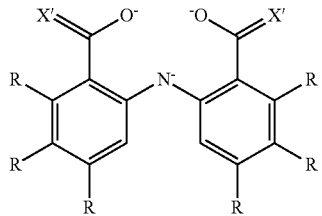

where X' groups are independently O or R"$_2$C; R groups are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $C_3$-$C_{30}$ polyether, $C_3$-$C_{30}$ polyetherester, or $C_3$-$C_{30}$ polyester; and R" groups are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, or where any of the R or R" groups are perfluorinated, partially fluorinated, and/or otherwise substituted. Any alkyl group within the substituent can be linear, branched, cyclic, or any combination thereof. Alkenyl, alkynyl, ester, or ether functionality can be situated adjacent or remotely to the substituted carbon. Any of the R groups that are not H can be further substituted with functionality, for example, a terminal alkene, alkyne, amino, hydroxy, trialkoxysilyl, or other group. The ONO pincer ligand can be covalently fixed to a polymer, polymeric network, a resin or other surface such as a glass or ceramic. In embodiments of the invention, any pair of R groups, R" groups can be combined into any five to eight membered cyclic structure.

In one embodiment of the invention, two sp² hybridized carbons of the two bridges that are ortho to the nitrogen can be connected to form a trianionic ONO pincer ligand of the structure:

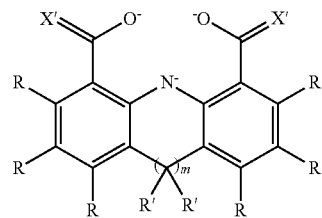

where X', m, R, R', and R" are defined as above where R' is bonded to carbon.

In an embodiment of the invention the trianionic ONO pincer ligand comprises bridges with an sp² carbon adjacent to the nitrogen and an sp² carbon adjacent to the oxygen of the structure:

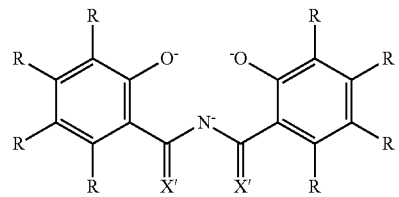

where X' groups are independently O or R"$_2$C; R groups are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $C_2$-$C_{30}$ alkylester, $C_7$-$C_{15}$ arylester, $C_5$-$C_{30}$ alkylarylester, $C_3$-$C_{30}$ alkenylester, $C_3$-$C_{30}$ alkynylester, $C_3$-$C_{30}$ polyether, $C_3$-$C_{30}$ polyetherester, $C_3$-$C_{30}$ polyester, or where any of the R groups are perfluorinated, partially fluorinated, and/or otherwise substituted; and R" groups are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, or where any of the R" groups are perfluorinated, partially fluorinated, and/or otherwise substituted. Any alkyl group within the substituent can be linear, branched, cyclic, or any combination thereof. Alkenyl, alkynyl, ester, or ether functionality can be situated adjacent or remotely to the substituted carbon. Any of the R groups that are not H can be further substituted with functionality, for example, a terminal alkene, alkyne, amino, hydroxy, trialkoxysilyl, or other group. The ONO pincer ligand can be covalently fixed to a polymer, polymeric network, a resin or other surface such as a glass or ceramic. In embodiments of the invention, any pair of R groups, R" groups can be combined into any five to eight membered cyclic structure, for example:

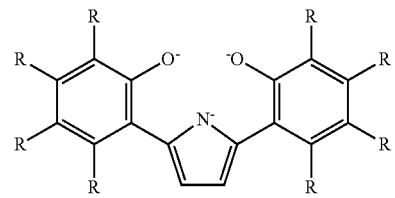

The trianionic ONO pincer ligands can be formed from their protonated precursors or from a precursor having a proton equivalent, for example, the nitrogen can be bonded to a silicon atom as a silazane or an active amide, or, for example the oxygen can be part of an active ester or ether, where the anionic oxygen and nitrogen can be readily formed by one or more reactions that gives the identical trianionic ONO pincer ligand to that of deprotonation of a protonated precursor. The protonated precursors to the trianionic form of the ONO pincer ligands shown above have the structures:

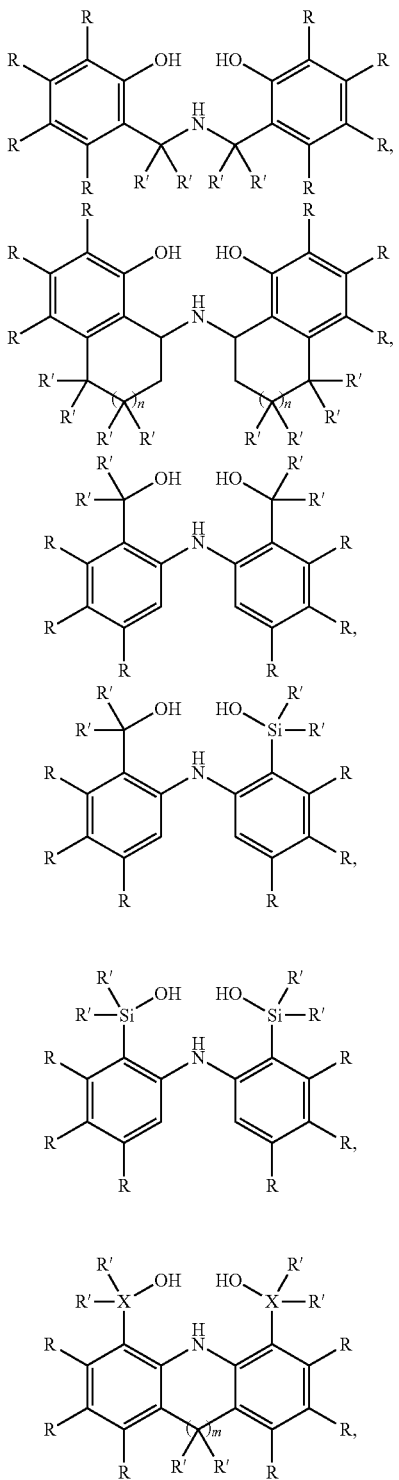

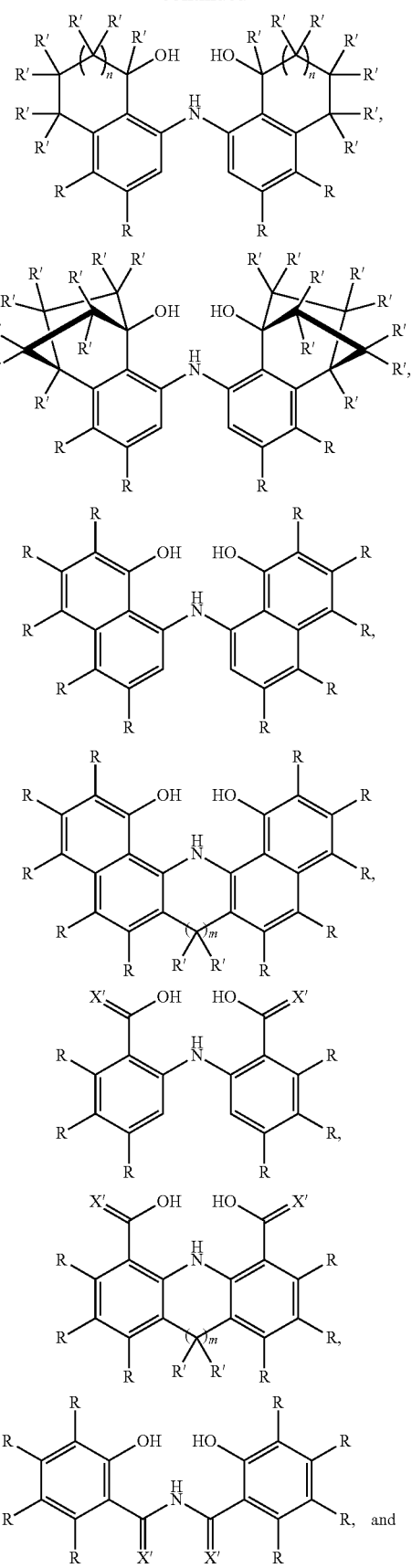

-continued

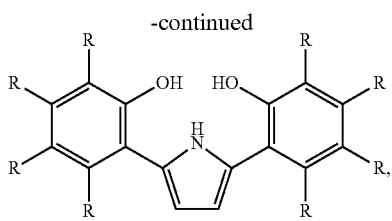

where X, X'. R, R', R", n and m are defined for the above equivalent trianionic OCO pincer ligands. Where X' is R"$_2$C and the beta heteroatom is oxygen, a ketone equivalent to the enol can be the predominate form of the protonated precursor prior to formation of the trianionic form of the ONO pincer ligand. Where X is Si, depending upon the nature of R', a silanol species may not be sufficiently stable for long term storage, but can be generated from a trimethylsilyloxy, acetoxy, or other proton equivalent by nucleophilic substitution, for example, by a fluoride ion at a trimethylsilyloxy or water with an acetoxy, to form siloxide anion or the silanol, respectively, prior to or during the formation of a transition metal complex of the ONO pincer ligand.

Methods to prepare the ONO precursors are numerous, as can be appreciated by those skilled in the art. According to embodiments of the invention, a nucleophilic oxygen or nucleophilic nitrogen compound are condensed with an electrophilic carbon of a molecule comprising the bridge structure. In some embodiments of the invention, the electrophilic carbon containing the bridge structure also contains the oxygen or the nitrogen that is not formed by reaction with the nucleophile, where that oxygen or nitrogen is protected prior to the nucleophilic reaction. Two exemplary embodiments of the methods of preparation of the precursor ONO pincer ligands are illustrated below.

Preparation of the trianionic ONO pincer ligand comprising metal complexes can be carried out according to an embodiment of the invention, where a precursor metal compound comprising a metal alkoxide or metal amide allows formation of a trianionic ONO pincer ligand comprising complex upon proton and ligand exchange between the alkoxide or amide of the metal alkoxide or metal amide and the anionic ONO pincer ligand. In another embodiment of the method, a precursor metal compound comprises a metal oxide or metal amide and further comprises a metal alkylidyne wherein the ligand exchange is accompanied by OH or NH addition across the metal alkylidyne to form the anionic ONO pincer ligand comprising metal complexes. Three exemplary embodiment of the method of preparation of the anionic ONO pincer ligand comprising metal complexes are illustrated below.

Methods and Materials

General Considerations.

Unless specified otherwise, all manipulations were performed under an inert atmosphere using standard Schlenk or glovebox techniques. Glassware was oven-dried before use. Pentane, hexanes, toluene, diethyl ether (Et$_2$O), tetrahydrofuran (THF), 1,2-dimethoxyethane (DME), and acetonitrile were dried using a GlassContours drying column. Benzene-d$_6$ and toluene-d$_8$ (Cambridge Isotopes) were dried over sodium-benzophenone ketyl and distilled or vacuum transferred and stored over 4 Å molecular sieves. NMR spectra were obtained on Varian INOVA 500 MHz, Varian Mercury Broad Band 300 MHz, or Varian Mercury 300 MHz spectrometers. Chemical shifts are reported in δ (ppm). For $^1$H and $^{13}$C {$^1$H} NMR spectra, the solvent resonance was referenced as an internal reference. Accurate mass was determined by Atmospheric Pressure Chemical Ionization-Mass Spectrometric (APCI-MS) method in diluted dichloromethane solution, and the spectrum was recorded on an Agilent 6210 TOF-MS. Elemental analyses were performed at Complete Analysis Laboratory Inc., Parsippany, N.J.

Synthesis of 6,6'-(azanediylbis(methylene))bis(2-(tert-butyl)phenol) (4)

As indicated in the reaction scheme shown in FIG. 1, ortho-substituted salicylaldehyde (1) (1.8 g, 10.1 mmol) was treated with NaH or KH (12.12 mmol) in dry THF for one hour at room temperature followed by the addition of excess methoxymethyl chloride (MOMCl) (30.3 mmol) via syringe. Stirring the resulting reaction mixture overnight resulted in the MOM protection aldehyde (2) as golden yellow oil after column chromatographic purification (hexanes/ethyl acetate (80/20) in 80% yield. A slurry of the protected aldehyde (2) (1.5 g, 6.75 mmol), Ti(i-PrO)$_4$ (4 mL, 13.5 mmol), NH$_4$Cl (722 mg, 13.5 mmol) and triethylamine (1.9 mL, 13.5 mmol) in absolute ethanol (25 mL) was stirred under Ar in a capped flask at ambient temperature for 12 hours, after which NaBH$_4$ (383 mg, 10.13 mmol) was added and the resulting mixture was stirred for additional 7 hours at ambient temperature. The reaction was quenched by pouring the mixture into an ammonium hydroxide solution (2 M, 25 mL). The resulting precipitate was filtered, and washed with ethyl acetate (2×25 mL). The organic layer was separated and the remaining aqueous layer was extracted with ethyl acetate (2×25 mL). The combined organic extracts were dried over MgSO$_4$ and concentrated under vacuum to obtain 3. Deprotection of the MOM ether was achieved by treating 3 with 3 equivalents of HCl (1 M HCl solution in ether). Upon addition of HCl a precipitate formed and subsequently was filtered, dried, and dissolved in CHCl$_3$. A NaOH solution (0.1 M) was added to neutralize the solution. The organic layer was removed and dried with MgSO$_4$ and volatiles were removed. The residue was redissolved in a minimal amount of CHCl$_3$. The solution was heated and added to cold hexanes to precipitate [$^t$BuOCH$_2$NCH$_2$O]H$_3$ (4) as a white microcrystalline solid (yield=16%). ESI-MS: Calc. for [C$_{22}$H$_{32}$N$_1$O$_4$]$^+$: m/z 342.24 [4+H$^+$]. Found m/z 342.2.

$^1$H NMR data of (2): $^1$H NMR (300 MHz, CDCl$_3$), δ (ppm): 10.23 (s, 1H, CHO), 7.74-7.71 (dd, J=7.63 Hz, 1H, Ar—H), 7.63-7.59 (dd, J=7.93 Hz, 1H, Ar—H), 7.18 (t, J=7.63, 1H, Ar—H), 5.05 (s, 21-1, —OCH$_2$OCH$_3$), 3.65 (s, 3H, —OCH$_2$OCH$_3$), 1.44 (s, 9H, —C(CH$_3$)$_3$).

$^1$HNMR data of (3): $^1$H NMR (300 MHz, CDCl$_3$), δ (ppm): 7.28 (s, 2H, Ar—H), 7.26 (s, 2H, Ar—H), 7.03 (t, J=7.63, 2H, Ar—H), 5.04 (s, 4H, OCH$_2$OCH$_3$), 3.89 (s, 4H, Ar—CH$_2$) 3.59 (s, 6H, OCH$_2$OCH$_3$), 1.42 (s, 18H, —C(CH$_3$)$_3$).

NMR data of (4): $^1$H NMR (300 MHz, CDCl$_3$), δ (ppm): 7.26-7.23 (dd, J=7.93, 2H, Ar—H), 6.99-6.96 (dd, J=7.32, 2H, Ar—H), 6.81 (t, J=7.63, 2H, Ar—H), 3.94 (s, 4H, Ar—CH$_2$), 1.44 (s, 18H, —C(CH$_3$)$_3$). $^{13}$C{$^1$H} NMR (75.36 Hz, C$_6$D$_6$), δ (ppm): 155.29 (s, 2C, Ar), 136.93 (s, 2C, Ar), 127.94 (s, 2C, Ar), 126.75 (s, 2C, Ar), 123.75 (s, 2C, Ar), 119.63 (s, 2C, Ar), 51.20 (s, CH$_2$), 34.78 (s, —C(CH$_3$)$_3$), 29.95 (s, —C(CH$_3$)$_3$).

Synthesis of 2,2'-(azanediylbis(3-methyl-6,1-phenylene))bis(1,1,1,3,3,3-hexafluoro-propan-2-ol) [F$_6$ONO]H$_3$ (5)

Figure 2:
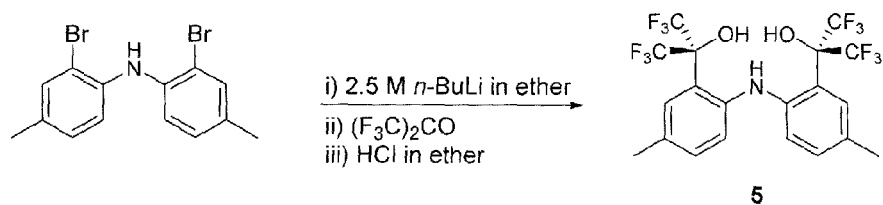
FIG. 2 is a scheme for the synthesis of 2,2'-(azanediylbis(3-methyl-6,1-phenylene))bis(1,1,1,3,3,3-hexafluoro-propan-2-ol) [$F_6$ONO]$H_3$ (5) according to an embodiment of the invention.
Figure 4:
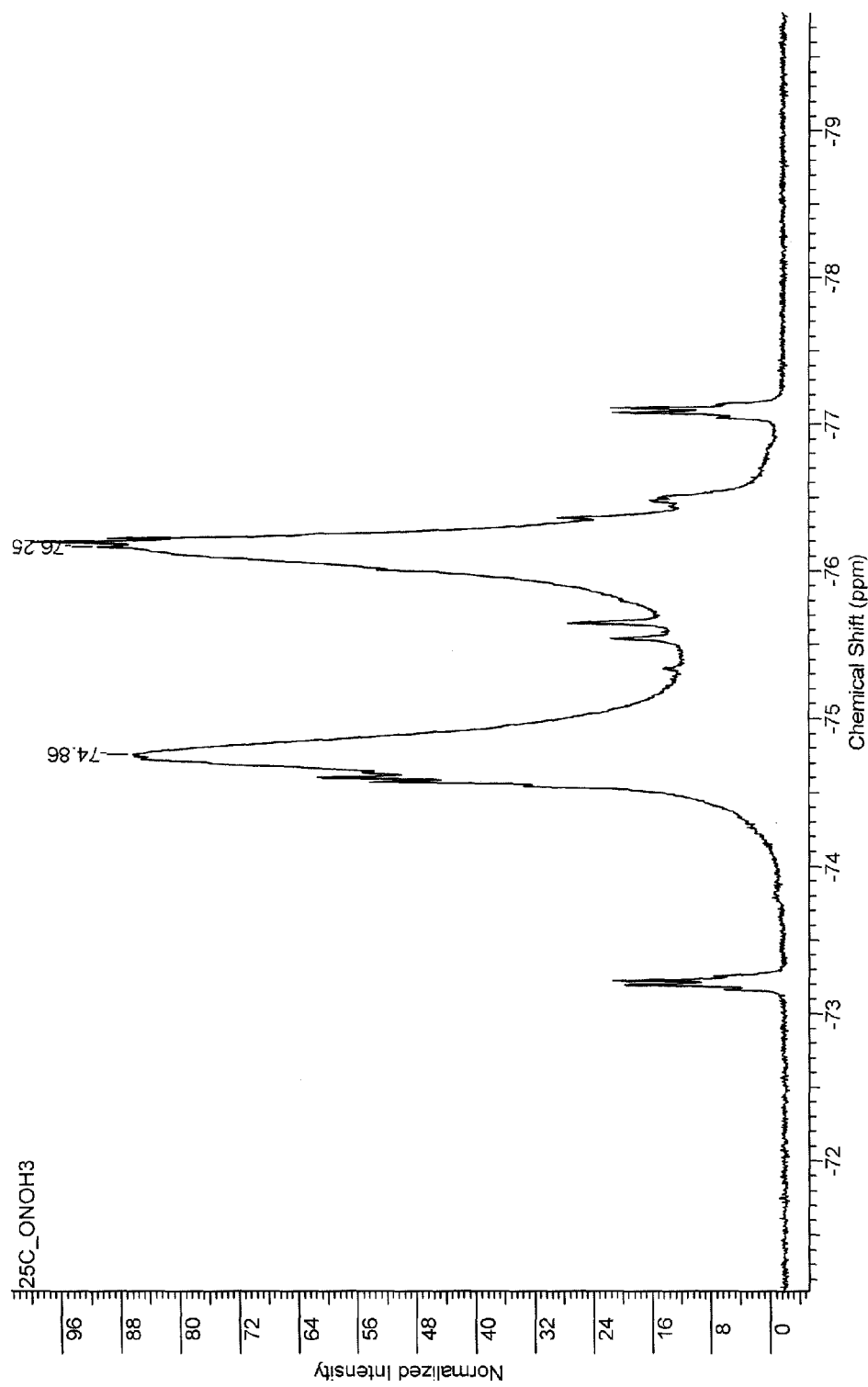
FIG. 4 is a $^{19}$F{$^1$H} NMR spectrum of 5 in CDCl$_3$.
Figure 5:
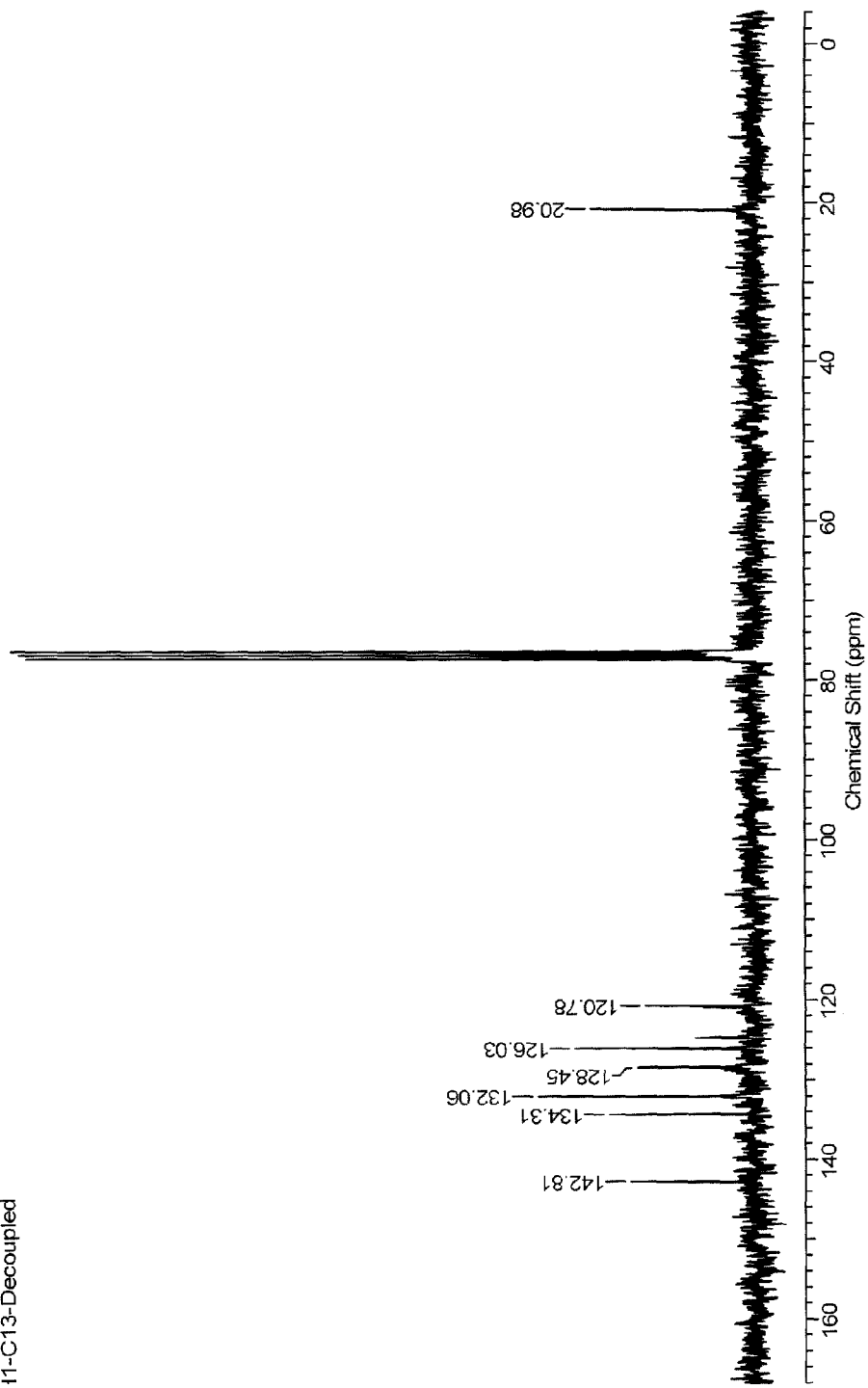
FIG. 5 is a $^{13}$C{$^1$H} NMR spectrum of 5 in CDCl$_3$.
Figure 6:
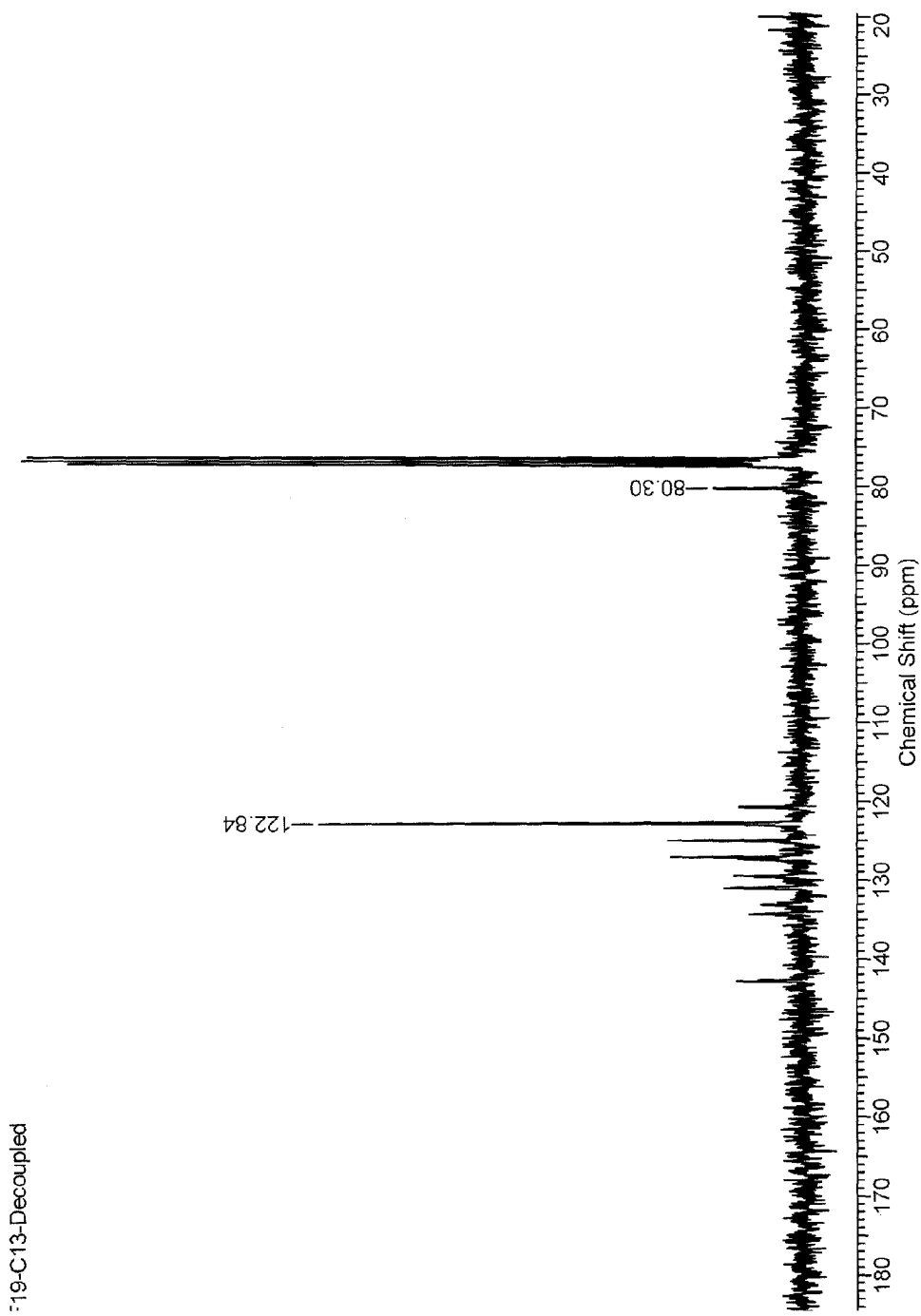
FIG. 6 is a $^{13}$C {$^{19}$F} NMR spectrum of 5 in CDCl$_3$.

As indicated in the reaction scheme shown in FIG. 2, in a nitrogen-filled glovebox an n-butyl-lithium solution (10.9 mL, 2.5 M, 27.3 mmol) was added dropwise to a Schlenk-flask containing a −35° C. solution of bis(2-bromo-4-methylphenyl)amine (3.103 g, 8.79 mmol) in diethyl ether (30 mL). The reaction mixture was stirred for two hours while warming to room temperature. The reaction flask was fitted with a dry-ice condenser before exiting the box. The reaction solution was cooled to −78° C., and dry-ice and acetone was added to the condenser. Hexafluoroacetone was condensed into a pressure flask at −78° C. (5 mL, 6.6 g, 39 mmol) prior to addition to the reaction flask. Hexafluoroacetone evaporates slowly and condenses into the reaction flask via the side-arm of the Schlenk flask. The reaction mixture was allowed to warm to room temperature and stirred for 3 hrs until the excess hexafluoroacetone evaporates. The addition of HCl in $Et_2O$ (27.3 mL, 1 M) precipitates lithium chloride from a red solution. The solution was filtered and the filtrate was reduced to a thick oil. The thick oil was placed under vacuum for two hours; then adding hexanes precipitated the product 5 as a pinkish-white powder (1.66 g, 35% yield). NMR ($CDCl_3$) (shown in FIG. 3): δ=7.5-7.0 (br, 3H, NH and 2 OH), 7.37 (s, 2H, Ar), 7.17 (d, 2H, $^3J$=8.35 Hz, Ar), 8.83 (d, 2H, $^3J$=8.35 Hz, Ar), and 2.36 (s, 3H, $CH_3$) ppm. $^{19}F\{^1H\}$ NMR ($CDCl_3$) (shown in FIG. 4): δ=−74.9 (br) and −76.3 (br) ppm. $^{13}C\{^1H\}$NMR ($CDCl_3$) (shown in FIG. 5): δ=142.8 (s, Ar C), 134.3 (s, Ar C), 132.1 (s, Ar C), 128.5 (s, Ar C), 126.0, (s, Ar C), 120.8, (s, Ar CH), and 21.0 (s, $CH_3$) ppm. $^{13}C\{^{19}F\}$NMR (CDCl3) (shown in FIG. 6): δ=122.8 (s, $CF_3$) and 80.3 (s, ($CF_3$)COH) ppm. Anal. Calcd. for $C_{20}H_{15}F_{12}NO_2$ (529.32 g/mole): C, 45.38; H, 2.86; N, 2.65. ESI-MS: 530.0984 [5+H]⁺, 552.0803 [5+Na]⁺, and 574.0623 [5−H+2Na]⁺.

Synthesis of [$F_6$ONO]W≡CHCH$_2$CH$_3$(O$^t$Bu) (6)

Figure 7:
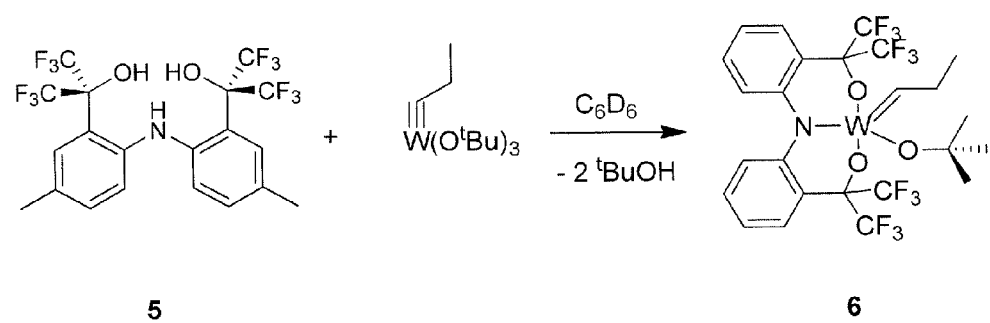
FIG. 7 is a scheme for the synthesis of [$F_6$ONO]W=CHCH$_2$CH$_3$(O$^t$Bu) (6) according to an embodiment of the invention.
Figure 8:
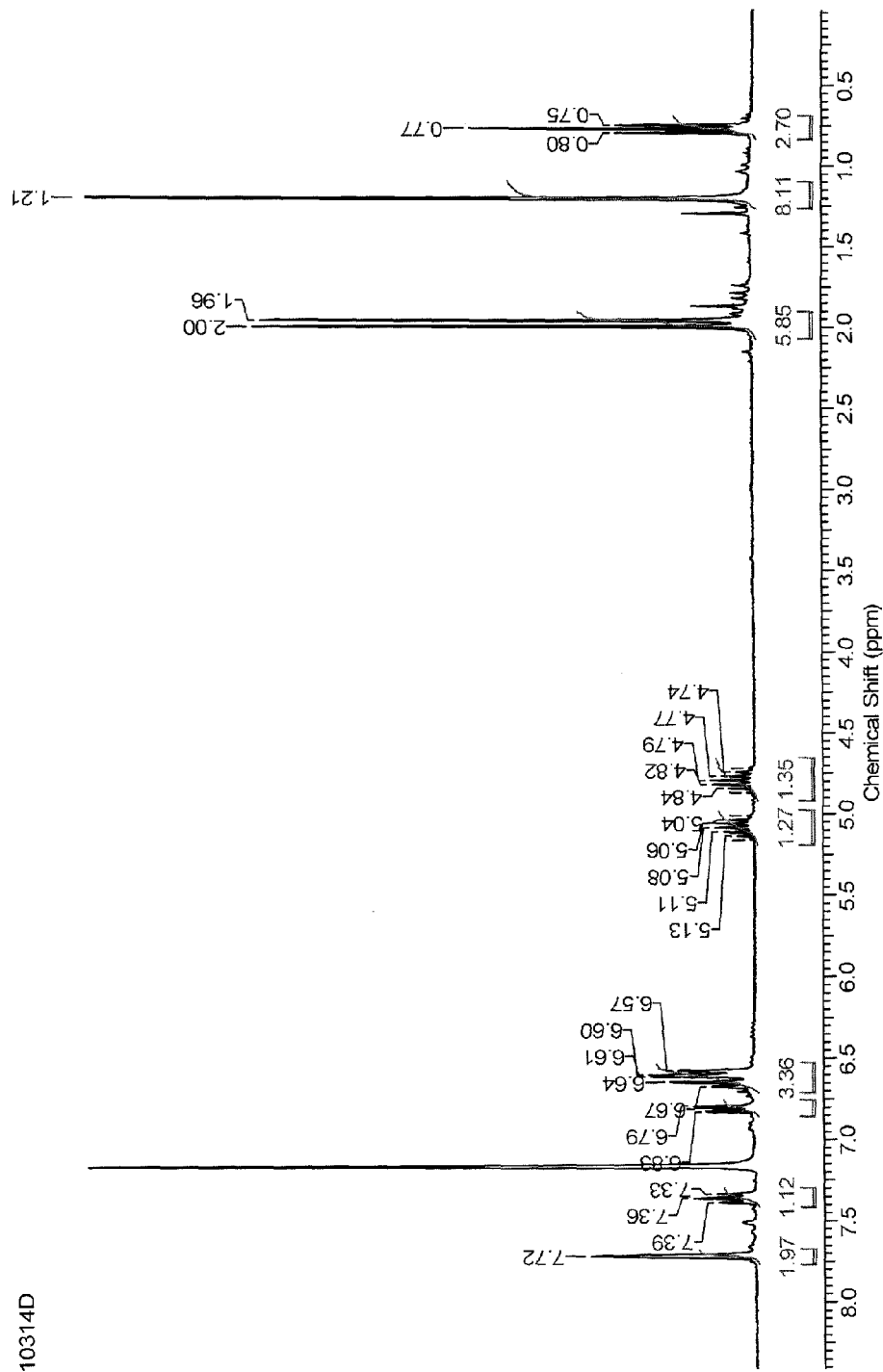
FIG. 8 is a $^1$H NMR spectrum of 6 in CDCl$_3$.
Figure 9:
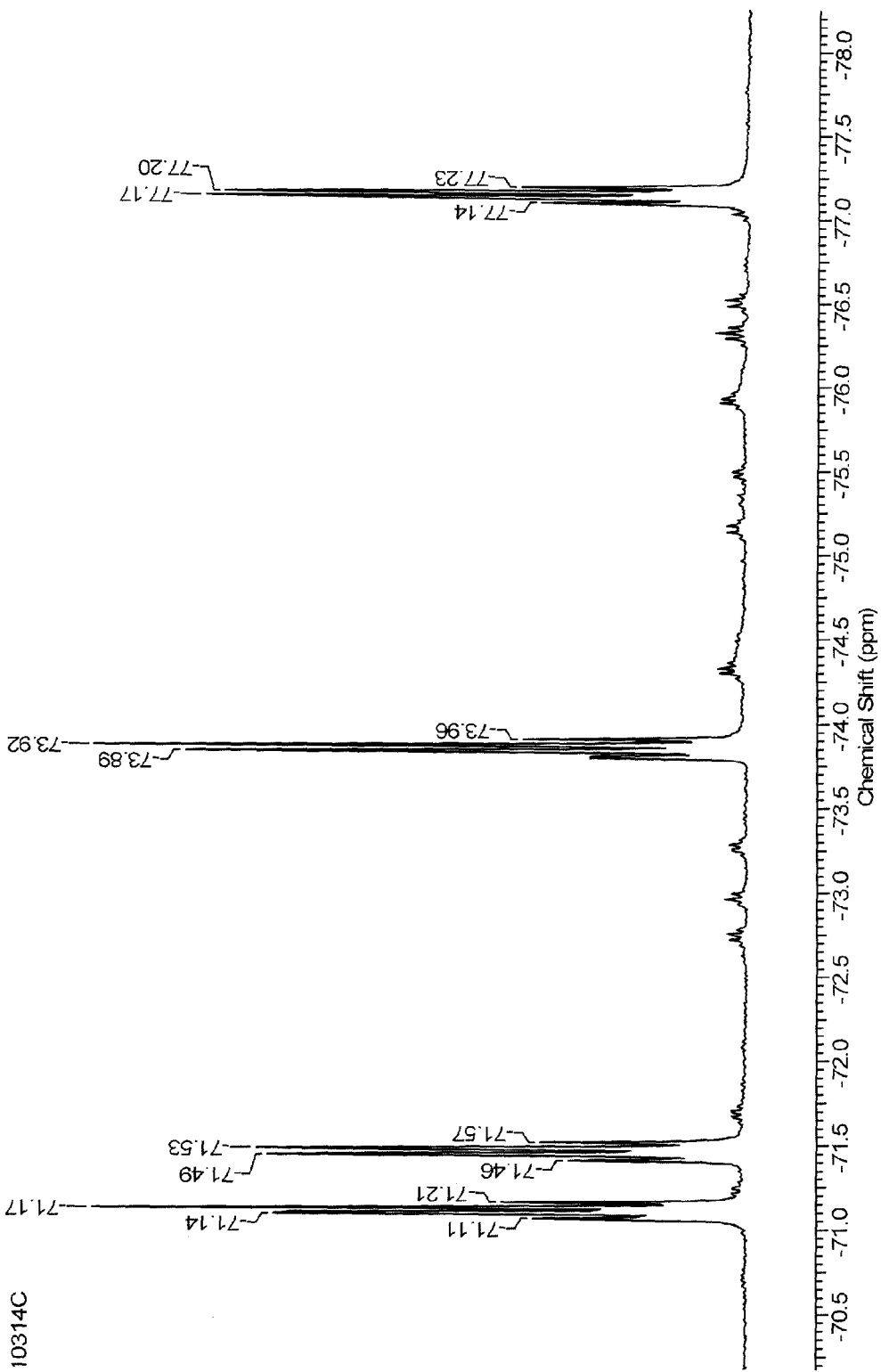
FIG. 9 is a $^{19}${$^1$H} NMR spectrum of 6 in CDCl$_3$.

As indicated in the reaction scheme shown in FIG. 7, a benzene solution (5 mL) of [$F_6$ONO]H$_3$ (5) and ($^t$BuO)$_3$W≡CCH$_2$CH$_3$ were combined and stirred for 0.5 h after which volatiles were removed in vacuo. $^1H$ NMR ($C_6D_6$) (shown in FIG. 8): δ=7.72 (s, 2H, Ar), 7.36 (t, 1H, $^3J$=7.64 Hz, WCHCH$_2$CH$_3$), 6.81 (d, 1H, $^3J$=8.49 Hz, Ar), 6.66 (d, 1H, $^3J$=8.21 Hz, Ar), 6.60 (d, 1H, $^3J$=9.06 Hz, Ar), 6.59 (d, 1H, $^3J$=8.49 Hz, Ar), 5.08 (ddq, 1H, $^2J$=15.0 Hz, $^3J$=7.36 Hz, $^3J$=7.36 Hz, WCHC(H)(H)CH$_3$), 5.08 (ddq, 1H, $^2J$=15.0 Hz, $^3J$=7.36 Hz, $^3J$=7.36 Hz, WCHC(H')(H)CH$_3$), 4.79 (ddq, 1H, $^2J$=15.0 Hz, $^3J$=7.64 Hz, $^3J$=7.64 Hz, WCHC(H')(H)CH$_3$), 2.00 (s, 3H, CH$_3$'), 1.96 (s, 3H, CH$_3$), 1.21 (s, 9H, OC(CH$_3$)$_3$, and 0.77 (t, $^3J$=7.36 Hz, WCHCH$_2$CH$_3$) ppm. $^{19}F\{^1H\}$ NMR ($C_6D_6$) (shown in FIG. 9): δ=71.2 (qt., 3F, $^4J$=9.61 Hz), 71.5 (qt., 3F, $^4J$=12.0 Hz), 73.9 (qt., 3F, $^4J$=9.60 Hz), and 77.2 (qt., 3F, $^4J$=9.61 Hz) ppm. $^{13}C\{^1H\}$ NMR ($C_6D_6$): δ=112.5 (s, Ar), 111.8 (s, Ar), 104.1 (s, Ar), 103.7 (s, Ar), 102.6 (s, Ar), 101.6 (s, Ar), 99.6 (s, Ar), 98.7 (s, Ar), 98.3 (br, Ar), 96.6 (s, Ar), 96.5 (s, Ar), 96.3 (s, Ar), 90.7 (s, OCMe$_3$), 33.6 (s, WCHCH$_2$CH$_3$), 29.8 (s, OC(CH$_3$)$_3$), 21.4 (s, WCHCH$_2$CH$_3$), 21.0 (s, CH$_3$'), and 20.8 (s, CH$_3$) ppm.

Figure 10:
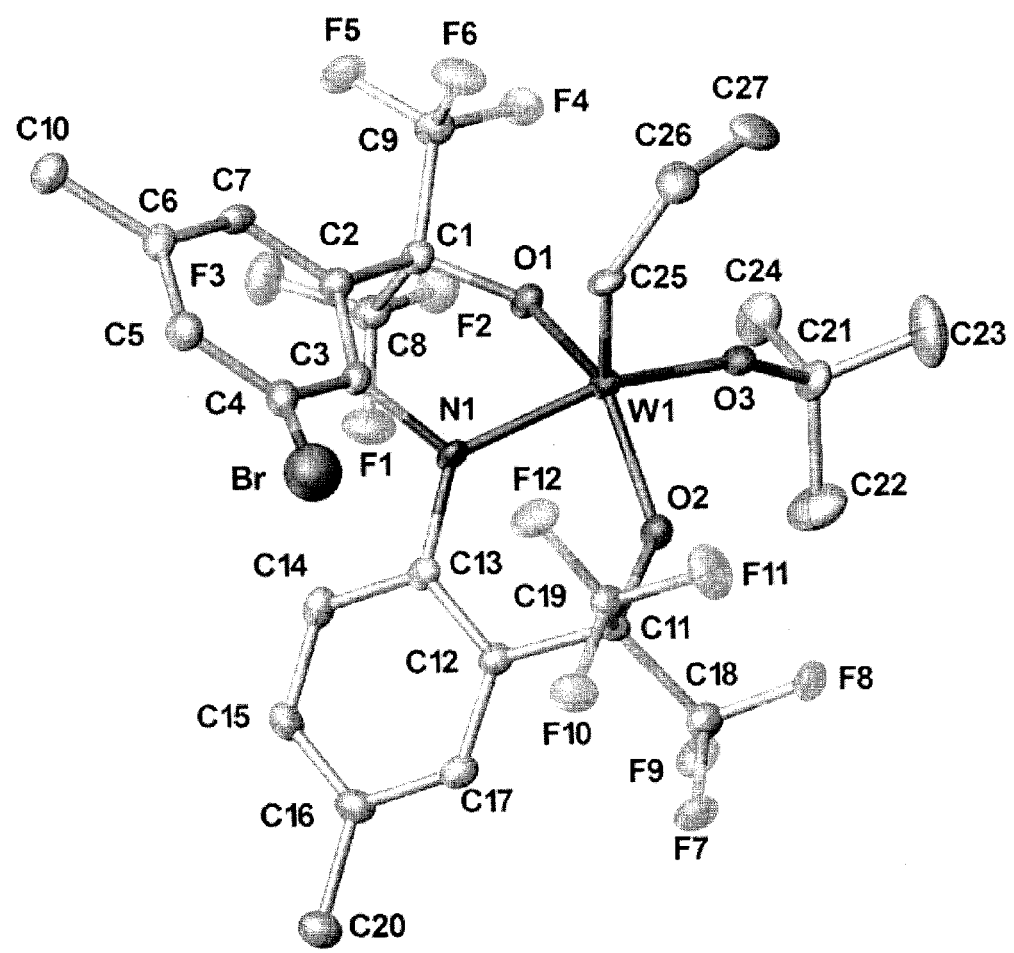
FIG. 10 shows the solid state structure of 6 as determined by X-ray crystallography.

X-Ray Experimental for 6:

X-Ray Intensity data were collected at 100 K on a Bruker SMART diffractometer using MoKα radiation (λ=0.71073 Å) and an APEXII CCD area detector. Raw data frames were read by program SAINT and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces. The structure (shown in FIG. 10) was solved and refined in SHELXTL6.1, using full-matrix least-squares refinement. The non-H atoms were refined with anisotropic thermal parameters and all of the H atoms were calculated in idealized positions and refined riding on their parent atoms. A disorder between H4a and a small percentage of Br on C4 was identified with the final refinement yielding 3% of Br and 97% of the proton. The Br atom was refined with several site occupation factors until an acceptable value was reached; which was 3%. In the final cycle of refinement, 5441 reflections (of which 4758 are observed with I>2σ(I)) were used to refine 403 parameters and the resulting $R_1$, $wR_2$ and S (goodness of fit) were 2.51%, 4.76% and 1.050, respectively. The refinement was carried out by minimizing the $wR_2$ function using $F^2$ rather than F values. $R_1$ is calculated to provide a reference to the conventional R value but its function is not minimized. SHELXTL6 (2000). Bruker-AXS, Madison, Wis., USA. FIG. 11 gives the crystal data and structure refinement for 6. FIG. 12 gives atomic coordinates and equivalent isotropic displacement parameters for 6. FIG. 13 gives bond lengths and angles for 6. FIG. 14 gives anisotropic displacement parameters for 6.

Synthesis of [$^t$BuOCH$_2$NHCH$_2$O]$_2$Mo (7)

Figure 15:
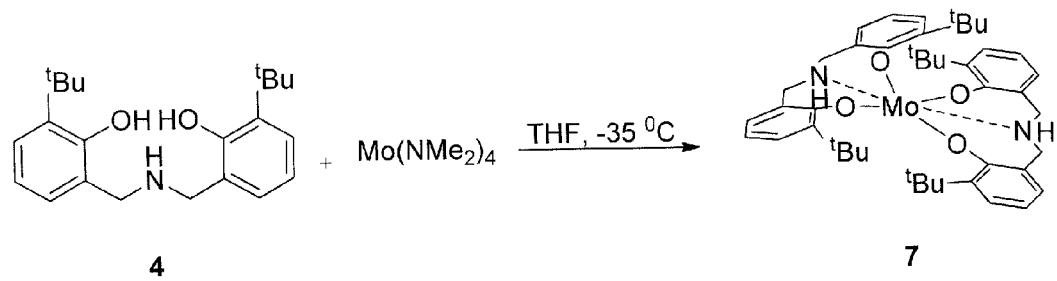
FIG. 15 is a scheme for the synthesis of [$^t$BuOCH$_2$NHCH$_2$O]$_2$Mo (7) according to an embodiment of the invention.
Figure 16:
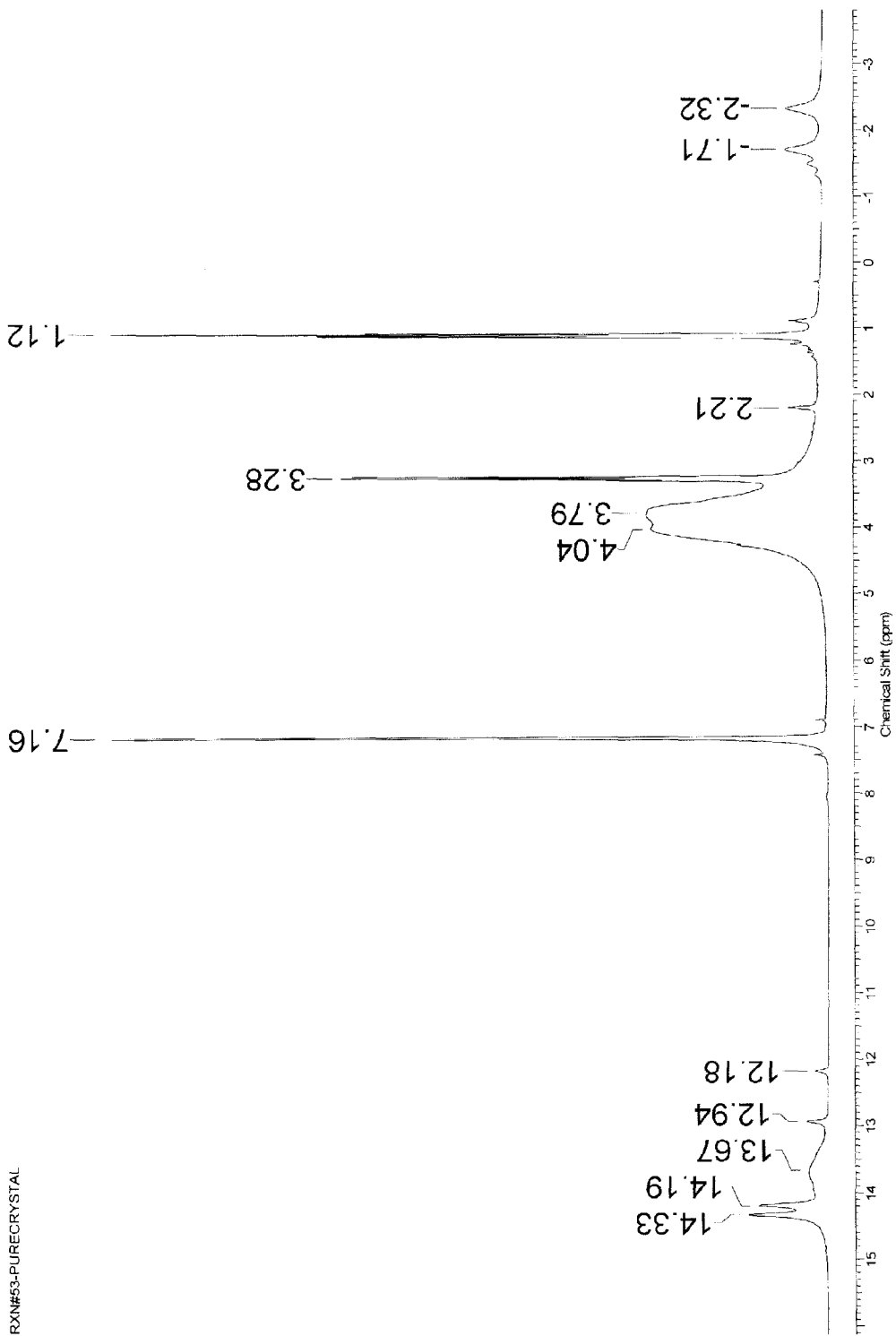
FIG. 16 is a $^1$H NMR spectrum of 7 in CDCl$_3$.

As indicated in the reaction scheme shown in FIG. 15, to a cold THF solution of [$^t$BuOCH$_2$NHCH$_2$O]H$_3$ (4) (51.2 mg, 0.15 mmol) was added dropwise a cold THF solution of molybdenum tetrakisdimethylamide (Mo(NMe$_2$)$_4$) (40.8 mg, 0.15 mmol) and the resulting solution was stirred for 30 minutes. The solvent was removed and the resulting residue was triturated with pentane and dried under vacuum. FIG. 16 shows a $^1H$ NMR spectrum of 7 in CDCl$_3$. Single crystals were grown by cooling a concentrated ether solution of the 7.

Figure 17:
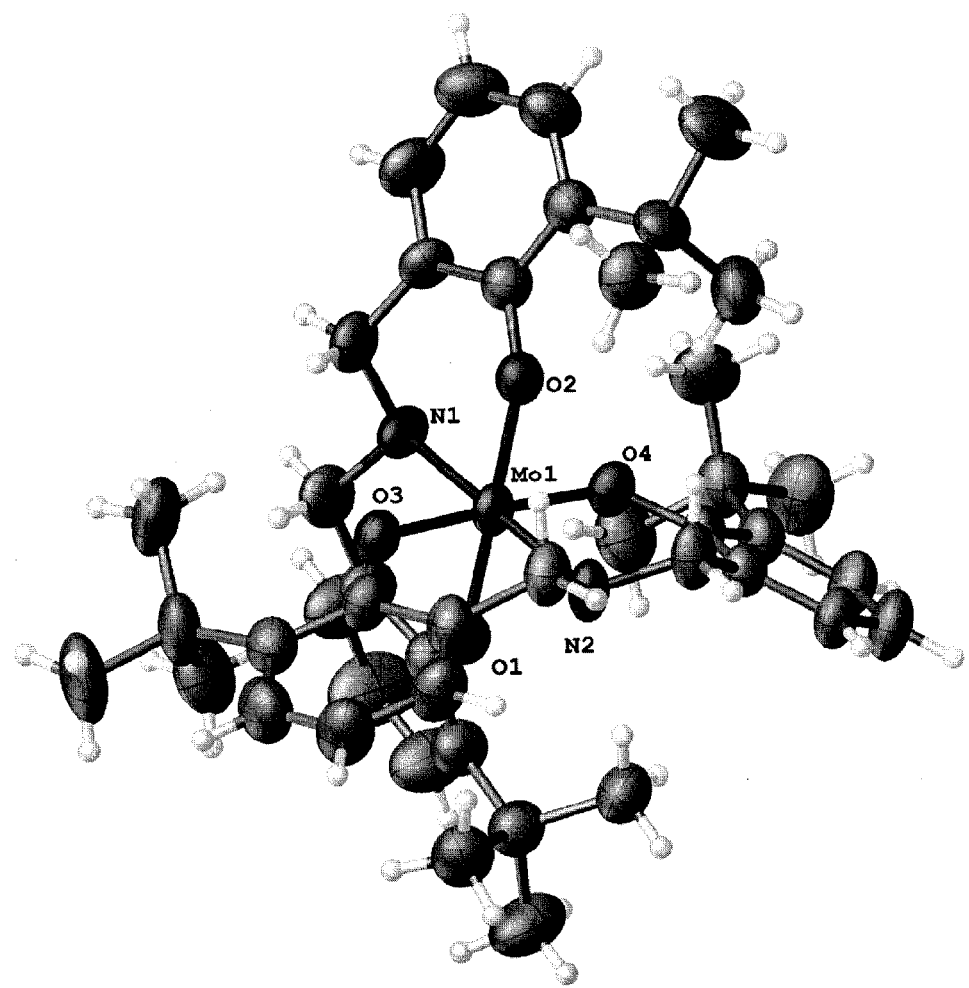
FIG. 17 shows the solid state structure of 7 with thermal ellipsoids drawn at the 50% probability level.
Figure 21:
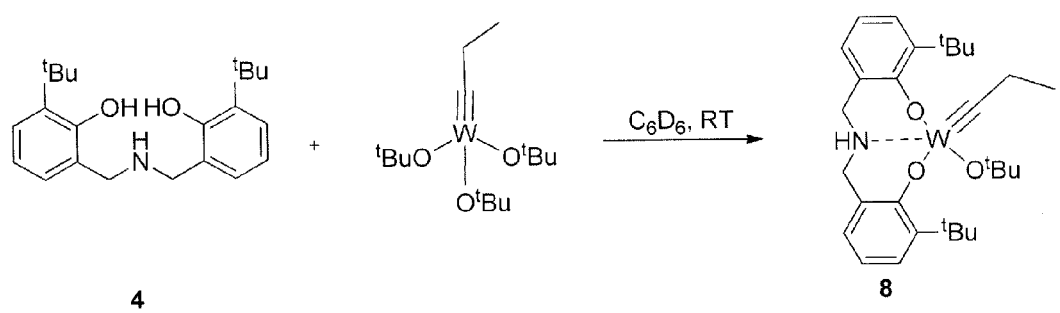
FIG. 21 is a scheme for the synthesis of [$^t$BuOCH$_2$NHCH$_2$O]W≡CCH$_2$CH$_3$ (8) according to an embodiment of the invention.

X-Ray Experimental for 7:

X-Ray Intensity data were collected at 100 K on a Bruker DUO diffractometer using MoKα radiation (λ=0.71073 Å) and an APEXII CCD area detector. Raw data frames were read by program SAINT[1] and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces. The structure (shown in FIG. 17) was solved and refined in SHELXTL6.1, using full-matrix least-squares refinement. The non-H atoms were refined with anisotropic thermal parameters and all of the H atoms were calculated in idealized positions and refined riding on their parent atoms. The asymmetric unit consists of the Mo complex and two ether solvent molecules in general positions. The latter were disordered and could not be modeled properly; thus program SQUEEZE, a part of the PLATON package of crystallographic software, was used to calculate the solvent disorder area and remove its contribution to the overall intensity data. In the final cycle of refinement, 11917 reflections (of which 5649 are observed with I>2σ(I)) were used to refine 472 parameters and the resulting $R_1$, $wR_2$ and S (goodness of fit) were 5.90%, 13.22% and 0.729, respectively. The refinement was carried out by minimizing the $wR_2$ function using $F^2$ rather than F values. $R_1$ is calculated to provide a reference to the conventional R value but its function is not minimized. FIG. 13 shows the solid state structure of 7 with thermal ellipsoids drawn at the 50% probability level. FIG. 18 give the crystal data and structure refinement for 7. FIG. 19 gives atomic coordinates and equivalent isotropic displacement parameters for 7. FIG. 20 gives bond lengths and angles for 7. FIG. 21 gives anisotropic displacement parameters for 7.

In situ generation of [$^t$BuOCH$_2$NHCH$_2$O]W≡CCH$_2$CH$_3$ (8).

Figure 22:
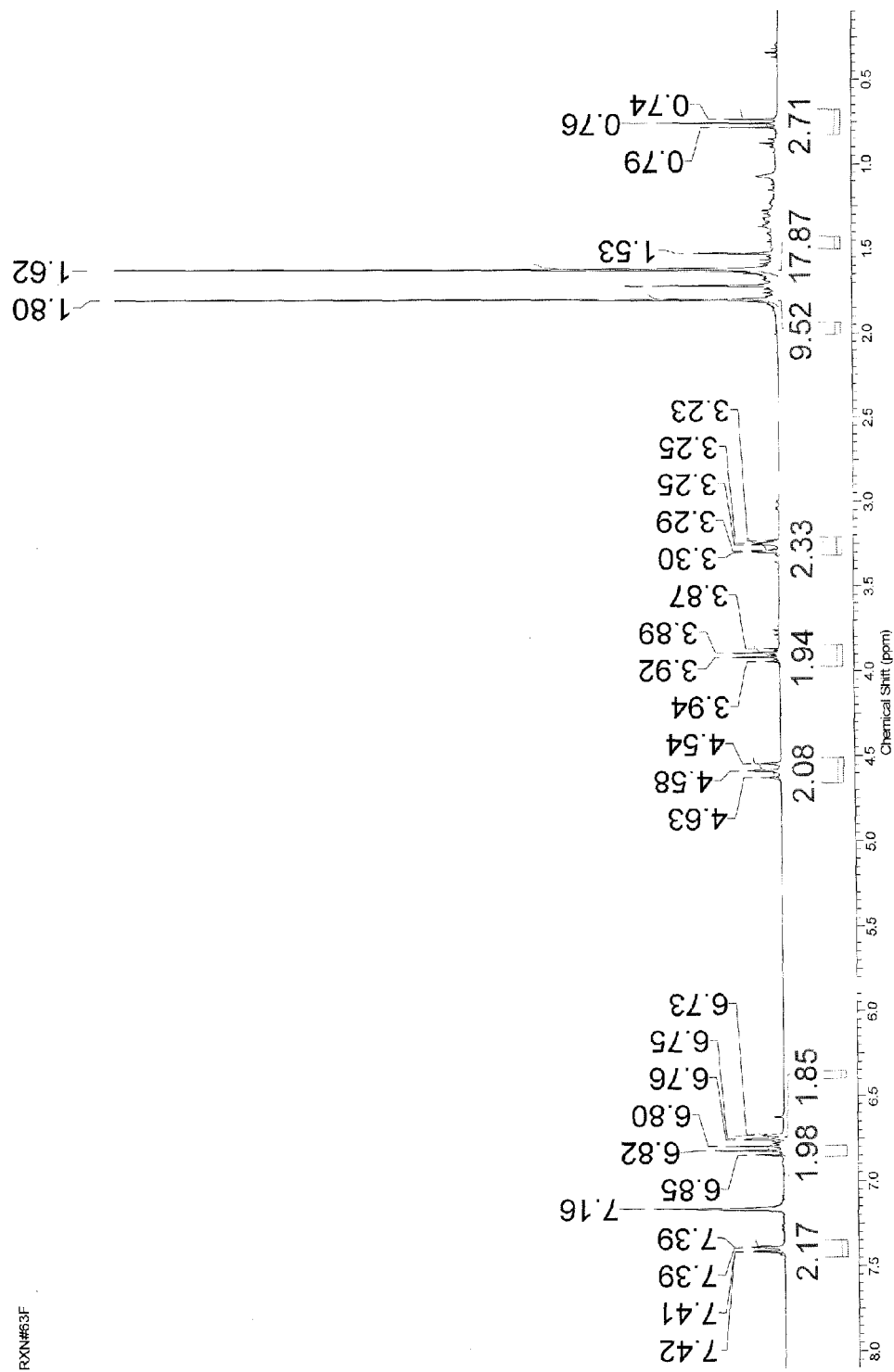
FIG. 22 is a $^1$H NMR spectrum of 8 in CDCl$_3$.

As indicated in the reaction scheme shown in FIG. 21, A J-Young tube was charged with the ligand precursor [$^t$BuOCH$_2$NCH$_2$O]H$_3$ (4) (7.85 mg, 0.023 mmol) and ($^t$BuO)$_3$W≡CCH$_2$CH$_3$ (10.2 mg, 0.023 mmol). Upon dissolving the alkylidyne, complex 8 forms. FIG. 22 shows a $^1$H NMR spectrum of 8 in CDCl$_3$.

Figure 23:
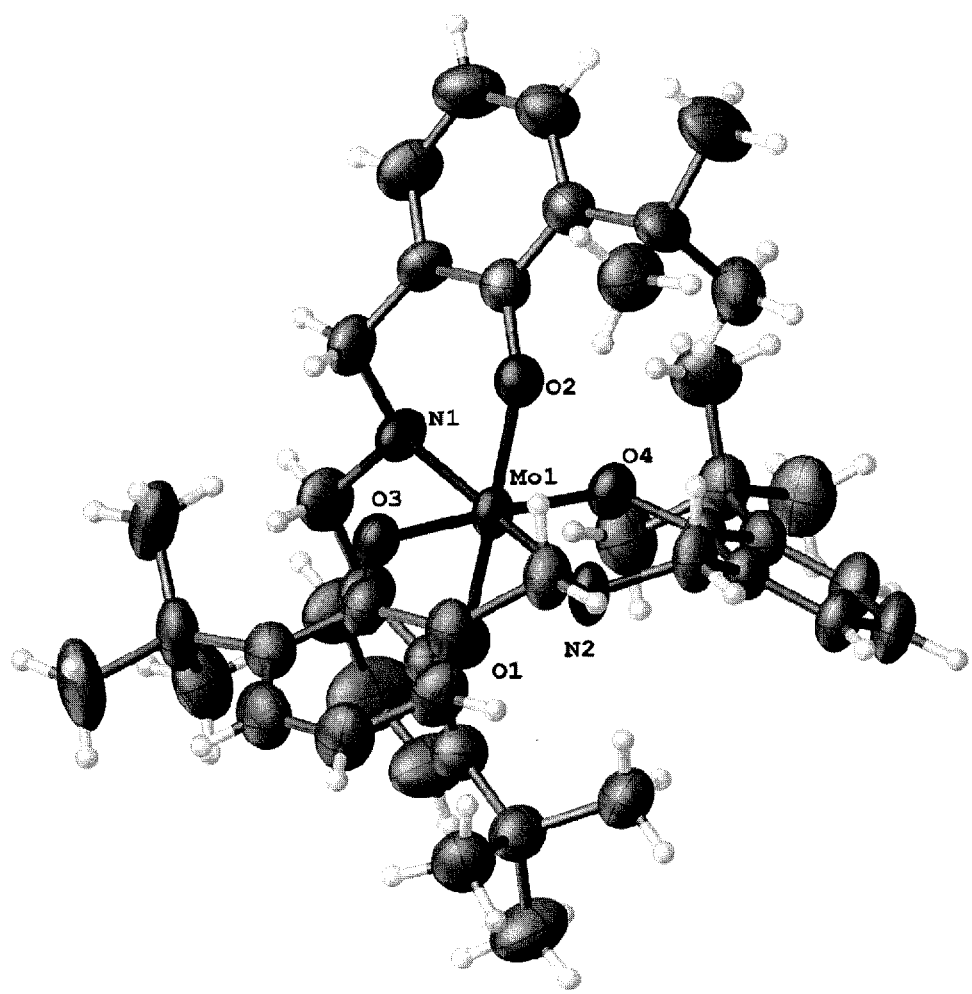
FIG. 23 shows the solid state structure of 8 with thermal ellipsoids drawn at the 50% probability level.

X-RAY Experimental for 8:

X-Ray Intensity data were collected at 100 K on a Bruker DUO diffractometer using MoKα radiation (λ=0.71073 Å) and an APEXII CCD area detector. Raw data frames were read by program SAINT[1] and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces. The structure (shown in FIG. 23) was solved and refined in SHELXTL6.1, using full-matrix least-squares refinement. The non-H atoms were refined with anisotropic thermal parameters and all of the H atoms were calculated in idealized positions and refined riding on their parent atoms. The asymmetric unit consists of the Mo complex and two ether solvent molecules in general positions. The latter were disordered and could not be modeled properly; thus program SQUEEZE, a part of the PLATON package of crystallographic software, was used to calculate the solvent disorder area and remove its contribution to the overall intensity data. In the final cycle of refinement, 11917 reflections (of which 5649 are observed with I>2σ(I)) were used to refine 472 parameters and the resulting R$_1$, wR$_2$ and S (goodness of fit) were 5.90%, 13.22% and 0.729, respectively. The refinement was carried out by minimizing the wR$_2$ function using F$^2$ rather than F values. R$_1$ is calculated to provide a reference to the conventional R value but its function is not minimized. FIG. 24 gives the crystal data and structure refinement for 8. FIG. 25 gives atomic coordinates and equivalent isotropic displacement parameters for 8. FIG. 26 gives bond lengths and angles for 8. FIG. 27 gives anisotropic displacement parameters for 8.

Synthesis of [CF$_3$—ONO]W(≡CH$^t$Bu)(O$^t$Bu) (9)

Figure 28:
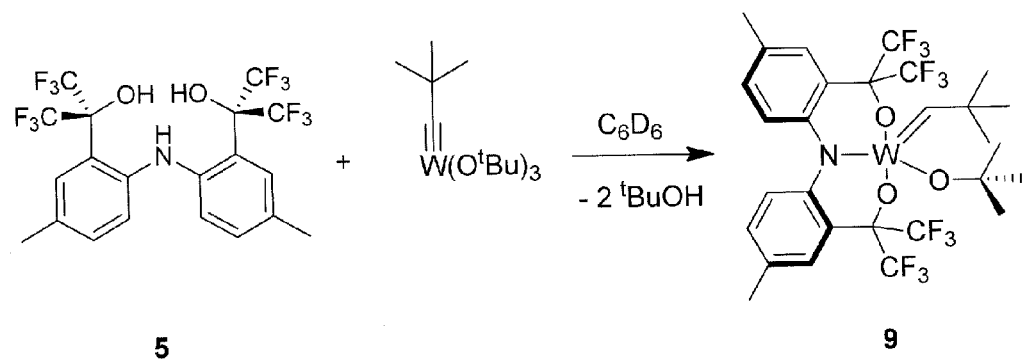
FIG. 28 is a scheme for the synthesis of [CF₃—ONO]W(≡CH$^t$Bu)(O$^t$Bu) (9) according to an embodiment of the invention.
Figure 29:
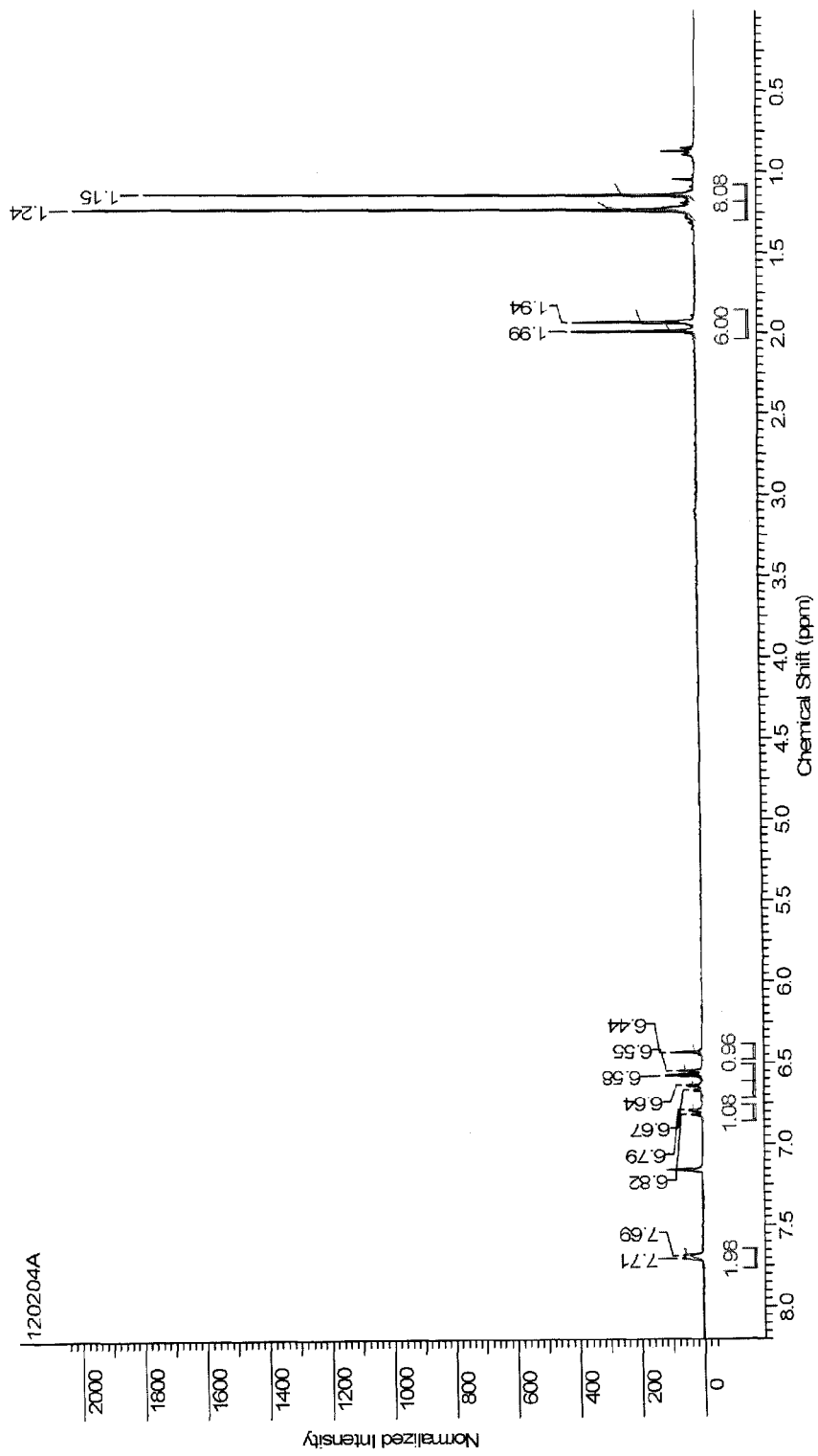
FIG. 29 is a ¹H NMR spectrum of 9 in CDCl₃.
Figure 30:
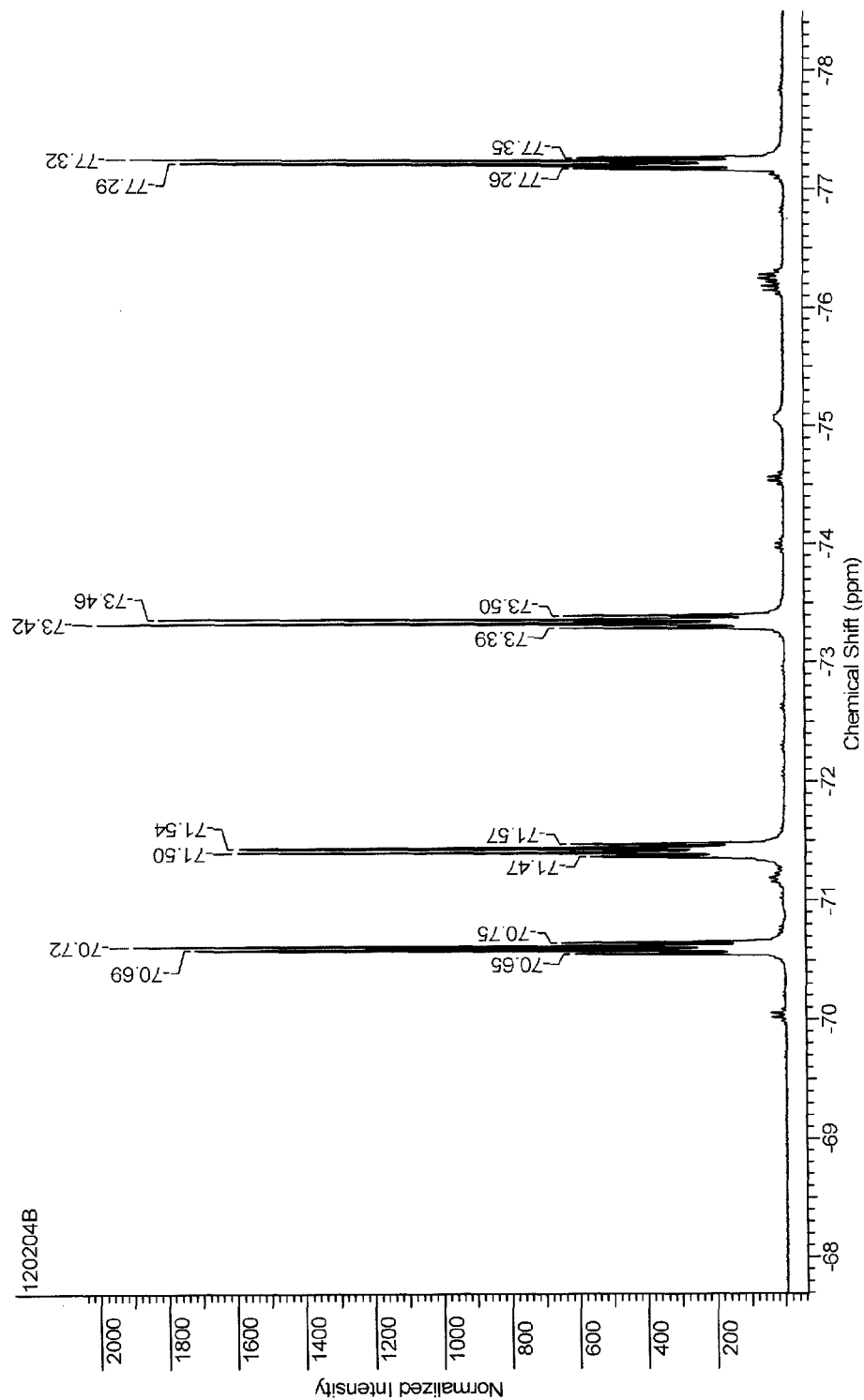
FIG. 30 is a ¹⁹F{¹H} NMR spectrum of 9 in CDCl₃.

As indicated in the reaction scheme shown in FIG. 28, to 2 mL of ($^t$BuO)$_3$W≡C$^t$Bu (0.289 g, 6.11×10$^{-4}$ mol) in benzene was added 2 mL of H$_3$[CF$_3$—ONO] (1) (0.324 g, 6.11×10$^{-4}$ mol) in benzene dropwise. The reaction mixture was stirred for 1 hour then dried under vacuum for 4 hours to yield a brown powder. The solid residue was dissolved in pentane (10 mL) and filtered. Cooling the filtrate to −35° C. yielded crystals of 9. Subsequently concentrating the filtrate via vacuum and cooling yielded more crystals of 9. The combined yield is 0.350 g (66%). $^1$H NMR (C$_6$D$_6$) (shown in FIG. 29): δ=7.71 (s, 1H, Ar—H), 7.69 (s, 1H, Ar—H), 6.81 (d, 1H, Ar—H, $^3$J=8.21 Hz), 6.66 (d, 1H, Ar—H, $^3$J=8.50 Hz), 6.57 (d, 2H, Ar—H, $^3$J=8.50 Hz), 6.44 (s, 1H, W=CH$^t$Bu, satellites $^2$J($^1$H, $^{183}$W)=8.80 Hz), 1.99 (s, 3H, Ar—CH$_3$), 1.94 (s, 3H, Ar—CH$_3$'), 1.24 (s, 9H, —OC(CH$_3$)$_3$), 1.15 (s, 9H, W=CHC(CH$_3$)$_3$) ppm. $^{19}$F{$^1$H} NMR (C$_6$D$_6$) (shown in FIG. 30): δ=−70.71 (q, 3F, $^4$J=8.48 Hz), −71.52 (q, 3F, $^4$J=10.90 Hz), −73.44 (q, 3F, $^4$J=10.90 Hz), −77.31 (q, 3F, $^4$J=8.48 Hz) ppm. $^{13}$C{$^1$H} NMR (C$_6$D$_6$, 500 MHz): δ=262.6 (s, W=CH$^t$Bu), 146.5 (s, Ar—C), 145.4 (s, Ar—C), 134.4 (s, Ar—C), 133.6 (s, Ar—C), 133.0 (s, Ar—C), 131.0 (s, Ar—C), 127.5 (s, Ar—C), 127.3 (s, Ar—C), 126.2 (s, Ar—C), 124.6 (m, CF$_3$), 124.3 (m, CF$_3$), 123.9 (s, Ar—C), 123.7 (m, CF$_3$), 123.5 (s, Ar—C), 90.4 (s, —OC(CH$_3$)$_3$), 84.3 (m, —C(CF$_3$)$_2$), 82.8 (m, —C(CF$_3$)$_2$), 41.0 (s, W=CHC(CH$_3$)$_3$), 35.0 (s, W=CHC(CH$_3$)$_3$), 29.2 (s, —OC(CH$_3$)$_3$), 20.3 (s, Ar—CH$_3$), 20.1 (s, Ar—CH$_3$') ppm. Anal. Calcd. for C$_{30}$H$_{33}$F$_{12}$NO$_3$W (867.18 g/mol): C, 41.54%; H, 3.83%; N, 1.61%. Found; C, 41.42%; H, 3.73; N, 1.59%.

Synthesis of {H$_3$CPPh$_3$}{[CF$_3$—ONO]W(≡C$^t$Bu)(O$^t$Bu)} (10)

Figure 3:
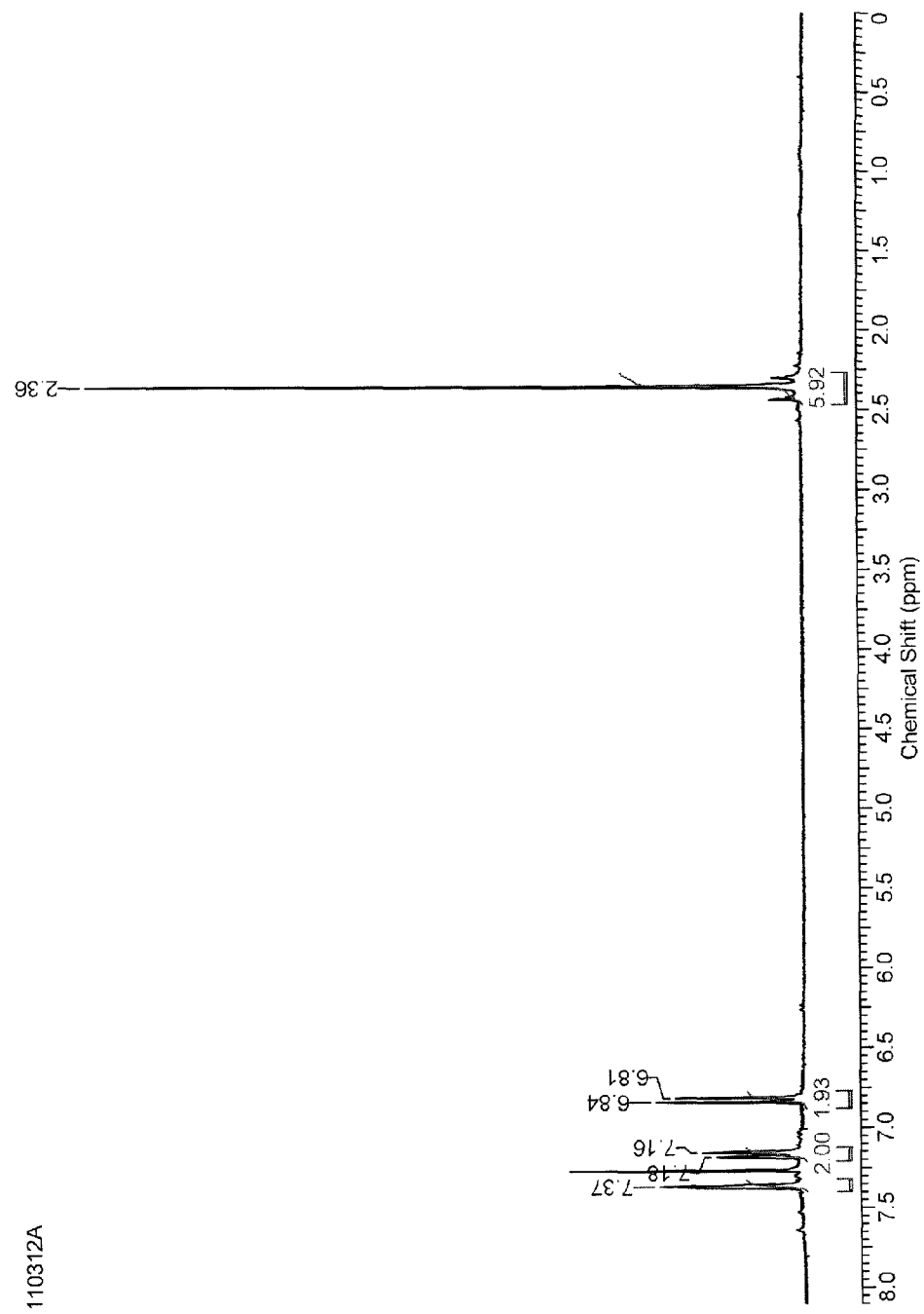
FIG. 3 is a $^1$H NMR spectrum of 5 in CDCl$_3$.
Figure 31:
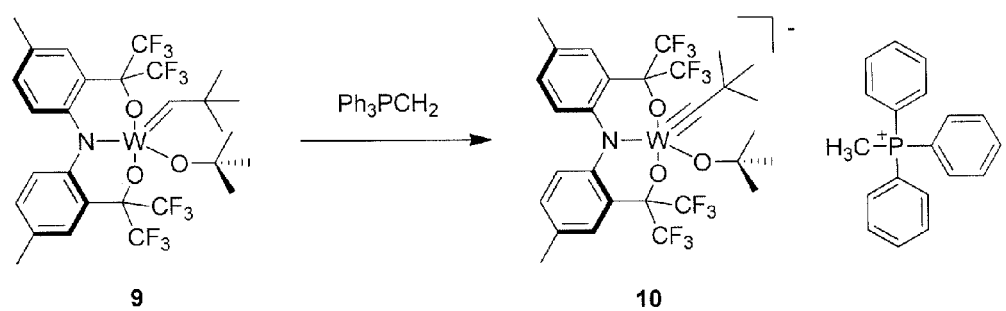
FIG. 31 is a scheme for the synthesis of {H₃CPPh₃}{[CF₃—ONO]W(≡C$^t$Bu)(O$^t$Bu)} (10) according to an embodiment of the invention.
Figure 35:
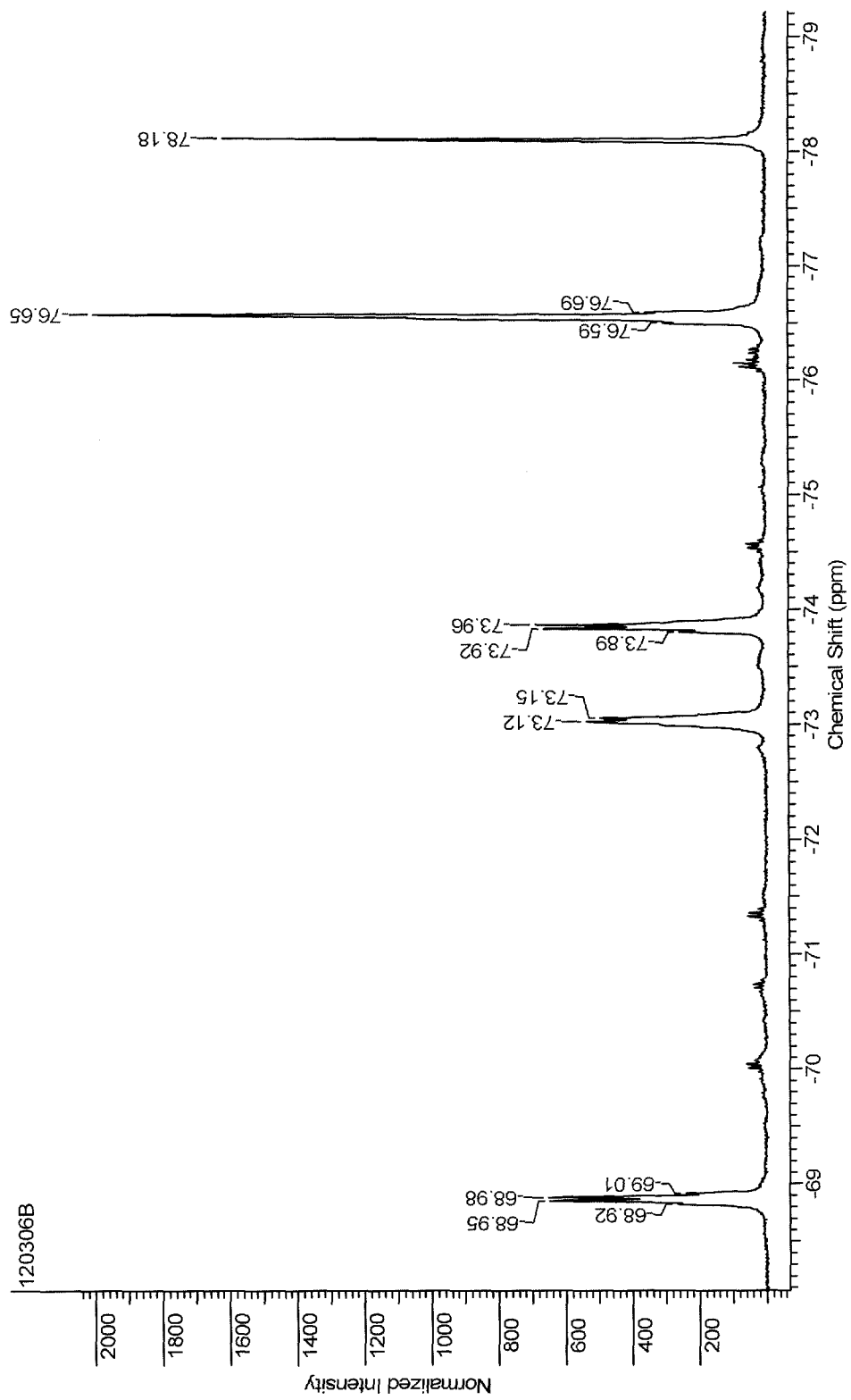
FIG. 35 is a ¹⁹F{¹H} NMR spectrum of 11 in CDCl₃.

As indicated in the reaction scheme shown in FIG. 31, to 3 mL 10 in pentane (0.277 g, 3.18×10$^{-4}$ mol) was added 4 ml, of PPh$_3$CH$_2$ in pentane (0.088 g, 3.18×10$^{-4}$ mol) dropwise. The product 10 precipitates from solution as an orange powder. The reaction mixture was stirred for 4 hours before the orange powder was filtered from the solution and dried under vacuum for 1 hour. The isolated yield was 0.228 g (80%). $^1$H NMR (C$_6$D$_6$): δ=7.76 (s, 1H, Ar—H), 7.61 (s, 1H, Ar—H), 7.47 (d, 1H, Ar—H, $^3$J=8.49 Hz), 6.95-7.15 (m, 16H, Ar—H), 6.92 (d, 1H, Ar—H, $^3$J=8.49 Hz), 6.75 (d, 1H, Ar—H, $^3$J=8.49 Hz), 2.36 (d, 3H, Ph$_3$PCH$_3$, $^2$J=13.31 Hz), 2.14 (s, 3H, Ar—CH$_3$), 2.06 (s, 3H, Ar—CH$_3$'), 1.66 (s, 9H, —OC(CH$_3$)$_3$), and 1.17 (s, 9H, W=CHC(CH$_3$)$_3$) ppm. $^{19}$F{$^1$H} NMR (C$_6$D$_6$) (shown in FIG. 35): δ=−68.67 (q, 3F, $^4$J=9.61 Hz), −71.19 (q, 3F, $^4$J=9.61 Hz), −74.39 (q, 3F, $^4$J=9.61 Hz), −76.20 (q, 3F, $^4$J=9.61 Hz). $^{31}$P{$^1$H} NMR (C$_6$D$_6$): δ=−21.6 ppm. $^{13}$C{$^1$H} NMR (C$_6$D$_6$, 500 MHz): δ=286.0 (s, W≡C$^t$Bu), 155.5 (s, Ar—C), 154.5 (s, Ar—C), 131.5 (s, Ar—C), 130.3 (s, Ar—C), 130.2 (s, Ar—C), 127.8 (s, Ar—C), 127.2 (s, Ar—C), 127.0 (s, Ar—C), 126.2 (s, Ar—C), 122.9 (s, Ar—C), 122.6 (s, Ar—C), 121.0 (s, Ar—C), 85.4 (m, —C(CF$_3$)$_2$), 83.6 (m, —C(CF$_3$)$_2$), 77.1 (s, —OC(CH$_3$)$_3$), 49.4 (s, W≡CC(CH$_3$)$_3$), 33.7 (s, W≡CC(CH$_3$)$_3$), 33.5 (s, —OC(CH$_3$)$_3$), 20.7 (s, Ar—CH$_3$), 20.5 (s, Ar—CH$_3$') ppm. Anal. Calcd. for C$_{48}$H$_{48}$F$_{12}$NO$_3$PW (1129.27 g/mol): C, 51.03%; H, 4.28%; N, 1.24%. Found; C, 50.98%; H, 4.38; N, 1.18%.

Synthesis of {H$_3$CPPh$_3$}$_2${[CF$_3$—ONO]W(≡C$^t$Bu)(OTf)$_2$} (11)

Figure 33:
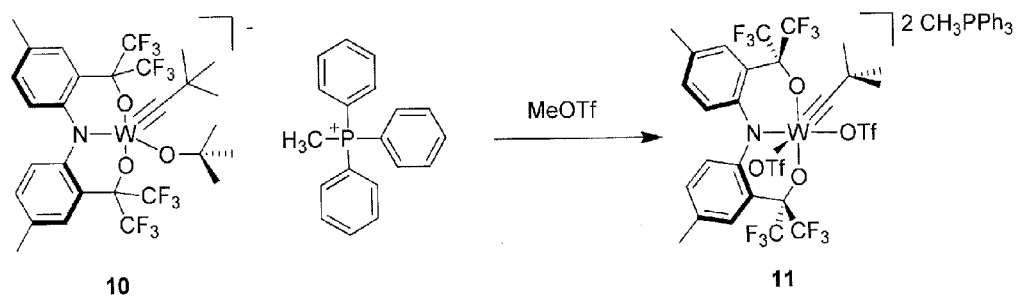
FIG. 33 is a scheme for the synthesis of {H₃CPPh₃}₂{[CF₃—ONO]W(≡C$^t$Bu)(OTf)₂} (11) according to an embodiment of the invention.
Figure 32:
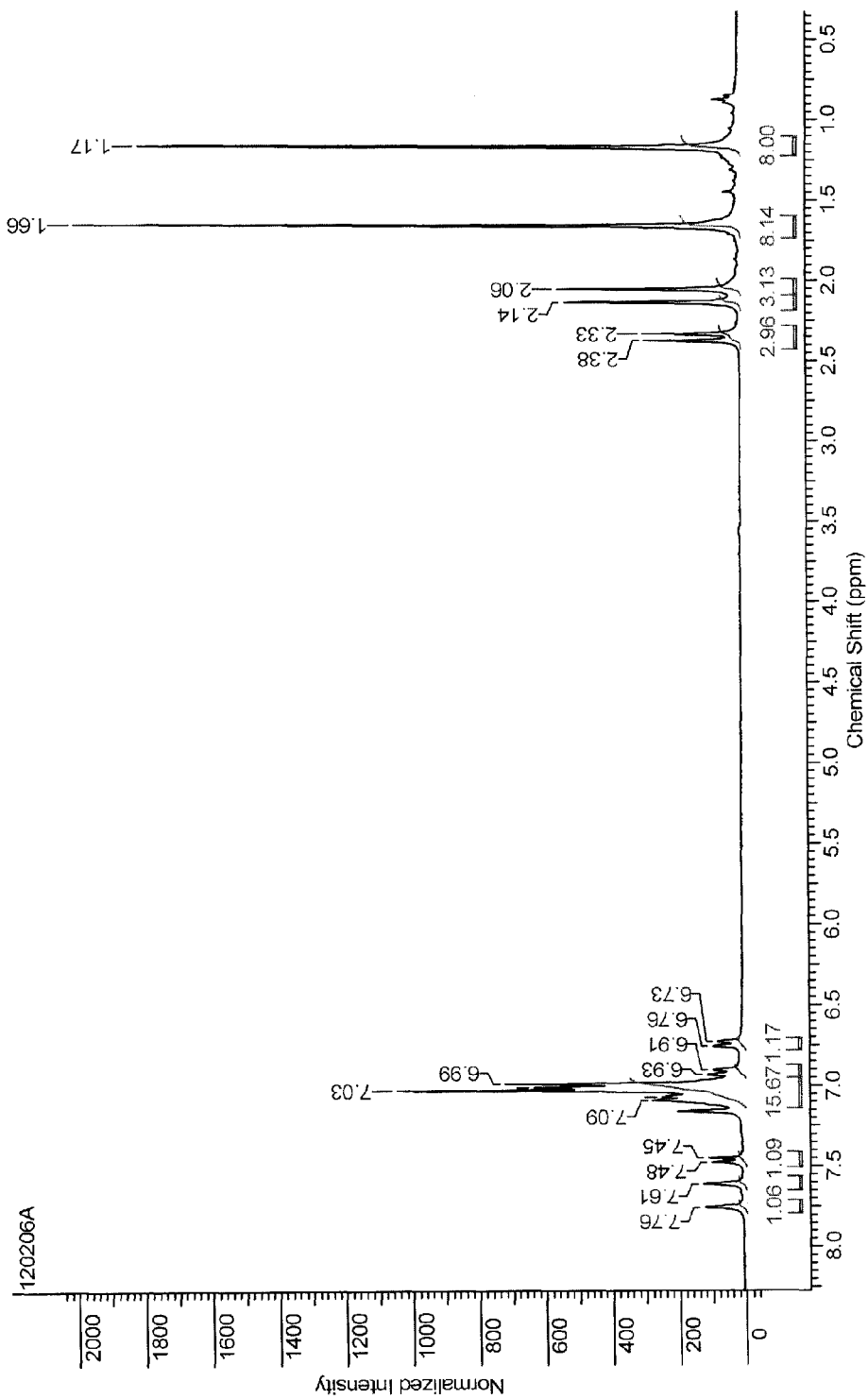
FIG. 32 is a ¹H NMR spectrum of 10 in CDCl₃.
Figure 34:
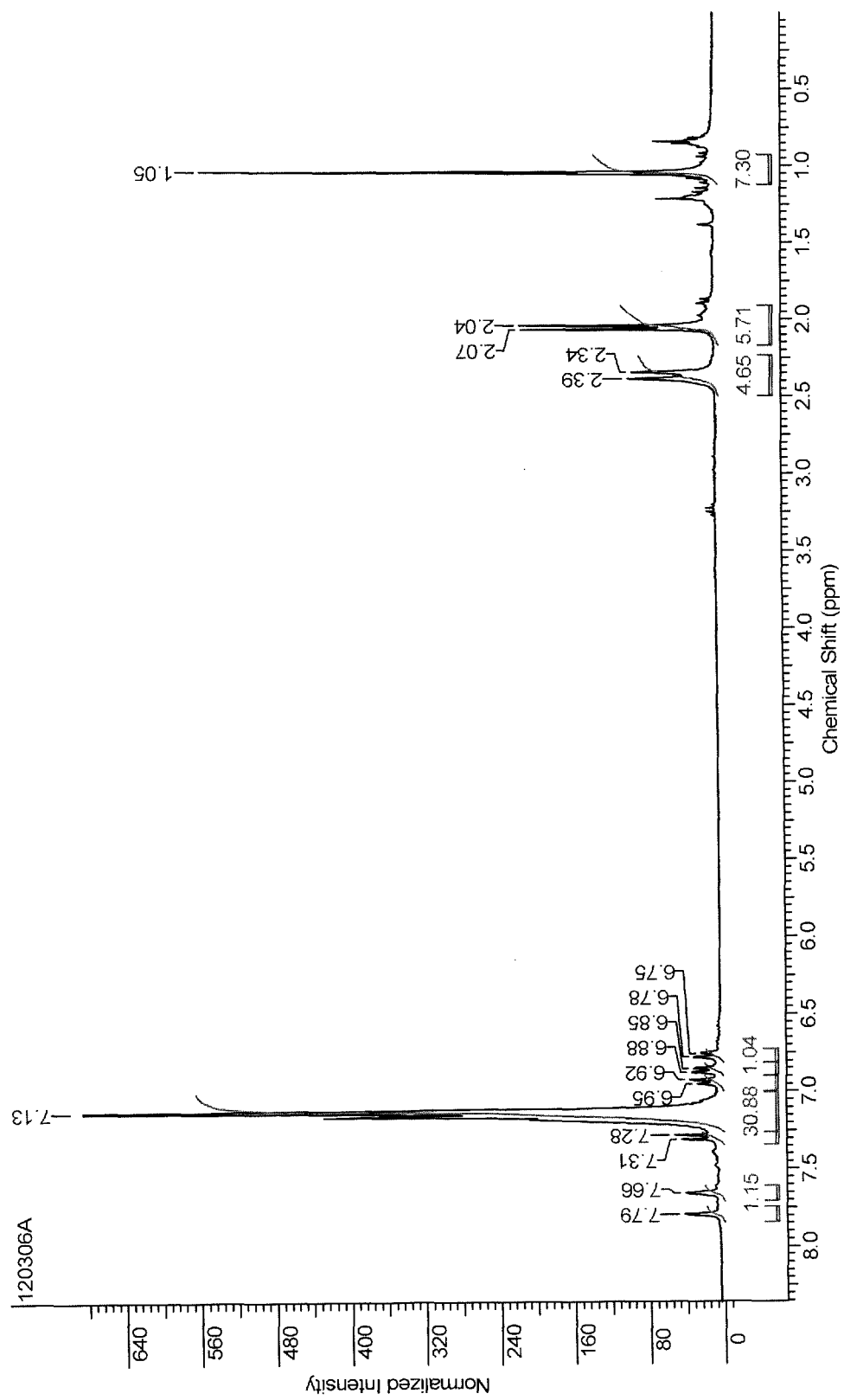
FIG. 34 is a ¹H NMR spectrum of 11 in CDCl₃.

As indicated in the reaction scheme shown in FIG. 33, to a benzene solution (2 mL) of 11 (0.125 g, 1.11×10$^{-4}$ mol) was added MeOTf (0.018 g, 1.11×10$^{-4}$ mol). The reaction mixture was stirred overnight, turning from a red solution to a deep blue solution. The solvent was stripped to a residual oil to which a minimal amount of benzene was added. Blue oil formed upon addition of hexanes to the benzene solution. The solvent was decanted and the oil dried under vacuum. $^1$H NMR (C$_6$D$_6$) (shown in FIG. 34): δ=7.79 (s, 1H, Ar—H), 7.66 (s, 1H, Ar—H), 7.30 (d, 1H, Ar—H, $^3$J=8.21 Hz), 7.10-7.20 (br, 30H, (C$_6$H$_5$)$_3$PCH$_3$), 6.94 (d, 1H, Ar—H, $^3$J=8.50 Hz), 6.87 (d, 1H, Ar—H, $^3$J=8.21 Hz), 6.77 (d, 1H, Ar—H, $^3$J=8.50 Hz), 2.37 (d, 1H, Ph$_3$PCH$_3$, $^2$J=13.19 Hz), 2.07 (s, 1H, Ar—CH$_3$), 2.04 (s, 1H, Ar—CH$_3$'), 1.05 (s, 9H, WCC(CH$_3$)$_3$) ppm. $^{19}$F{$^1$H} NMR (C$_6$D$_6$) (shown in FIG. 35): δ=−68.97 (q, 3F, $^4$J=8.48 Hz), −73.14 (q, 3F, $^4$J=8.48 Hz), −73.94 (q, 3F, $^4$J=9.69 Hz), −76.64 (q, 3F, $^4$J=9.69 Hz), −76.65 (s, 3F, —OSO$_2$CF$_3$), −78.18 (s, 3F, —OSO$_2$CF$_3$) ppm.

Synthesis of [CF$_3$—ONO]W[C($^t$Bu)C(Me)C(Ph)] (12)

Figure 36:
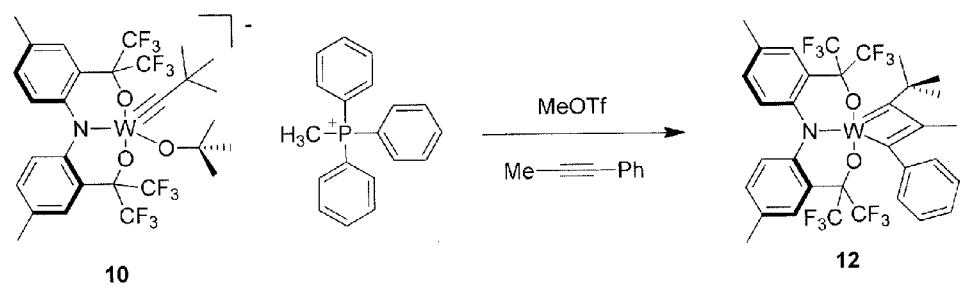
FIG. 36 is a scheme for the synthesis of [CF₃—ONO]W[C($^t$Bu)C(Me)C(Ph)] (12) according to an embodiment of the invention.

As indicated in the reaction scheme shown in FIG. 36, a diethyl ether solution (3 mL) containing 9 (0.139 g, 1.23×

Figure 37:
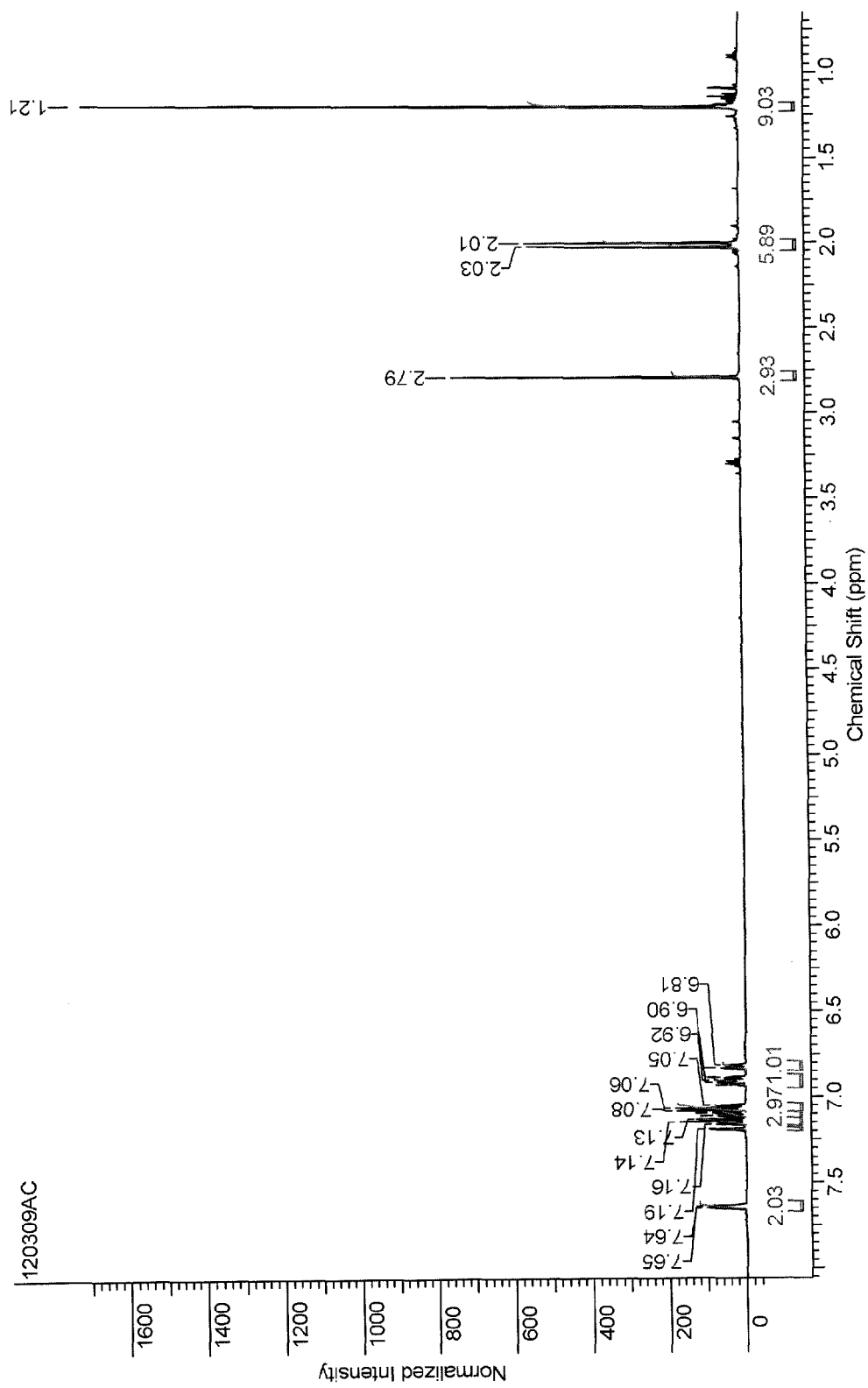
FIG. 37 is a ¹H NMR spectrum of 12 in C₆D₆.
Figure 38:
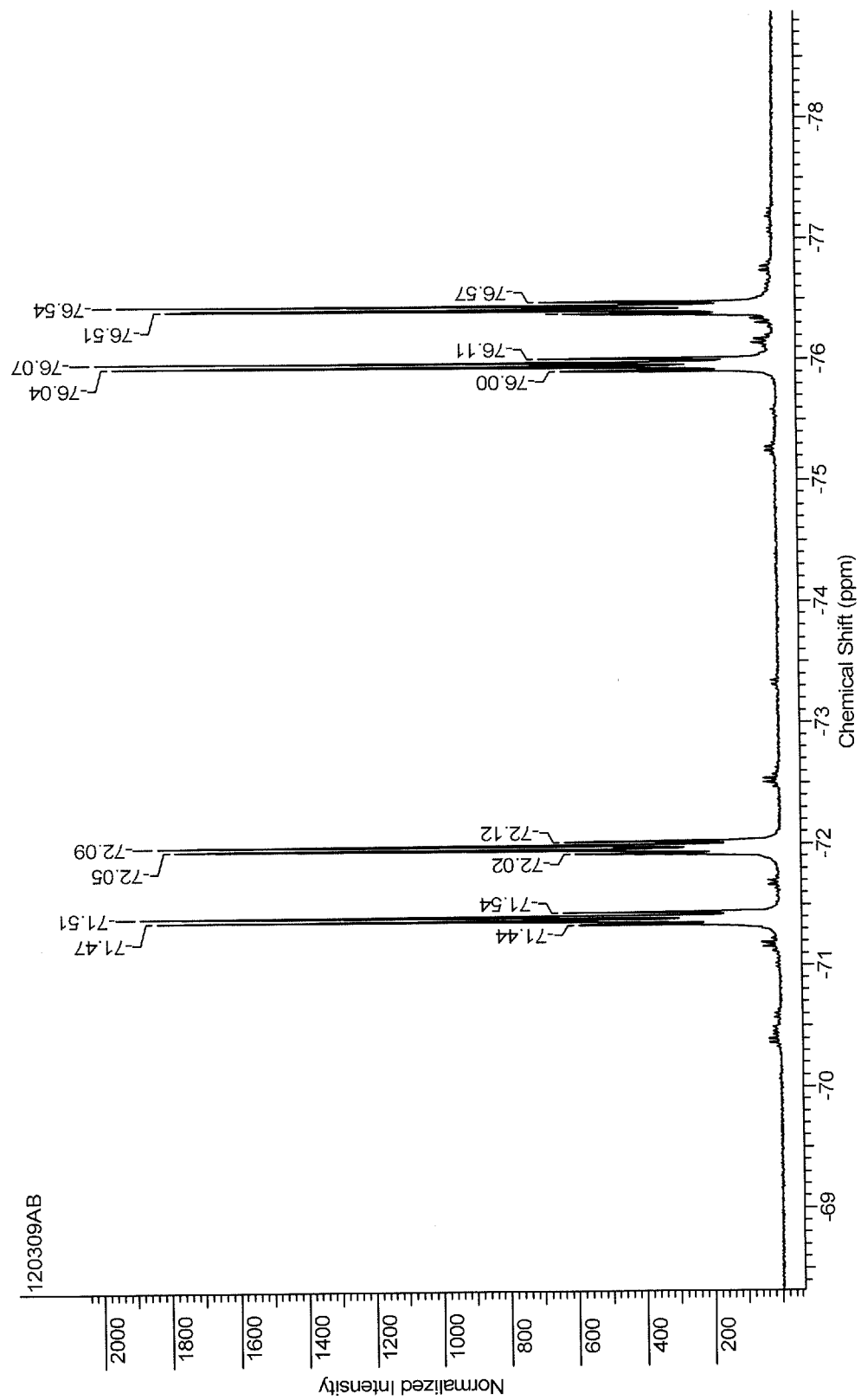
FIG. 38 is a ¹⁹F{¹H} NMR spectrum of 12 in C₆D₆.
Figure 39:
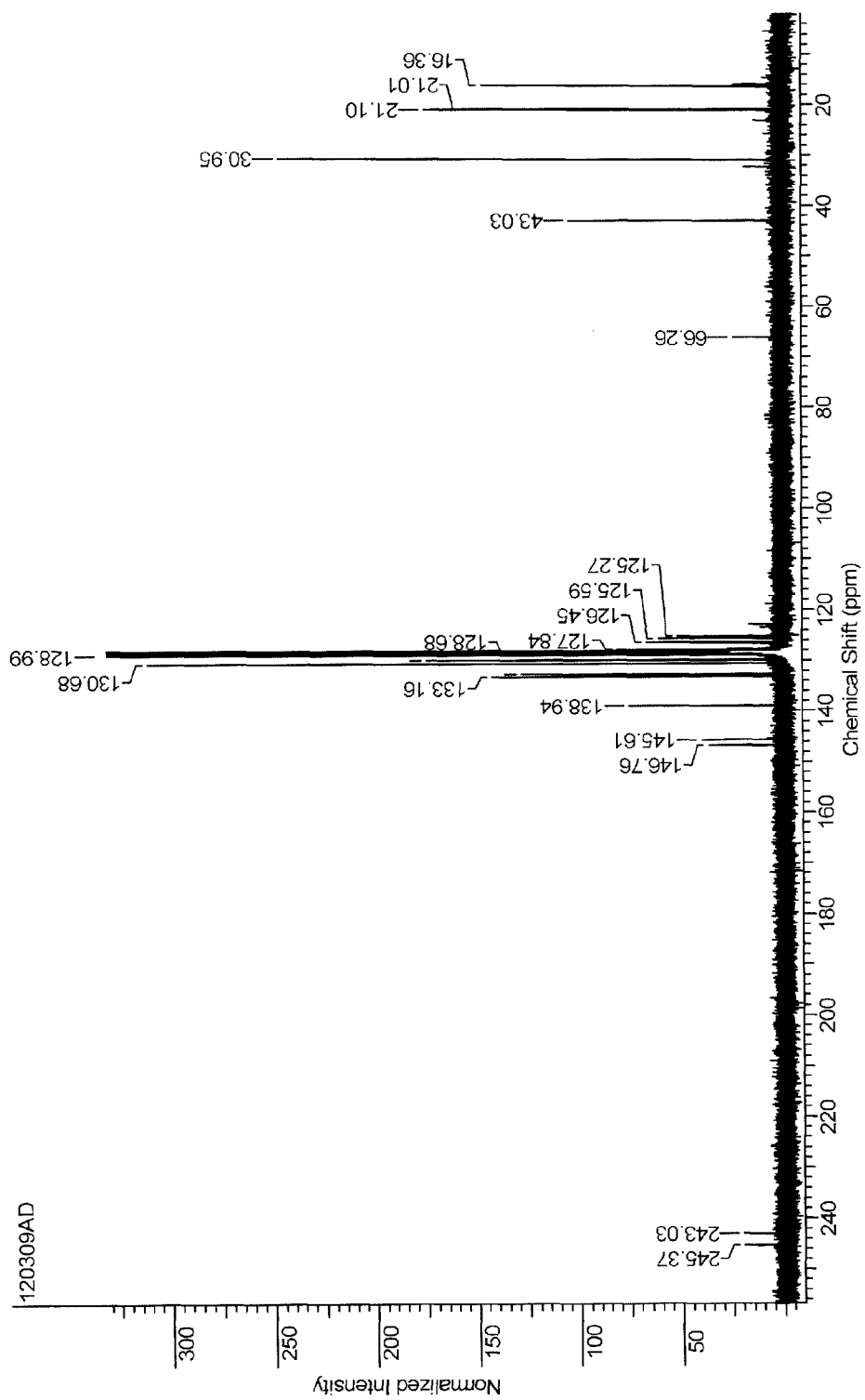
FIG. 39 is a ¹³C{¹H} NMR spectrum of 12 in C₆D₆.

10$^{-4}$ mol), MeOTf (0.020 g, 1.23×10$^{-4}$ mol) and PhC≡CCH$_3$ (0.014 g, 1.23×10$^{-4}$ mol) was prepared and stirred overnight. The solution was filtered and the filtrate reduced under vacuum. The residue was dissolved in pentane, filtered, and reduced to a solid residue. The solid residue was rinsed with pentane. The solid residue was dissolved in Et$_2$O and slow evaporated to yield crystals of 12 (0.038 g). Additionally, the slow evaporation of pentane washings yielded crystals of 12 (0.020 g) for an overall yield of 51%. Crystals suitable for single crystal X-ray diffraction were grown by slow evaporation of a pentane solution of 12. $^1$H NMR (C$_6$D$_6$, 500 MHz) (shown in FIG. 37): δ=7.62 (s, 1H, Ar—H), 7.61 (s, 1H, Ar—H), 7.12 (t, 2H, Ar—H, $^3$J=7.55 Hz), 7.08 (d, 1H, Ar—H, $^3$J=8.37 Hz), 7.02-7.05 (m, 3H, Ar—H), 6.90 (d, 1H, $^3$J=7.55 Hz), 6.87 (d, 1H$^{13}$J=8.10 Hz), 6.80 (d, 1H$^{13}$J=8.37 Hz), 2.76 (s, 3H, WC$_3$(CH$_3$)), 2.00 (s, 3H, Ar—CH$_3$), 1.98 (s, 3H, Ar—CH$_3$'), 1.18 (s, 9H, WC$_3$C(CH$_3$)$_3$) ppm. $^{19}$F{$^1$H} NMR (C$_6$D$_6$, 300 MHz) (shown if FIG. 38): δ=−71.49 (q, 3F, $^4$J=9.69 Hz), −72.07 (q, 3F, $^4$J=9.69 Hz), −76.06 (q, 3F, $^4$J=9.69 Hz), −76.53 (q, 3F, $^4$J=9.69 Hz) ppm. $^{13}$C{$^1$H} NMR (C$_6$D$_6$, 500 MHz) (shown in FIG. 39): δ=245.37 (s, W≡C), 243.03 (s, W≡C), 146.76 (s, Ar—C), 145.61 (s, Ar—C), 138.94 (s, Ar—C), 133.16 (s, Ar—C), 132.69 (s, Ar—C), 130.68 (s, Ar—C), 129.94 (s, Ar—C), 128.99 (s, Ar—C), 128.68 (s, Ar—C), 127.84 (s, Ar—C), 126.45 (s, Ar—C), 66.26 (s, WC$_3$C(CH$_3$)$_3$), 43.03 (s, WC$_3$CH$_3$), 30.95 (s, WC$_3$C(CH$_3$)$_3$), 21.10 (s, Ar—CH$_3$), 16.36 (s, Ar—CH$_3$") ppm. Anal. Calcd. for C$_{35}$H$_{31}$F$_{12}$NO$_2$W (909.45 g/mol): C, 46.22%; H, 3.44%; N, 1.54%. Found; C, 46.31%; H, 3.50; N, 1.60%.

Figure 40:
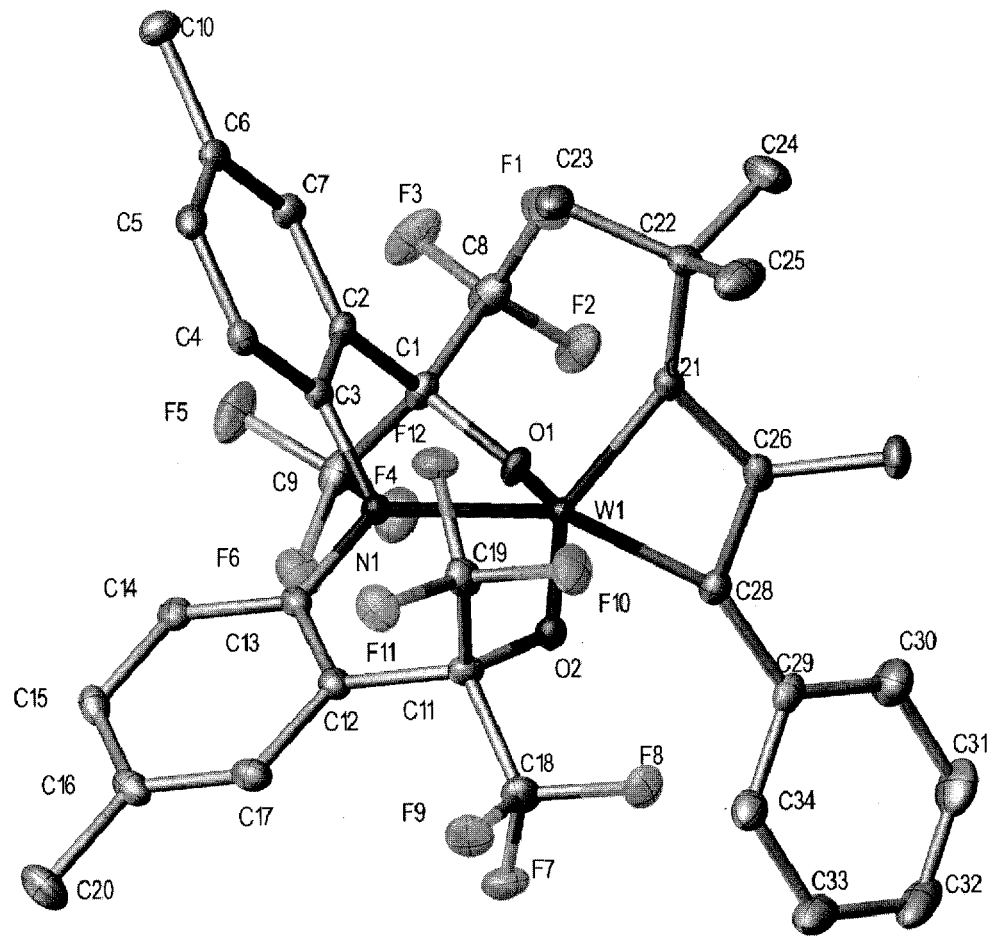
FIG. 40 shows the solid state structure of 12 with thermal ellipsoids drawn at the 50% probability level.

X-Ray Experimental for 12:

X-Ray Intensity data were collected at 100 K on a Bruker DUO diffractometer using MoKα radiation (λ=0.71073 Å) and an APEXII CCD area detector. Raw data frames were read by program SAINT[1] and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces. The structure (shown in FIG. 40) was solved and refined in SHELXTL6.1, using full-matrix least-squares refinement. The non-H atoms were refined with anisotropic thermal parameters and all of the H atoms were calculated in idealized positions and refined riding on their parent atoms. In the final cycle of refinement, 7644 reflections (of which 6905 are observed with I>2σ(I)) were used to refine 457 parameters and the resulting R$_1$, wR$_2$ and S (goodness of fit) were 1.45%, 3.69% and 1.051, respectively. The refinement was carried out by minimizing the wR$_2$ function using F$^2$ rather than F values. R$_1$ is calculated to provide a reference to the conventional R value but its function is not minimized. A toluene molecule was disordered and could not be modeled properly; thus program SQUEEZE, a part of the PLATON package of crystallographic software, was used to calculate the solvent disorder area and remove its contribution to the overall intensity data. FIG. 41 give the crystal data and structure refinement for 12. FIG. 42 gives atomic coordinates and equivalent isotropic displacement parameters for 12. FIG. 43 gives bond lengths and angles for 12. FIG. 44 gives anisotropic displacement parameters for 12.

Synthesis of 2,5-bis(3-(tert-butyl)-2-methoxyphenyl)-1H-pyrrole, [pyr-ONO]Me$_2$ (13)

Figure 45:
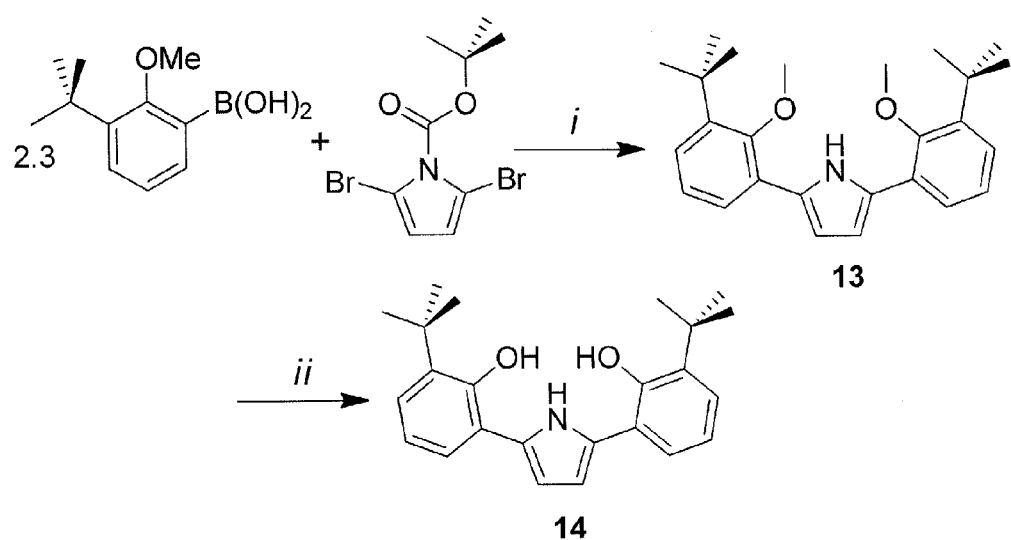
FIG. 45 is a scheme for the synthesis of 6,6'-(1H-pyrrole-2,5-diyl)bis(2-(tert-butyl)phenol), [pyr-ONO]H₃ (14), according to an embodiment of the invention.

As indicated in FIG. 45, in an argon-filled glove box, a toluene solution (15 mL) containing (3-(tert-butyl)-2-methoxyphenyl)boronic acid (0.660 g, 3.17×10$^{-3}$ mol, 2.3 equiv), tetrakis(triphenylphosphine)-palladium(0) (0.159 g, 1.38×10$^{-4}$ mol, 0.10 equiv), Na$_2$CO$_3$ (1.16 g, 1.09×10$^{-2}$ mol, 7.9 equiv), KCl (0.308 g, 4.13×10$^{-3}$ mol, 3 equiv), and tert-butyl-2,5-dibromo-1H-pyrrole-1-carboxylate (0.448 g, 1.38×10$^{-3}$ mol, 1 equiv) was prepared. The reaction flask was fitted with a Liebig condenser and Y-adapter prior to exiting the glovebox and attached to an argon Schlenk line. Under counter argon pressure, 15 mL of degassed ethanol-water (2:1) solution was added to the reaction flask. The reaction mixture was heated at 96° C. with stirring for 20 h, and during that time the solution changed from yellow to orange-red color. The reaction mixture was allowed to cool, and then solvent was removed under reduced pressure. The residue was dissolved in CH$_2$Cl$_2$ (15 mL) and washed with water and brine. The organic layer was dried with MgSO$_4$, and the solvent was removed under reduced pressure. To the residue, 20 mL of hexanes was added to precipitate a white solid. The mixture was stirred for 0.5 h before filtering off the white solid. The collected filtrate was reduced under vacuum to yield an orange oil containing the BOC protected pyrrole. The BOC protecting group is easily removed upon stirring the residue with 10 mL of 4 M HCl in 1,4-dioxane at 45° C. for 18 h. The solvent was removed under reduced pressure. The residue was dissolved in CH$_2$Cl), washed with saturated Na$_2$CO$_3$, and then water. The organic layer was dried with MgSO$_4$ prior to removing the solvent under reduced pressure. The purple oily residue was dissolved in minimal 2-propanol (5 mL). Cooling the 2-propanol solution precipitates crystals of the product, 2,5-bis(3-(tert-butyl)-2-methoxyphenyl)-1H-pyrrole (Yield=0.219 g, 47%). $^1$H NMR (CDCl$_3$, 500 MHz): δ=9.90 (b, 1H, NH), 7.42 (dd, 2H, $^3$J=7.6 Hz, $^4$J=1.7 Hz, Ar—H), 7.24 (dd, 2H, $^3$J=7.9 Hz, $^4$J=1.7 Hz, Ar—H), 7.07 (t, 2H, $^3$J=7.8 Hz, Ar—H), 6.55 (d, 2H, $^4$J=2.7 Hz, Pyr-H), 3.57 (s, 6H, —OCH$_3$), 1.46 (s, 18H, —C(CH$_3$)$_3$) ppm. $^{13}$C{$^1$H} NMR (CDCl$_3$, 126 MHz): δ=156.3 (s, Ar C), 143.4 (s, Ar C), 130.0 (s, Ar C), 127.4 (s, Ar C), 126.9 (s, Pyr C), 125.5 (s, Ar C), 123.8 (s, Ar C), 108.1 (s, Pyr C), 60.8 (s, —OCH$_3$), 35.2 (s, —C(CH$_3$)$_3$), 31.0 (s, —C(CH$_3$)$_3$) ppm. Anal. Calcd. for C$_{26}$H$_{33}$NO$_2$: C, 79.76%; H, 8.50%; N, 3.58%. Found; C, 79.35%; H: 8.11%; N, 3.79%.

Synthesis of 6,6'-(1H-pyrrole-2,5-diyl)bis(2-(tert-butyl)phenol), [pyr-ONO]H$_3$ (14)

As indicated in FIG. 45, in a glovebox, a 250 mL two-neck flask equipped with a stirbar, condenser, and Y-adapter was charged with 2-(diethylamino)ethanethiol hydrochloride (0.867 g, 6.12×10$^{-3}$ mol, 2.4 equiv) and NaO$^t$Bu (1.24 g, 1.29×10$^{-2}$ mol, 5.0 equiv). The apparatus was brought out of the glovebox, attached to a Schlenk line, and cooled with an ice-water bath. Anhydrous DMF (10 mL), which was also cooled in an ice-water bath, was added to the reaction flask. After 5 min, the reaction mixture was allowed to warm to room temperature. After stirring for additional 15 min, 2,5-bis(3-(tert-butyl)-2-ethoxyphenyl)-1H-pyrrole (1.00 g, 2.55×10$^{-3}$ mol, 1.0 equiv) was added in one portion under counter argon flow, and the reaction mixture was refluxed for 3 h. The mixture was allowed to cool to ambient temperature, and then placed in an ice-water bath. Under counter argon flow, the reaction mixture was neutralized by adding 1 M HCl drop-wise until the pH reaches 1.0, and then diluted with water (25 mL). The aqueous phase was extracted with ethyl acetate (3×25 mL). The combined organic extracts were washed with water (3×10 mL), saturated brine solution (10 mL), and then dried over MgSO₄. The solvent was removed under vacuum to give a brown oil that was recrystallized from cold pentane to afford a beige microcrystalline powder (Yield=0.34 g, 36%). $^1$H NMR (CDCl₃, 500 MHz) δ (ppm): 8.98 (br, 1H, NB), 7.25 (d, 4H, $^3$J=7.60 Hz, Ar—H), 6.92 (t, 2H, $^3$J=7.60 Hz, Ar—H), 6.57 (d, 2H, $^4$J=5.78 Hz, Pyr-H), 6.12 (s, 2H, —OH), 1.46 (s, 18H, C(CH₃)₃). $^{13}$C{$^1$H} NMR (CDCl₃, 126 MHz): δ=151.3 (s, Ar C), 136.4 (s, Ar C), 129.0 (s, Pyr C), 126.3 (s, Ar C), 125.8 (s, Ar C), 120.2 (s, Ar C), 120.1 (s, Ar C), 108.6 (s, Pyr C), 34.7 (s, C(CH₃)₃), 29.7 (s, C(C—H₃)₃). Anal. Calcd for C₂₄H₂₉NO₂: C, 79.30; H, 8.04; N, 3.85. Found: C, 79.23; H, 7.97; N, 3.76.

Synthesis of [pyr-ONO]W≡CH$^t$Bu(O$^t$Bu) (15)

Figure 46:
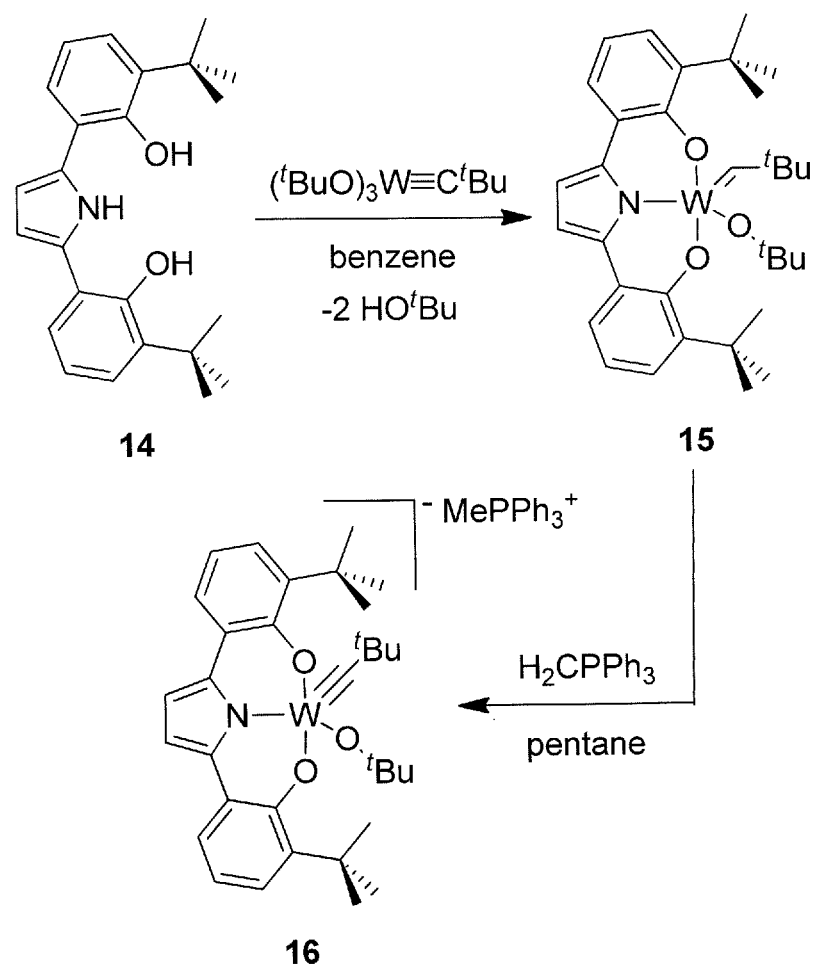
FIG. 46 is a scheme for the synthesis of [pyr-ONO]W≡CH$^t$Bu(O$^t$Bu) (15), according to an embodiment of the invention, and, subsequently, {MePPh₃}{[pyr-ONO]W≡C$^t$Bu(O$^t$Bu)} (16), according to an embodiment of the invention.

As indicated in FIG. 46, a benzene solution (2 mL) containing 14 (0.087 g, 2.38×10⁻⁴ mol, 1 equiv) was added drop-wise to a benzene (1 mL) solution of ($^t$BuO)W≡C$^t$Bu (0.112 g, 2.38×10⁻⁴ mol, 1 equiv). The reaction mixture was allowed to stir for 0.5 h; during that time, the solution color turned to deep violet. All volatiles were evaporated under vacuum for 1 h. The violet powder was dissolved in pentane and filtered. The filtrate was collected and concentrated to 1 mL. Cooling the solution to −35° C. precipitates crystals of 15. A second batch of crystals was obtained after further concentrating and once again cooling the solution to −35° C. (Yield=0.074 g, 45%). $^1$H NMR (C₆D₆, 500 MHz): δ=8.27 (d, 2H, Ar—H, $^3$J=7.57 Hz), 7.77 (s, 2H, Pyr-H), 7.67 (s, 1H, W=CH$^t$Bu), 7.24 (d, 2H, Ar—H, $^3$J=6.83 Hz), 7.16 (t, 2H, Ar—H, $^3$J=7.57 Hz), 1.79 (s, 9H, W=CHC(CH₃)₃), 1.65 (s, 18H, Ar—C(CH₃)₃), and 0.50 (s, 9H, —OC(CH₃)₃) ppm. $^{13}$C{$^1$H} NMR (C₆D₆, 126 MHz): δ=268.61 (s, W=CH$^t$Bu), 149.6 (s, Ar C), 139.2 (s, Ar C), 138.3 (s, Pyr C), 127.3 (s, Ar C), 124.5 (s, Ar C), 122.5 (s, Ar C), 113.5 (s, Pyr C), 80.4 (s, —OC(CH₃)₃), 46.0 (s, WCHC(CH₃)₃), 36.0 (s, Ar—C(CH₃)₃), 34.4 (s, —C(CH₃)₃), 33.5 (s, —C(CH₃)₃), and 31.3 (s, Ar—C(CH₃)₃) ppm. Anal. Calcd. for C₃₃H₄₅NO₃W: C, 57.65%; H, 6.60%; N, 2.04%. Found: C, 57.54%; H, 6.53%; N, 2.02%.

Synthesis of {MePPh₃} {[pyr-ONO]W≡C$^t$Bu (O$^t$Bu)} (16)

Figure 47:
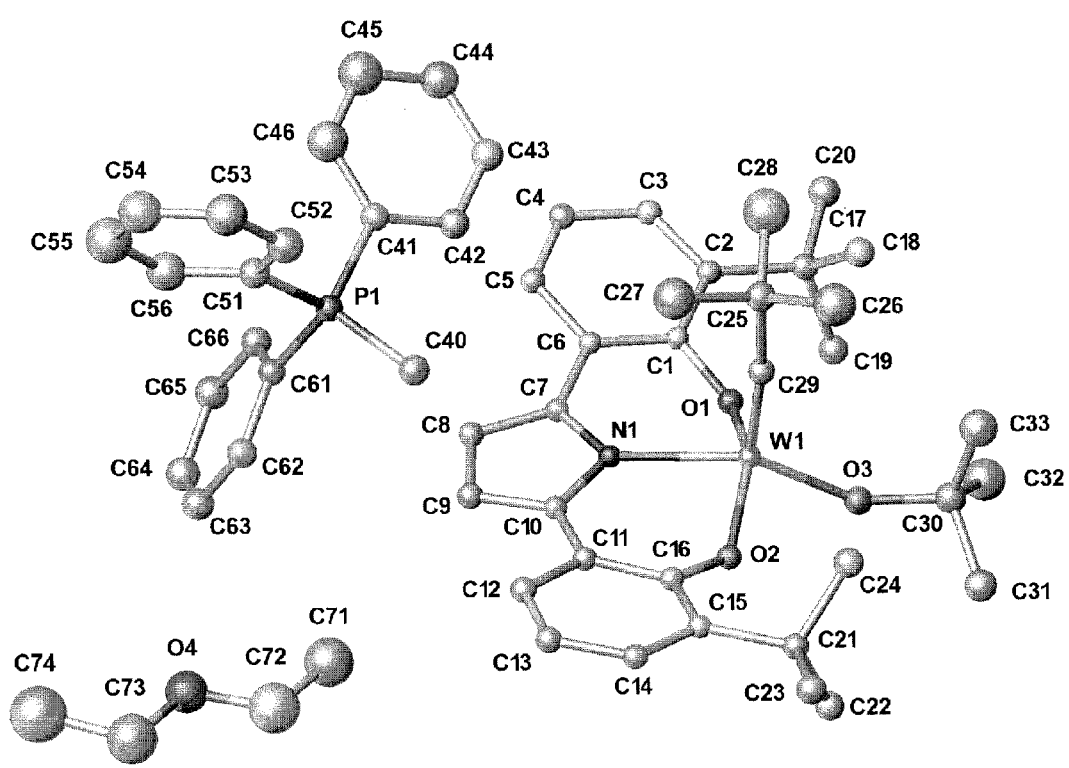
FIG. 47 shows the solid state structure of 16 as determined by X-ray crystallography.

As indicated if FIG. 46, a pentane solution (5 mL) of Ph₃PCH₂ (0.025 g, 9.1×10⁻⁵ mol, 1.1 equiv) was added drop-wise to a stirring pentane solution of 15 (0.056 g, 8.2×10⁻⁵ mol, 1.0 equiv) resulting in the precipitation of a yellow powder. The mixture was stirred for 4 h and the solid was separated by filtration, and washed with fresh pentane. The paste-like solid was dried under vacuum for 1 h to afford a fine white powder (Yield=0.061 g, 79%). $^1$H NMR (CDCl₃, 500 MHz): δ=7.70 (t, 3H, $^3$J=7.32 Hz, Ar—H), 7.50-7.53 (m, 6H, Ar—H), 7.43 (d, 2H, $^3$J=7.57 Hz, Ar—H), 7.24-7.29 (m, 6H, Ar—H), 6.97 (d, 2H, $^3$J=7.57 Hz, Ar—H), 6.63 (t, 2H, $^3$J=7.57 Hz, Ar—H), 6.57 (s, 2H, Pyr-H), 2.25 (d, 3H, CH₃PPh₃, $^2$J$_{HP}$=12.69 Hz), 1.65 (s, 9H, W≡CC (CH₃)₃), 1.49 (s, 18H, Ar—C(CH₃)₃), and 0.65 (s, 9H, —OC(CH₃)₃) ppm. $^{31}$P{$^1$H} NMR (CDCl₃, 121 MHz): δ=20.9 ppm. $^{13}$C{$^1$H} NMR (CDCl₃, 126 MHz): δ=301.1 (s, WC$^t$Bu), 159.2 (s, Ar C), 137.8 (s, Ar C), 135.7 (s, Pyr C), 135.0 (s, Ar C), 132.8 (d, Ar C, $^3$J$_{CP}$=10.6 Hz), 130.3 (d, Ar C, $^2$J$_{CP}$=13.2 Hz), 126.9 (s, Ar C), 122.8 (s, Ar C), 121.2 (s, Ar C), 118.8 (d, J$_{CP}$=90.0 Hz, Ar C), 117.6 (s, Ar C), 106.4 (s, Pyr C), 76.8 (s, OCMe₃), 49.7 (s, W≡CC(CH₃)₃), 35.3 (s, Ar—C(CH₃)₃), 33.7 (s, OC(CH₃)₃), 33.3 (s, W≡CC (CH₃)₃), 30.4 (s, Ar—C(CH₃)₃), and 8.1 (d, H₃CPPh₃, $^1$J$_{PC}$=56.9 Hz) ppm. Anal. Calcd. for C₅₂H₆₂NO₃PW: C, 64.80%; H, 6.48%; N, 1.45%. Found: C, 64.73%; H, 6.39%; N, 1.39%. The molecular structure of 16 as a co-crystal with diethyl ether by x-ray diffraction is shown in FIG. 47.

X-Ray Analysis of 16

X-Ray Intensity data were collected at 100 K on a Bruker DUO diffractometer using MoKα radiation (λ=0.71073 Å) and an APEXII CCD area detector. Raw data frames were read by program SAINT and integrated using 3D profiling algorithms. The resulting data were reduced to produce hid reflections and their intensities and estimated standard deviations. The data were corrected for Lorentz and polarization effects and numerical absorption corrections were applied based on indexed and measured faces. The structure was solved and refined in SHELXTL6.1, using full-matrix least-squares refinement. The non-H atoms were refined with anisotropic thermal parameters and all of the H atoms were calculated in idealized positions and refined riding on their parent atoms. The asymmetric unit consists of the W1 complex anion, a triphenylmethylphospate cation and an ether solvent molecule. In the final cycle of refinement, 12092 reflections (of which 8643 are observed with I>2σ(I)) were used to refine 583 parameters and the resulting R₁, wR₂ and S (goodness of fit) were 3.47%, 5.63% and 1.008, respectively. The refinement was carried out by minimizing the wR₂ function using F² rather than F values. R₁ is calculated to provide a reference to the conventional R value but its function is not minimized. SHELXTL6 (2008). Bruker-AXS, Madison, Wis., USA. FIGS. 48-52 gives the pertinent x-ray data for the 16 co-crystal.

It should be understood that the examples and embodiments described herein are for illustrative purposes only and that various modifications or changes in light thereof will be suggested to persons skilled in the art and are to be included within the spirit and purview of this application.

We claim:

1. An ONO trianionic pincer ligand precursor, consisting of a tri-protonated ONO trianionic pincer ligand precursor with OH and NH functionality, wherein each O⁻ from the OH is separated from the N⁻ from the NH by three bridging carbons, wherein the O⁻s and the N⁻ and the bridging carbons are capable of assuming a coplanar substructure:

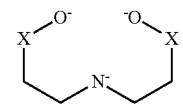

where X is C, and wherein the tri-protonated ONO trianionic pincer ligand precursor with OH and NH functionality has the structure:

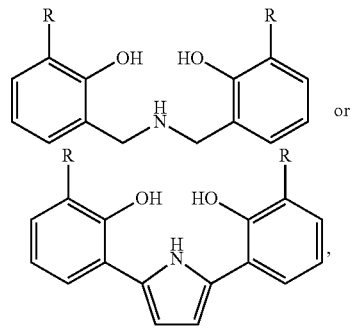

wherein R is independently $C_2$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $_2$-$C_{30}$ alkylester, $C_3$-$C_{30}$ alkenylester, $C_3$-$C_{30}$ alkynylester, or perfluorinated, partially fluorinated variations thereof.

2. The ONO trianionic pincer ligand precursor of claim 1, consisting of a tri-protonated ONO trianionic pincer ligand precursor with OH and NH functionality, wherein each O⁻ from the OH is separated from the N⁻ from the NH by three bridging carbons, wherein the O⁻s and the N⁻ and the bridging carbons are capable of assuming a coplanar substructure:

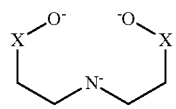

where X is C, and wherein the tri-protonated ONO trianionic pincer ligand precursor with OH and NH functionality has the structure:

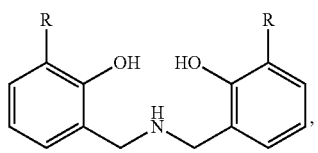

wherein R is independently $C_2$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $_2$-$C_{30}$ alkylester, $C_3$-$C_{30}$ alkenylester, $C_3$-$C_{30}$ alkynylester, or perfluorinated, partially fluorinated variations thereof.

3. The ONO trianionic pincer ligand precursor of claim 1, consisting of a tri-protonated ONO trianionic pincer ligand precursor with OH and NH functionality, wherein each O⁻ from the OH is separated from the N⁻ from the NH by three bridging carbons, wherein the O⁻s and the N⁻ and the bridging carbons are capable of assuming a coplanar substructure:

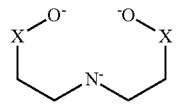

where X is C, and wherein the tri-protonated ONO trianionic pincer ligand precursor with OH and NH functionality has the structure:

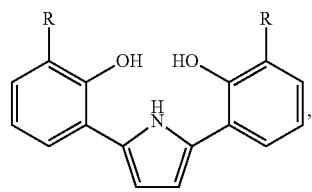

wherein R is independently $C_2$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $_2$-$C_{30}$ alkylester, $C_3$-$C_{30}$ alkeny-lester, $C_3$-$C_{30}$ alkynylester, or perfluorinated, partially fluorinated variations thereof.

4. The ONO trianionic pincer ligand precursor of claim 2, wherein the structure is:

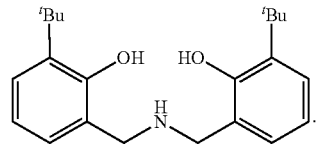 [SMILES: CC(C)(C)c1cccc(CNCc2cccc(C(C)(C)C)c2O)c1O]

5. The ONO trianionic pincer ligand precursor of claim 3, wherein the structure is:

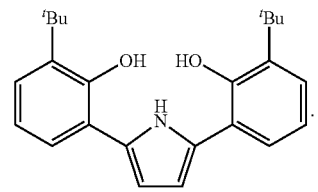 [SMILES: CC(C)(C)c1cccc(-c2ccc(-c3cccc(C(C)(C)C)c3O)[nH]2)c1O]

6. A trianionic ONO pincer ligand comprising transition metal complex comprising:
   at least one ONO trianionic pincer ligand derived from the ONO trianionic pincer ligand precursor of claim 1; and
   a transition metal from group III through group X of the periodic table.

7. The trianionic ONO pincer ligand comprising transition metal complex of claim 6, wherein the transition metal is an early transition metal complex from group III through group VI.

8. The trianionic ONO pincer ligand comprising transition metal complex of claim 6, wherein the structure is:

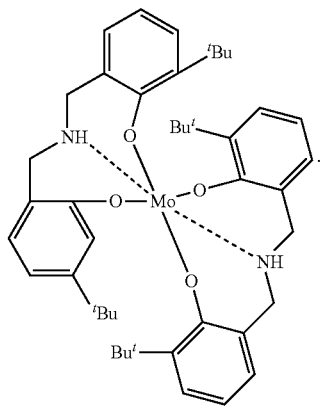

9. The trianionic ONO pincer ligand comprising transition metal complex of claim 6, wherein the structure is:

10. The trianionic ONO pincer ligand comprising transition metal complex of claim 6, wherein the structure is:

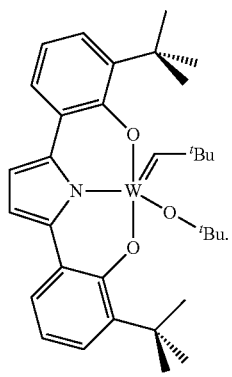

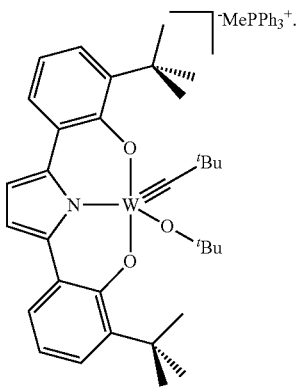

11. A method of preparing an ONO pincer ligand precursor according to claim 1, comprising condensing a nucleophilic oxygen or nucleophilic nitrogen comprising compound with an electrophilic carbon comprising compound further comprising the bridge structure of the resulting ONO pincer ligand.

12. A method of preparing an ONO pincer ligand comprising transition metal complex of claim 6, comprising combining a precursor metal compound comprising a metal alkoxide or metal amide with an ONO pincer ligand precursor of the structure:

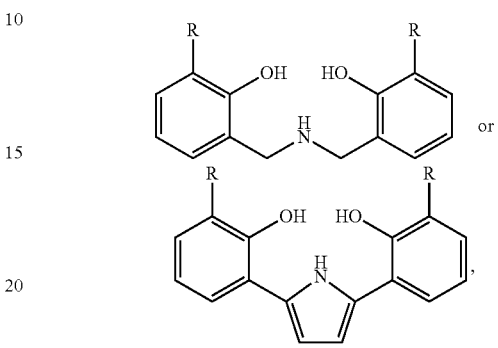

wherein R is independently $C_1$-$C_{30}$ alkyl, $C_2$-$C_{30}$ alkenyl, $C_2$-$C_{30}$ alkynyl, $C_6$-$C_2$-$C_{30}$ alkenyloxy, $C_2$-$C_{30}$ alkynyloxy, $C_2$-$C_{30}$ alkylester, $C_3$-$C_{30}$ alkenylester, $C_3$-$C_{30}$ alkynylester, or perfluorinated, partially fluorinated, and/or otherwise substituted variations thereof; wherein proton and ligand exchange between the anionic ONO pincer ligand precursor and the metal alkoxide or metal amide.

13. The method of preparing an ONO pincer ligand comprising transition metal complex of claim 12, wherein the precursor metal compound further comprises a metal alkylidyne, further comprising adding the OH or NH of the ONO pincer ligand precursor across the metal alkylidyne to form the anionic ONO pincer ligand comprising metal complex.

* * * * *

UNITED STATES PATENT AND TRADEMARK OFFICE
CERTIFICATE OF CORRECTION

PATENT NO. : 9,464,104 B2
APPLICATION NO. : 14/077822
DATED : October 11, 2016
INVENTOR(S) : Adam Steven Veige, Matthew O'Reilly and Muhammad Tariq Jan It is certified that error appears in the above-identified patent and that said Letters Patent is hereby corrected as shown below:

In the Specification

Column 2,
Lines 22-23, "*bis*(1,1,1,3,3,3-hexafluoro-propan-2-0l)" should read --*bis*(1,1,1,3,3,3-hexafluoro-propan-2-ol)--.
Lines 29-30, "W--CHCH$_2$CH$_3$(O$^t$Bu)" should read --W=CHCH$_2$CH$_3$(O$^t$Bu)--.

Column 3,
Lines 15-16, "W[C($^t$Bu)C(Me)C(Ph)]" should read --W=[C($^t$Bu)C(Me)C(Ph)]--.

Column 7,
Lines 66-67, "C$_8$-C$_{30}$ arylalkynyl, alkoxy" should read --C$_8$-C$_{30}$ arylalkynyl, C$_1$-C$_{30}$ alkoxy--.

Column 13,
Line 49, "embodiment of" should read --embodiments of--.

Column 14,
Line 13, "with Nail" should read --with NaH--.
Line 47, "5.05 (s, 21-1, -OC$H_2$OCH$_3$)" should read --5.05 (s, 2H, -OC$H_2$OCH$_3$)--.

Column 15,
Line 20, "NMR (CDCl$_3$)" should read --NMR(CDCl$_3$)--.
Line 27, "NMR(CDCl3)" should read --NMR(CDCl$_3$)--.

Column 16,
Line 63, "Figure 18 give" should read --Figure 18 gives--.

Column 18,
Line 23, "2.14 (s, 311, Ar-C$H_3$)" should read --2.14 (s, 3H, Ar-C$H_3$)--.

Signed and Sealed this
Seventh Day of March, 2017

Michelle K. Lee
*Director of the United States Patent and Trademark Office*

Column 19,
Line 28, "(s, Ar-$C$H$_3$")  ppm." should read --(s, Ar-$C$H$_3$') ppm.--.
Lines 29-30, "C, 46.22%; H, 3.44%; N, 1.54%, Found; C, 46.31%; H, 3.50; N, 1.60%." should read --C: 46.22%; H: 3.44%; N: 1.54%, Found; C: 46.31%; H: 3.50; N: 1.60%.--.
Line 57, "Figure 41 give" should read --Figure 41 gives--.

Column 21,
Line 4, "(br, 1H, NB)" should read --(br, 1H, N$H$)--.
Line 10, "(s, $C$(C-H$_3$)$_3$)" should read --(s, $C$(CH$_3$)$_3$)--.

Column 22,
Line 9, "produce hid" should read --produce hkl--.

In the Claims

Column 23,
Line 3, "$_2$-C$_{30}$ alkylester" should read --C$_2$-C$_{30}$ alkylester--.
Line 34, "$_2$-C$_{30}$ alkylester" should read --C$_2$-C$_{30}$ alkylester--.
Line 67, "$_2$-C$_{30}$ alkylester" should read --C$_2$-C$_{30}$ alkylester--.